(12) United States Patent
Konofagou et al.

(10) Patent No.: US 11,096,660 B2
(45) Date of Patent: Aug. 24, 2021

(54) ULTRASOUND DEVICES METHODS AND SYSTEMS

(71) Applicant: The Trustees of Columbia University in the City of New York, New York, NY (US)

(72) Inventors: Elisa E. Konofagou, New York, NY (US); Jean Provost, New York, NY (US); Jianwen Luo, New York, NY (US); Stanley J. Okrasinski, New York, NY (US); Stéphane Thiébaut, Antony (FR); Vu Thanh-Hieu Nguyen, Lentigny (CH)

(73) Assignee: The Trustees of Columbia University in the City of New York, New York, NY (US)

( * ) Notice: Subject to any disclaimer, the term of this patent is extended or adjusted under 35 U.S.C. 154(b) by 1372 days.

(21) Appl. No.: 15/094,578

(22) Filed: Apr. 8, 2016

(65) Prior Publication Data
US 2016/0296203 A1 Oct. 13, 2016

Related U.S. Application Data

(60) Division of application No. 14/057,685, filed on Oct. 18, 2013, now Pat. No. 9,320,491, which is a
(Continued)

(51) Int. Cl.
*A61B 8/08* (2006.01)
*A61B 8/14* (2006.01)
*A61B 8/00* (2006.01)

(52) U.S. Cl.
CPC ............. *A61B 8/0883* (2013.01); *A61B 8/14* (2013.01); *A61B 8/461* (2013.01); *A61B 8/467* (2013.01);
(Continued)

(58) Field of Classification Search
CPC ......... A61B 5/0883; A61B 8/14; A61B 8/461; A61B 8/467; A61B 8/483; A61B 8/4281; A61B 8/08
See application file for complete search history.

(56) References Cited

U.S. PATENT DOCUMENTS

| 3,598,111 A | 8/1971 | Kahn |
| 4,463,608 A | 8/1984 | Takeuchi et al. |

(Continued)

FOREIGN PATENT DOCUMENTS

| WO | WO 2010044385 | 4/2010 |
| WO | WO 2010063951 | 6/2010 |

(Continued)

OTHER PUBLICATIONS

Arduino, home page, http://www.arduino.cc, accessed Feb. 15, 2019.

(Continued)

*Primary Examiner* — Peter Luong
(74) *Attorney, Agent, or Firm* — Potomac Law Group, PLLC

(57) ABSTRACT

Ultrasound methods, devices, and systems are described which support a useful compromise in terms of spatial resolution and temporal resolution for capturing motion in tissue structures. Tissue engineering articles, methods, systems, and devices which employ ultrasound to deliver biological agents to selected regions of a tissue scaffold, deliver mechanical stimulation to cells growing in a tissue scaffold, and enhance the perfusion of fluids through tissue scaffolds.

6 Claims, 25 Drawing Sheets

Related U.S. Application Data continuation-in-part of application No. PCT/US2012/035685, filed on Apr. 27, 2012, and a continuation-in-part of application No. PCT/US2012/034136, filed on Apr. 18, 2012.

(60) Provisional application No. 61/500,858, filed on Jun. 24, 2011, provisional application No. 61/504,687, filed on Jul. 5, 2011, provisional application No. 61/532,266, filed on Sep. 8, 2011, provisional application No. 61/479,806, filed on Apr. 27, 2011, provisional application No. 61/476,573, filed on Apr. 18, 2011.

(52) U.S. Cl.
CPC .............. *A61B 8/483* (2013.01); *A61B 8/08* (2013.01); *A61B 8/4281* (2013.01)

(56) References Cited

U.S. PATENT DOCUMENTS

| | | | |
|---|---|---|---|
| 4,777,599 A | 10/1988 | Dorogi et al. |
| 4,822,679 A | 11/1989 | Tuy et al. |
| 4,882,679 A | 11/1989 | Tuy et al. |
| 5,038,787 A | 8/1991 | Antich et al. |
| 5,107,837 A | 4/1992 | Ophir et al. |
| 5,178,147 A | 1/1993 | Ophir et al. |
| 5,309,914 A | 5/1994 | Ilnuma |
| 5,433,708 A | 7/1995 | Nichols et al. |
| 5,435,310 A | 7/1995 | Sheehan et al. |
| 5,457,754 A | 10/1995 | Han et al. |
| 5,601,084 A | 2/1997 | Sheehan et al. |
| 5,606,971 A | 3/1997 | Sarvazyan |
| 5,662,113 A | 9/1997 | Liu |
| 5,722,411 A | 3/1998 | Suzuki et al. |
| 5,752,515 A | 5/1998 | Jolesz et al. |
| 5,810,731 A | 9/1998 | Sarvazyan et al. |
| 5,840,028 A | 11/1998 | Chubachi et al. |
| 5,840,208 A | 11/1998 | Chubachi et al. |
| 5,928,151 A | 7/1999 | Hossack et al. |
| 6,026,173 A | 2/2000 | Svenson et al. |
| 6,102,864 A | 8/2000 | Hatfield et al. |
| 6,102,865 A | 8/2000 | Hossack et al. |
| 6,106,465 A | 8/2000 | Napolitano et al. |
| 6,123,669 A | 9/2000 | Kanda |
| 6,152,878 A | 11/2000 | Nachtomy et al. |
| 6,241,675 B1 | 6/2001 | Smith et al. |
| 6,246,895 B1 | 6/2001 | Plews |
| 6,270,459 B1 | 8/2001 | Konofagou et al. |
| 6,312,382 B1 | 11/2001 | Mucci et al. |
| 6,352,507 B1 | 3/2002 | Torp et al. |
| 6,413,216 B1 | 7/2002 | Cain et al. |
| 6,425,867 B1 | 7/2002 | Vaezy et al. |
| 6,491,636 B2 | 12/2002 | Chenal et al. |
| 6,508,768 B1 | 1/2003 | Hall et al. |
| 6,520,913 B1 | 2/2003 | Pesavento et al. |
| 6,537,217 B1 | 3/2003 | Bjærum et al. |
| 6,537,221 B2 | 3/2003 | Criton et al. |
| 6,671,541 B2 | 12/2003 | Bishop et al. |
| 6,683,454 B2 | 1/2004 | Rehwald et al. |
| 6,685,641 B2 | 2/2004 | Liu |
| 6,689,060 B2 | 2/2004 | Phelps et al. |
| 6,701,341 B1 | 3/2004 | Wu et al. |
| 6,770,033 B1 | 8/2004 | Fink et al. |
| 6,875,176 B2 | 4/2005 | Mourad et al. |
| 7,055,378 B2 | 6/2006 | Su et al. |
| 7,257,244 B2 | 8/2007 | Miga |
| 7,331,926 B2 | 2/2008 | Varghese et al. |
| 7,421,101 B2 | 9/2008 | Georgescu et al. |
| 7,449,306 B2 | 11/2008 | Elson |
| 7,601,122 B2 | 10/2009 | Zagzebski et al. |
| 7,753,847 B2 | 7/2010 | Greenleaf et al. |
| 7,789,841 B2 | 9/2010 | Huckle et al. |
| 7,905,148 B2 | 3/2011 | Righetti et al. |
| 8,029,444 B2 | 10/2011 | Pedrizzetti et al. |
| 8,150,128 B2 | 4/2012 | Fung-Kee-Fung et al. |
| 2002/0038086 A1 | 3/2002 | Hynynen et al. |
| 2002/0065461 A1 | 5/2002 | Cosman |
| 2002/0095081 A1 | 7/2002 | Vilsmeier |
| 2002/0169394 A1 | 11/2002 | Eppstein et al. |
| 2002/0193784 A1 | 12/2002 | McHale et al. |
| 2003/0097068 A1 | 5/2003 | Hossack et al. |
| 2003/0171672 A1 | 9/2003 | Varghese et al. |
| 2003/0220556 A1 | 11/2003 | Porat et al. |
| 2004/0006266 A1 | 1/2004 | Ustuner et al. |
| 2004/0049134 A1 | 3/2004 | Tosaya |
| 2004/0054357 A1 | 3/2004 | O'Donnell |
| 2004/0059224 A1 | 3/2004 | Varghese et al. |
| 2004/0092816 A1 | 5/2004 | Ossmann et al. |
| 2004/0172081 A1 | 9/2004 | Wang |
| 2004/0249580 A1 | 9/2004 | Pourcelot et al. |
| 2004/0210135 A1 | 10/2004 | Hynynen |
| 2004/0236219 A1 | 11/2004 | Liu et al. |
| 2005/0004466 A1 | 1/2005 | Hynynen et al. |
| 2005/0267695 A1 | 1/2005 | German |
| 2005/0054930 A1 | 3/2005 | Rickets et al. |
| 2005/0059876 A1 | 3/2005 | Krishnan et al. |
| 2005/0080336 A1 | 4/2005 | Byrd et al. |
| 2005/0259864 A1 | 11/2005 | Dickinson et al. |
| 2006/0058673 A1 | 3/2006 | Aase et al. |
| 2006/0074315 A1 | 4/2006 | Liang et al. |
| 2006/0173320 A1 | 8/2006 | Radulescu |
| 2007/0049824 A1 | 3/2007 | Konofagou et al. |
| 2007/0219447 A1 | 9/2007 | Kanai et al. |
| 2007/0239001 A1 | 10/2007 | Mehi et al. |
| 2007/0276242 A1 | 11/2007 | Konofagou |
| 2007/0276245 A1 | 11/2007 | Konofagou |
| 2007/0276254 A1 | 11/2007 | Yang et al. |
| 2007/0299539 A1 | 12/2007 | Othman et al. |
| 2008/0194957 A1 | 8/2008 | Hoctor et al. |
| 2008/0269606 A1 | 10/2008 | Matsumura |
| 2008/0285819 A1 | 11/2008 | Konofagou et al. |
| 2009/0221916 A1 | 9/2009 | Konofagou et al. |
| 2011/0208038 A1 | 8/2011 | Konofagou et al. |

FOREIGN PATENT DOCUMENTS

| | | |
|---|---|---|
| WO | WO 2011/028690 | 3/2011 |
| WO | 2011075557 A1 | 6/2011 |
| WO | 2012145442 A1 | 10/2012 |

OTHER PUBLICATIONS

Azar et al., "2-D high-frame-rate dynamic elastography using delay compensated and angularly compounded motion vectors: preliminary results," IEEE transactions on Ultrasonics, Ferroelectrics, and Frequency Control, Nov. 2010, vol. 57(11), pp. 2421-2436.

Baghani et al., "A High-Frame-Rate Ultrasound System for the Study of Tissue Motions," IEEE Transactions on Ultrasonics, Ferroelectrics, and Frequency Controls, vol. 57, No. 7, pp. 1535-1547, Jul. 2010.

Bercoff, "Ultrafast ultrasound imaging and its application to investigate soft tissues viscoelastic properties," Doctoral Thesis, University of Paris, Dec. 2004.

Brumbi, "Level Measurement," The Measurement, Instrumentation and Sensors Handbook, John G. Webster, ed., IEEE Press, Section 11, 1999.

Butler et al., "Functional tissue engineering for tendon repair: A multidisciplinary strategy using mesenchymal stem cells, bioscaffolds, and mechanical stimulation," Journal of Orthopaedic Research, Jan. 1, 2008, vol. 26(1), pp. 1-9.

Chen et al., "High-Frequency Periodic Sources Underlie Ventricular Fibrillation in the Isolated Rabbit Heart," Circulation Research, vol. 86, pp. 86-93, 2000.

Chen et al., "Ultrasound frame rate requirements for cardiac elastography: Experimental and in vivo results," Ultrasonics, vol. 49, pp. 98-111, Jun. 2008.

Cheng et al., "Extended High-Frame Rate Imaging Method with Limited-Diffraction Beams," IEEE Transactions on Ultrasonics, Ferroelectrics, and Frequency Control, vol. 53, No. 5, pp. 880-899, May 2006.

(56) References Cited

OTHER PUBLICATIONS

Choi et al., "Microbubble-Size Dependence of Focused Ultrasound-Induced Blood-Brain Barrier Opening in Mice in vivo", IEEE Transactions on Biomedical Engineering, vol. 57, No. 1, pp. 145-154, Jan. 2010.
Dewire et al., "State-of-the-art and emerging technologies for atrial fibrillation ablation," Nature Reviews, vol. 7, No. 3, pp. 129-138, Mar. 2010, Abstract.
D'Hooge et al., "Two-Dimensional Ultrasonic Strain Rate Measurement of the Human Heart in Vivo," Ultrasonics, Ferroelectics and Frequency Control, IEEE Transactions, vol. 49, pp. 281-286, 2002.
Durney et al., "Using Microbubbles to Modulate Hydrogel Scaffold Properties for Cartilage Tissue Engineering," 56th Annnual Meeting of the Orthop. Res. Soc., Paper 91, 2010.
Federal Drug Administration, Guidance for Industry and FDA Staff: Information for Manufacturers Seeking Marketing Clearance of Diagnostic Ultrasound Systems and Transducers, Sep. 9, 2008.
Fuster et al., "2006 Guidelines for the Management of Patients with Atrial Fibrillation," Circulation, vol. 114, pp. e257-e354, 2006.
Garcia et al., The Art of Interpretation. Emergency Medical Services, p. 5, 2001.
Gupta et al., "Cardiac Mapping: Utility or Futility?," Indian Pacing and Electrophysiology, vol. 2, No. 1, pp. 20-32, 2002.
Gurev et al., "Models of cardiac electromechanics based on individual hearts imaging data," Biomech. Model Mechanobiol., vol. 10, pp. 295-306, Jun. 2011.
Holy et al., "Engineering three-dimensional bone tissue in vitro using biodegradable scaffolds: investigating initial cell-seeding density and culture period," Journal of Biomedical Materials Research, Sep. 5, 2000, vol. 51(3), pp. 376-382.
Honjo et al., "Two-Dimensional Tracking of Heart Wall for Detailed Analysis of Heart Function at High Temporal and Spatial Resolutions," Japanese Journal of Applied Physics, vol. 49, p. 07HF14, 2010.
Jensen, "Field: A Program for Simulating Ultrasound Systems," 10th Nordic-Baltic Conference on Biomedical Imaging, vol. 4, pp. 351-353, 1996.
Jensen, Estimation of Blood Velocities Using Ultrasound: A Signal Processing Approach, Cambridge, Univ. Press., 1996 (Abstract).
Kirisli et al., "A patient-specific visualization tool for comprehensive analysis of coronary CTA and perfusion MRI data," Medical Imaging 2011: Visualization, Image-Guided Procedures and Modeling, Wong et al., Eds., vol. 7964, 2011.
Knight et al., "Control of ventricular rate in atrial flutter," www.uptodate.com, 2011.
Konofagou et al., "Imaging the mechanics and electromechanics of the heart," International Conference of the IEEE Engineering in Medicine and Biology Society, Suppl. 6648-6651, Aug. 2006.
Konofagou et al., "Noninvasive electromechanical wave imaging and conduction-relevant velocity estimation in vivo," Ultrasonics, vol. 50, Feb. 2010, pp. 208-215.
Lee, "Myocardial elastography: A strain imaging technique for the reliable detection and localization of myocardial ischemia in vivo," Columbia University Thesis, 2010.
Lloyd-Jones et al., "Heart Disease and Stroke Statistics—2009 Update," Circulation, vol. 119, pp. e21-e181, Jan. 2009.
Luo et al., "P4A-2: An in-Vitro Study of Frame Rate Optimization for Myocardial Elastography," Ultrasonics Symposium 2007, pp. 1933-1936, 2007.
Madore et al., "Accelerated Focused Ultrasound Imaging," IEEE Transactions on Ultrasound, Ferroelectrics and Frequency Control, vol. 56, No. 12, pp. 489-506, 2009.
McVeigh et al., "Electromechanical Mapping with MRI Tagging and Epicardial Sock Electrodes," J. Electrocardiol., vol. 35, Suppl., pp. 61-64, 2002.
Meunier et al., "Ultrasonic Texture Motion Analysis: Theory and Simulation," IEEE Transactions on Medical Imaging, vol. 14, No. 2, pp. 293-300, Jun. 1995.

Misaridis et al., "Use of Modulated Excitation Signals in Medical Ultrasound. Part III: High Frame Rate Imaging," IEEE Transactions on Ultrasonics, Ferroelectrics, and Frequency Control, vol. 52, No. 2, pp. 208-219, Feb. 2005.
Montaldo et al., "Coherent plane-wave compounding for very high frame rate ultrasonography and transient elastography," IEEE Transactions on Ultrasonics, Ferroelectrics, and Frequency, vol. 56, Issue 3, pp. 489-506, Mar. 2009.
Nover et al., "A Focused Ultrasound Technique for Modulating Local Tissue Properties for Articular Cartilage Tissue Engineering," ORS Annual Meeting, Paper 121, 2012.
Nover et al., "Albumin as a Substrate for Focused Ultrasound Sealing of Engineered Cartilage," Trans. Orthop. Res. Soc., 37:1446, 2012.
Nover et al., "Effects of Focused Ultrasound on Cell Viability in Its Application to Articular Cartilage Engineering," Transactions of the Annual Meeting of the Biomedical Engineering Society, Oct. 12-15, 2011.
Paul et al., "Epicardial Mapping: How to Measure Local Activation?," Pacing and Clinical Electrophysiology, vol. 13, Issue 3, pp. 285-292, Mar. 1990.
Provost et al, "Mapping of cardiac electrical activation with electromechanical wave imaging: An in silico-in vivo reciprocity study," Heart Rhythm: The Official Journal of the Heart Rhythm Society, in Press.
Provost et al., "Imaging the Electromechanical Activity of the Heart in Vivo." Proceedings of the National Academy of Sciences of the United States of America, v. 108,21 pp. 8565-8570. doi: 10.1073/pnas.1011688108.
Provost et al., "Single-heartbeat electromechanical wave imaging with optimal strain estimation using temporally unequispaced acquisition sequences," Physics in Medicine & Biology, Feb. 1, 2012, vol. 57(4), pp. 1095-1112.
Provost et al., "Electromechanical Wave Imaging of Normal and Ischemic Hearts in Vivo," IEEE Transactions on Medical Imaging, vol. 29, Mar. 2010, pp. 625-635.
Provost et al., Electromechanical Wave Imaging for Noninvasive Mapping of the 3D Electrical Activation Sequence in vivo, Circulation, Nov. 23, 2010, vol. 122(21), Abstract 21142.
Shattuck et al., "Explososcan: A parallel processing technique for high speed ultrasound imaging with linear phased arrays," The Journal of the Acoustical Society of America, vol. 75, pp. 1273-1282, Apr. 1984.
Varghese et al., "A theoretical framework for performance charactrization of elastography: the strain filter," IEEE Transactions on Ultrasonics, Ferroelectrics, and Frequency Control, vol. 44, pp. 164-172, 1997, Abstract.
Weinstein et al., "Fundamental limitations in passive time-delay estimation Part II: Wide-band systems," IEEE Transactions on Acoustics, Speech and Signal Processing, vol. 32, pp. 1064-1078, 1984, Abstract.
Wiecek et al., "Advanced Thermal Image Processing," The Biomecial Engineering Handbook, Bronzino, Ed., Chapter 28, CRC Press, 2000.
World Health Organization, "Cardiovascular Diseases," Fact Sheet, 2011, https://www.who.int/nmh/publications/fact_sheet_cardiovascular_en.pdf.
U.S. Appl. No. 12/096,254, filed Nov. 2008, Konofagou et al.
Epstein-Barash et al., "A microcomposite hydrogel for repeated on-demand ultrasound-triggered drug delivery," Biomaterials, Mar. 29, 2010, 31: pp. 5208-5217.
Duck, "Physical properties of tissue: a comprehensive reference book. 1990 Academic Press," London, UK.
Jensen et al., "Calculation of pressure fields from arbitrarily shaped, apodized, and excited ultrasound transducers," IEEE Transactions on Ultrasonics, Ferroelectrics and Frequency Control, vol. 39(2), pp. 262-267, Mar. 1992.
Mitri et al., "Chirp imaging vibro-acoustography for removing the ultrasound standing wave artifact," IEEE transactions on medical imaging, vol. 24(10), pp. 1249-1255, Oct. 2005.
Bers, "Cardiac excitation-contraction coupling," Nature, Jan. 10, 2002, vol. 415:198-205.

(56) References Cited

OTHER PUBLICATIONS

Ramanathan et al., (2004) "Noninvasive electrocardiographic imaging for cardiac electrophysiology and arrhythmia," Nat Med 10(4):422-428.
Berger et al., (2006) "Single-Beat Noninvasive Imaging of Cardiac Electrophysiology of Ventricular Pre-Excitation," Journal of the American College of Cardiology 48(10):2045-2052.
Greenstein et al., (2006) "Mechanisms of Excitation-Contraction Coupling in an Integrative Model of the Cardiac Ventricular Myocyte," Biophysical Journal 90:77-91.
Rice et al., "Approximate model of cooperative activation and crossbridge cycling in cardiac muscle using ordinary differential equations," Biophys. J 95:2368-2390, Sep. 2008.
Campbell et al., "Mechanisms of transmurally varying myocyte electromechanics in an integrated computational model," Phl. Trans. R. Soc. A., 366:3361-3380, Jul. 1, 2008.
Gurev et al., "Distribution of Electromechanical Delay in the Heart: Insights from a Three-Dimensional Electromechanical Model," Biophysical Journal 99:745-754, Aug. 2010.
Badke et al., (1980) "Effects of ventricular pacing on regional left ventricular performance in the dog," Am J Physiol Heart Circ Physiol 238:H858-867.
Wyman et al., (1999) "Mapping propagation of mechanical activation in the paced heart with MRI tagging," Am J Physiol Heart Circ Physiol 276:H881-891.
Prinzen et al., (1992) "The time sequence of electrical and mechanical activation during spontaneous beating and ectopic stimulation," Eur Heart J 13:535-543.
Provost et al., (2010) "Electromechanical Wave Imaging of Normal and Ischemic Hearts in Vivo," IEEE Trans. Med. Imaging 29(3):625-635.
Shehata et al., (2009) "Myocardial tissue tagging with cardiovascular magnetic resonance," Journal of Cardiovascular Magnetic Resonance 11:55.
Zwanenburg et al., (2004) "Timing of cardiac contraction in humans mapped by high-temporal-resolution MRI tagging: early onset and late peak of shortening in lateral wall," Am J Physiol Heart Circ Physiol 286:H1872-1880.
Walker, (1994) "A fundamental limit on the performance of correlation based phase correction and flow estimation techniques" Ultrasonics, Ferroelectrics and Frequency Control, IEEE Transactions on 41(5):644-654, Sep. 1994.
Pernot et al., "Electromechanical Imaging of the Myocardium at Normal and Pathological States," Ultrasonics Symposium, 2005 IEEE, pp. 1091-1094, 2005.
Pernot et al., (2007) "ECG-gated, Mechanical and Electromechanical Wave Imaging of Cardiovascular Tissues in Vivo," Ultrasound in Medicine & Biology 33(7):1075-1085.
Provost et al., (2008) in 2008 IEEE International Ultrasonics Symposium (Beijing, China).
Durrer et al., (1970) "Total Excitation of the Isolated Human Heart. Circulation," 41:899-912.
Sengupta et al., (2008) "Electromechanical activation sequence in normal heart," Heart Fail Clin 4:303-14.
Scher et al., (1956) "The pathway of ventricular depolarization in the dog," Circ Res 4:461-469.
Faris et al., (2003) "Novel Technique for Cardiac Electromechanical Mapping with Magnetic Resonance Imaging Tagging and an Epicardial Electrode Sock," Ann Biomed Eng. 31:430-440.
Gurev et al., (2009) "In silico characterization of ventricular activation pattern by electromechanical wave imaging," Supplement to Heart Rhythm 6:S357.
Ramanathan et al., "Activation and repolarization of the normal human heart under complete physiological conditions," Proceedings of the National Academy of Sciences 103(16):6309-6314, Apr. 18, 2006.
Lee et al., "Theoretical Quality Assessment of Myocardial Elastography with in Vivo Validation," Ultrasonics, Ferroelectrics and Frequency Control, IEEE Transactions on 54(1):2233-2245, Nov. 11, 2007.

Kimber et al., (1996) "A Comparison of Unipolar and Bipolar Electrodes During Cardiac Mapping Studies," Pacing Clin Electro 19:1196-1204.
Kallel et al., (1997) "A least-squares strain estimator for elastography," Ultrason Imaging 19:195-208.
Luo et al., "High-frame rate, full-view myocardial elastography with automated contour tracking in murine left ventricles in vivo," IEEE Transactions on Ultrasonics, Ferroelectrics and Frequency Control, 55(1):240-248, Jan. 2008.
Lai et al., (1993) "Introduction to Continuum Mechanics (Pergamon Pr)," 3rd Ed., Contents.
Stewart et al., "Blood-eye barriers in the rat: Correlation of ultrastructure with function," J. Comp. Neurol., vol. 340, No. 4, pp. 566-576, 1994.
Samuel et al., "An ex vivo study of the correlation between acoustic emission and microvascular damage," Ultrasound Med. Biol., vol. 35, No. 9, pp. 1574-1586, 2009.
Luo et al., "Pulse wave imaging of normal and aneurysmal abdominal aortas in vivo," IEEE Trans. Med. Imaging 28(4): 477-486, 2009.
Luo et al., "A fast normalized cross-correlation method for motion estimation," IEEE Trans. Ultrason. Ferroelectr. Control 57(6): 1347-1357, Jun. 2010.
Maleke et al., "Single-Element focused Ultrasound Transducer Method for Harmonic Motion Imaging," Ultrason. Imagin, vol. 28, No. 3, pp. 144-158, 2006.
Maleke et al., "In Vivo Feasibility of Real-time Monitoring of Focused Ultrasound Surgery (FUS) Using Harmonic Motion Imaging (HMI)," IEEE Trans. Biomed. Eng., vol. 57(1), pp. 7-11, Jan. 2010.
Vappou et al., "Quantitative Viscoelastic Parameters Measured by Harmonic Motion Imaging," Phys. Med. Biol., vol. 54, pp. 3579-3595, Mar. 2009.
Ophir et al., "Elastography: A quantitative method for imaging the elasticity of biological tissues," Ultrasonic Imaging, vol. 13(2), pp. 111-134, 1991.
Konofagou et al., "Noninvasive Electromechanical Wave Imaging and Conduction Velocity Estimation in Vivo," Ultrasonics Symposium, 2007 IEEE, pp. 969-972, 2007.
Konofagou, et al., "Electromechanical Wave imaging for noninvasive mapping of the 3D electrical activation sequence in canines and humans in vivo," Journal of Biomechanics, 45(5):856-864 (Mar. 15, 2012).
Otani, et al., "Transmural ultrasound-based visualization of patterns of action potential wave propagation in cardiac tissue," Annals Biomedical Engineering, 38(10):3112-3123 (2010).
Chen, et al., "Architectural Acoustics and Noise: Advancements and Best Practices in Instrumentation for Architectural Acoustics and Noise," J. Acoust. Soc. Am.; 164th Meeting: Acoustical Society of America, 132(3, Pt. 2):1977-2018 (Sep. 2012) Cited in IR Assessments: Chen, et al., Radiation-Force-Based Estimation of Acoustic Attenuation Using Harmonic Motion Imaging (HMI) in Phantoms and in Vitor Livers Before and After HIFU Ablation, Ultrasound in Medicine and Biology, Submitted and included in IR Report.
Palmeri, et al., "Characterizing Acoustic Attenuation of Homogeneous Media Using Focused Impulsive Acoustic Radiation Force", Ultrasonic Imaging, 28(2):114-128 (2006).
Duerinckx, et al., "In vivo Acoustic Attenuation in Liver: Correlations with Blood Tests and Histology," Ultrasonic in Medicine & Biology, 14(5):405-413 (1988).
Fujii, et al., "A New Method for Attenuation Coefficient Measurement in the Liver," Journal of Ultrasound in Medicine, 21(7):783-788 (2002).
Damianou, et al., "Dependence of Ultrasonic Attenuation and absorption in dog soft tissues on Temperature and Thermal dose," The Journal of Acoustical Society of America, 102(1):628-634 (1997).
Techavipoo, et al., "Temperature Dependence of Ultrasonic Propagation Speed and Attenuation in Excised Canine Liver Tissue Measured Using Transmitted and Reflected Pulses," The Journal of Acoustical Society of America, 115(6):2859-2865 (2004).
Papadakis, Emmauel P., "Ultrasonic Instruments & Devices," Academic Press, 1999.

(56) References Cited

OTHER PUBLICATIONS

Cobbold, "Foundations of biomedical ultrasound," Biomedical engineering series, Oxford University Press, pp. 422-423 (2006).
DuBose, et al., "Confusion and Direction in Diagnostic Doppler Sonography," Journal of Diagnostic Medical Sonography, 25(3):173-177 (2009).
Fenster, et al., "Three-dimensional ultrasound imaging," Physics in Medicine and Biology, 46(5):R67-R99 (2001).
De Craene, et al., "Temporal diffeomorphic free-form deformation: Application to motion and strain estimation from 3D echocardiography," Medical Image Analysis, 16(2):427-450 (2012).
Housden, et al., "Ultrasonic imaging of 3D displacement vectors using a simulated 2D array and beamsteering," Ultrasonics, 53(2):615-621 (2013).
Jasaityte, et al., "Current state of three dimensional myocardial strain estimation using echocardiography," Journal of the American Society of Echocardiography, 26(1):15-28 (2013).
Konofagou et al., "Noninvasive electromechanical wave imaging and conduction-relevant velocity estimation in vivo," Ultrasonics, 50(2):208-215 (2010).
Provost et al., "Imaging the electromechanical activity of the heart in vivo," Proceedings of the National Academy of Sciences, 108:8565-8570 (2011).
Provost et al., "Mapping of cardiac electrical activation with electromechanical wave imaging: An in silico—in vivo reciprocity study," Heart Rhythm, 8(5):752-759 (2011).
Otani, et al., "Use of ultrasound imaging to map propagating action potential waves in the heart," Computers in Cardiology, 36:617-620 (2009).
Ginat, et al., "High-resolution ultrasound elastography of articular cartilage in vitro," Proceedings of the 28th IEEE EMBS Annual International Conference, New York City, US App. 6644-6647 (Aug. 30-Sep. 3, 2006).
Zheng, et al., "Ultrasonic measurement of depth-dependent transient behaviors of articular cartilage under compression," Journal of Biomechanics, 38:1830-1837 (2005).
Shinna, et al., "Realtime tissue elasticity imaging using the combined autocorrelation method," J. Med. Ultrasonics, 29 (autumn):119-128 (2002).
Borden et al., "Ultrasound Radiation Force Modulates Ligand Availability on Target Contrast Agents," Mol. Imaging, 5:139-147 (2006).
Vial (en.wikipedia.org/wiki/Vial) downloaded May 20, 2014.
European Search Report for EP Application No. EP 10838238, dated May 6, 2014.
Chen, et al., "Engineering Acoustics and ASA Committee on Standards: Sound Intensity Measurements," J. Acoust. Soc. Am.; 164th Meeting: Acoustical Society of America, 132(3, Pt. 2):1984 (Sep. 2012); Cited in IR Assessment as: Chen, et al., Radiation-Force-Based Estimation of Acoustic Attenuation Using Harmonic Motion Imaging (HMI) in Phantoms and in Vito Livers Before and After HIFU Ablation, Ultrasound in Medicine and Biology, Submitted and included in IR Report.
Choi et al Brain region and microbubble-size dependence of the focused ultrasound-induced blood-brain barrier opening in mice in vivo, IEEE International Ultrasonics Symposium, Rome, ITA, Sep. 20-23, 2009.
Huang et al Watershed Segmentation for Breast Tumor in 2-D Sonography, May 2004, Ultrasound in Medicine and Biology, pp. 625-632.
Chang et al. 3-D US Frame Positioning Using Speckle Decorrelation and Image Registration, Jun. 2003, Ultrasound in Medicine and Biology, pp. 801-812.
EPO Search Report & Opinion and Office Action for EP0684017.2 dated Dec. 7, 2009 & dated Mar. 8, 2010.
Chen, Q. et al. "Estimation of Displacement Vectors and Strain Tensors in Elastography Using Angular Insonifications." *IEEE Transactions on Medical Imaging*, vol. 23, No. 12, pp. 1479-1489 (Dec. 1, 2004).

Choi, J.J. et al., "Optimization of Blood-Brain Barrier Opening in Mice using Focused Ultrasound.", 2006 IEEE Ultrasounics Symposium [online], Jun. 2007.
Choi JJ, Wang S, Brown TR, Small SA, Duff KE and Konofagou EE, "Noninvasive and Transient Blood-Brain Barrier Opening in the Hippocampus of Alzheimer's Double Transgenic Mice Using Pulsed Focused Ultrasound", Ultrasonic Imaging, 189-200, 2008.
Choi JJ, Wang S, Tung Y-S, Baseri B, Morrison B 3$^{rd}$, Konofagou EE. "Delivery of pharmacologically-relevant sized molecules through the ultrasound-induced blood-brain barrier opening in vivo.", Neuroscience, Chicago, IL, USA, Oct. 17-21, 2009.
Feshitan, J.A. et al., "Microbubble size isolation by differential centrifuguation", Journal of Colloid and Interface Science 329 (2009) 316-324.
International Search Report for PCT/US07/0191949 dated Feb. 29, 2008.
International Preliminary Report on Patentability for PCT/US07/019149 dated Mar. 3, 2009, including the Written Opinion of the International Searching Authority dated Feb. 29, 2008.
International Search Report for PCT/US06/061809 dated Oct. 4, 2007.
International Preliminary Report on Patentability for PCT/US06/061809 dated Jun. 11, 2008, including the Written Opinion of the International Searching Authority dated Oct. 4, 2008.
International Preliminary Report on Patentability for PCT/US06/018454 dated Nov. 14, 2007, including the Written Opinion of the International Searching Authority dated Aug. 9, 2007.
International Search Report for PCT/US05/037669 dated Jun. 13, 2006.
International Preliminary Report on Patentability for PCT/US05/37669 dated Apr. 17, 2007, including the Written Opinion of the International Searching Authority dated Jun. 13, 2006.
International Search Report for PCT/US05/037670 dated Nov. 22, 2006.
International Preliminary Report on Patentability for PCT/US05/037670 dated Apr. 17, 2007, including the Written Opinion of the International Searching Authority dated Nov. 22, 2006.
International Search Report and Written Opinion of the International Searching Authority for PCT/US09/052563 dated Oct. 8, 2009.
Konofagou E E et al. "Elastographic Imaging of the Strain Distribution at the Anterior Cruciate Ligament and ACL-Bone Insertions" *27$^{th}$ Annual International Conference of the Engineering in Medicine and Biology Society*, pp. 972-975 (Shanghai, China Sep. 1-4, 2005).
McDannold, N. et al., "Blood-Brain Barrier Disruption Induced by Focused Ultrasound and Circulating Performed Microbubbles Appears to be Characterized by the Mechanical Index.", Ultrasound Med Biol. Jan. 2008, v. 34(5), pp. 834-840.
McNally, D. et al. "Computer Vision Elastography: Speckle Adaptive Motion Estimation for Elastography Using Ultrasound Sequences." *IEEE Transactions on Medical Imaging*, vol. 24, No. 6, pp. 755-766 (2005).
Qin, S. and Ferrara, K.W., "Acoustic response of compliable microvessels containing ultrasound contrast agents", Phys. Med. Biol. 51 (2006) 5065-5088.
Qin, S. and Ferrara, K.W., "The National Frequency of Nonliner Oscillation of Ultrasound Contrast Agents in Microvessels", Ultrasound in Med. & Biol., vol. 33, No. 7, pp. 1140-1148, 2007.
Sassaroli, E. and Hynynen, K., "Forced linear oscillations of microbubbles in blood capillaries", J. Acoust. Soc. Am. 115(6), Jun. 2004.
Sassaroli, E. and Hynynen, K., "Resonance frequency of microbubbles in small blood vessels: a numerical study", Phys. Med. Biol. 50 (2005) 5293-5305.
Sassaroli, E. and Hynynen, K., "Cavitation Threshold of Microbubbles in Gel Tunnels by Focused Ultrasound", Ultrasound in Med. & Biol., vol. 33, No. 10, pp. 1651-1660, 2007.
Silva, G.A. Nanotechnology approaches to crossing the blood-brain barrier and drug delivery to the CNS, BMC Neurosci. 9(Suppl 3): S4, 2008.

(56) References Cited

OTHER PUBLICATIONS

Unger, E.C. et al., "Therapeutic Applications of Lipid-Coated Microbubbles." Advanced Drug Delivery Reviews. May 2004, vol. 56(9), pp. 1291-1314.
Yuh, EL et al. Delivery of Systemic Chemotherapeutic Agent to Tumors by Using Focused Ultrasound: Study in a Murine Model. Radiology, 234(2): 431-437, 2005.
Zheng, Y.P. et al. "High Resolution ultrasound elastomicroscopy imaging of soft tissues: system development and feasibility; Ultrasound elastomicroscopy." Physics in Medicine and Biology, vol. 49, No. 17, pp. 3925-3938 (Sep. 7, 2004).
Luo J, Fujikura K., Homma S, Konofagou EE (Aug. 2007). Myocardial elastography at both high temporal and spatial resolution for the detection of infarcts. Ultrasound in Medicine & Biology 33(8): 1206-23.
Notification of Transmittal of the International Search Report and the Written Opinion of the International Searching Authority, or the Declaration International Application No. PCT/US/06/18454 dated Aug. 9, 2007.
Brekke, S.; Tegnander, E.; Torp, H.G.; Eik-Nes, S.H.; "Tissue Doppler gated (TDOG) dynamic three-dimensional ultrasound imaging of the fetal heart," Ultrasound Obstet Gynecol 2004 vol. 24(2); pp. 192-198.
Wang, Shougang; Lee, Wei-Ning; Luo, Jianwen; Konofagou, Elisa E.; "A composite imaging technique for high frame-rate and full-view cardiovascular ultrasound and elasticity imaging," IEEE Transactions on Ultrasonics, Ferrorelectrics, and Frequency Control 2008 vol. 55(10); pp. 2221-2233.
Wang, Shougang; Lee, Wei-Ning; Luo, Jianwen; Konofagou, Elisa E.; "A composite imaging technique for high frame-rate and full-view cardiovascular ultrasound and elasticity imaging," IEEE International Ultrasonics Symposium, New York, NY, Oct. 28-31, 2007.
Kanai, H. Propagation of spontaneously actuated pulsive vibration in human heart wall and in vivo viscoelasticity estimaton. Ieee T Ultrason Ferr (2005) 52(11): 1931-1942.
Bercoff, J., Tanter, M., and Fink, M. (2004). Supersonic shear imaging: A new technique for soft tissue elasticity mapping. IEEE Transactions on Ultrasonics Ferroelectrics and Frequency Control 51, 396-409.
McLaughlin, J., M. McNeill, B. Braun and P. D. McCormack. Piezoelectric sensor determination of arterial pulse wave velocity. Physiol Meas (2003) 24(3): 693-702.
Greenwald, S.E. Pulse pressure and arterial elasticity. Qjm—an International Journal of Medicine (2002) 95(2): 107-112.
Tanter, M., J. Bercoff, L. Sandrin and M. Fink. Ultrafast compound imaging for 2-D motion vector estimation: application to transient elastography. IEEE Trans Ultrason Ferroelectr Freq Control (2002) 49(10): 1363-74.
Kanai, H. and Y. Koiwa. Myocardial rapid velocity distribution. Ultrasound Med Biol (2001) 27(4): 481-498.
Rogers, W.J., Y.L. Hu, D. Coast, D.A. Vido, C.M. Kramer, R.E. Pyeritz and N. Reichek. Age-associated changes in regional aortic pulse wave velocity. J Am Coll Cardiol (2001) 38(4): 1123-9.
Declerck, J., T.S. Denney, C. Ozturk, W. O'Dell and E.R. McVeigh. Left ventricular motion reconstruction from planar tagged MR images: a comparison. Phys Med Biol. (2000) 45(6): 1611-1632.
Kanai, H., A. Umezawa and Y. Koiwa (2000). Transcutaneous measurement of frequency dispersion in the regional pulse wave velocity. IEEE Ultrasonics symposium.
Roth, B .J. (2000). Influence of a perfusing bath on the foot of the cardiac action potential. Circulation Research 86, E19-E22.
Sinkus, R., J. Lorenzen, D. Schrader, M. Lorenzen, M. Dargatz and D. Holz. High-resolution tensor MR elastography for breast tumour detection. Phys Med Biol (2000) 45(6): 1649-1664.

Wang, Y. X., M. Halks-Miller, R. Vergona, M.E. Sullivan, R. Fitch, C. Mallari, B . Martin-McNulty, V. da Cunha, A. Freay, G.M. Rubanyi and K. Kauser. Increased aortic stiffness assessed by pulse wave velocity in apolipoprotein E-deficient mice. Am J Physiol Hart Circ Physiol (2000) 278(2): H428-34.
Sandrin, L., S. Catheline, M. Tanter, X. Hennequin and M. Fink. Time-resolved pulsed elastography with ultrafast ultrasonic imaging. Ultrason Imaging (1999) 21(4): 259-72.
Cutnell, J. and W. Kenneth (1998). Physics, Fourth Edition. New York. Table of Contents.
Heimdal, A., A. Stoylen, H. Torp and T. Skjaerpe. Real-time strain rate imaging of the left ventricle by ultrasound. J Am Soc Echocardiog (1998) 11(11): 1013-1019.
Konofagou E.E. and Ophir, J. (1998) A New Elastographic Method for Estimation and Imaging of Lateral Strains, Corrected Axial Strains and Poison's Ratios in Tissues, Ultrasound in Medicine and Biology 24(8), 1183-1199.
Konofagou E.E., Kallel F. and Ophir, J., (1998) Three-dimensional Motion estimation in Elastography, IEEE Proceedings of the Symposium of Ultrasonics, Ferroelectrics and Frequency Control in Sendai, Japan, 1745-1748.
Nichols, W. and M.F. O' Rourke (1998). Vascular impedance.In McDonald's:blood flow in arteries: theoretical, experimental and clinical principles. E. Arnold. London. Table of Contents.
Sarvazyan, A.P., O.V. Rudenko, S.D. Swanson, J.B. Fowlkes and S.Y. Emelianov. Shear wave elasticity imaging: A new ultrasonic technology of medical diagnostics. Ultrasound Med Biol (1998) 24(9): 1419-1435.
Spach, M.S., Heidlage, J.F., Dolber, P.C., and Barr, R.C. (1998). Extracellular discontinuities in cardiac muscle—Evidence for capillary effects on the action potential foot. Circulation Research 83, 1144-1164.
Brooks, D.H., and MacLeod, R.S. (1997). Electrical imaging of the heart. Ieee Signal Processing Magazine 14, 24-42.
Sutherland, G.R. Color Doppler Myocardial Imaging—Potential Applications in Acquired and Congenital Heart-Disease. Acta Paediatr (1955) 84: 40-48.
Walker, W.F. and G.E. Trahey. A Fundamental Limit on Delay Estimation Using Partially Correlated Speckle Signals. Ieee T Ultrason Ferr (1955) 42(2): 301-308.
Gupta, K.B., Ratcliffe, M.B., Fallert, M.A., Edmunds, L.H., and Bogen, D.K. (1994). Changes in Passive Mechanical Stiffness of Myocardial Tissue with Aneurysm Formation. Circulation 89, 2315-2326.
Fung, Y.C. (1993). Biomechanics—Mechanical Properties of Living Tissues. New York. Table of Contents.
Kanai, H., H. Satoh, K. Hirose and N. Chubachi. A New Method for Measuring Small Local Vibrations in the Heart Using Ultrasound. Ieee T. Bio-Med Eng (1993) 40(12): 1233-1242.
Zerhouni, E.A., D.M. Parish, W.J. Rogers, A. Yang and E.P. Shapiro. Human heart: tagging with MR imaging—a method for noninvasive assessment of myocardial motion. Radiology (1988) 169(1): 59-63.
Bonnefous, O. and P. Pesque. Time domain formulation of pluse—Doppler ultrasound and blood velocity estimation by cross correlation. Ultrason Imaging (1986) 8(2): 73-85.
Avolio, A.P., S.G. Chen, R.P. Wang, C.L. Zhang, M.F. Li and M.F. O'Rourke. Effects of aging on changing arterial compliance and left ventricular load in a northern Chinese urban community. Circulation (1983) 68(1): 50-8.
Edwards, C.H., Rankin, J.S., Mchale, P.A., Ling, D., and Anderson, R.W. (1981). Effects of Ischemia on Left-Ventricular Regional Function in the Conscious Dog. American Journal of Physiology 240, H413-H420.
Henderson, A., Parmley, W.W., and Sonnenbl, E. (1971). Series Elasticity of Heart Muscle During Hypoxia. Cardiovascular Research 5, 10-14.
Konofagou E.E., D'Hooge J.D., Ophir, J. Myocardial Elastography—Feasibility Study in Vivo. Ultrasound Med & Biol., vol. 28, No. 4, pp. 475-482 (2002).

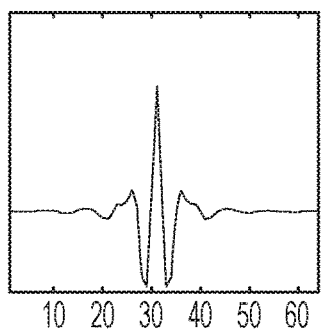 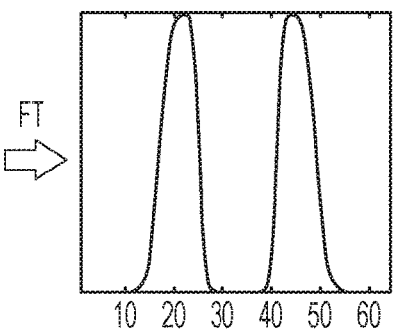 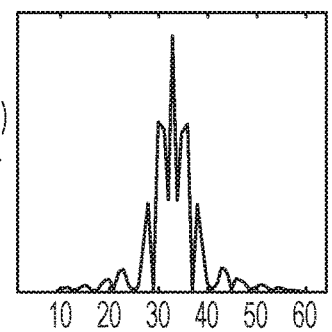
Fig. 9A    Fig. 9B    Fig. 9C
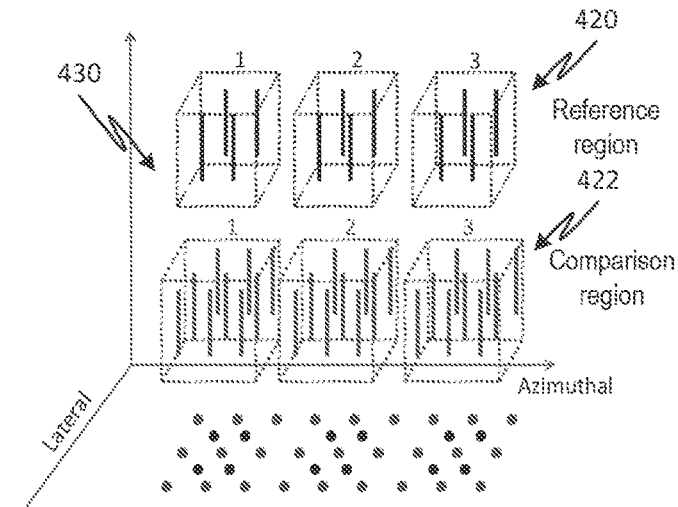
Fig. 12A
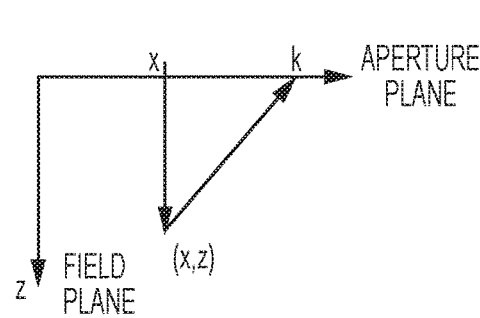
Fig. 10
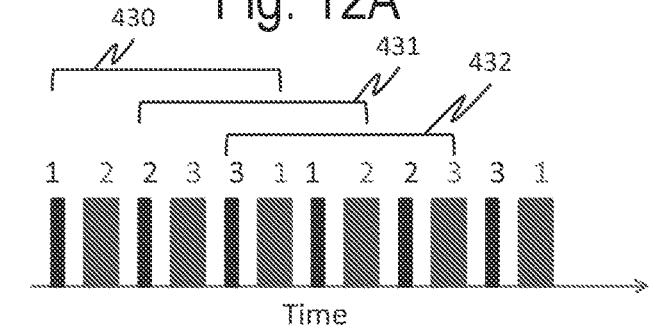
Fig. 12B
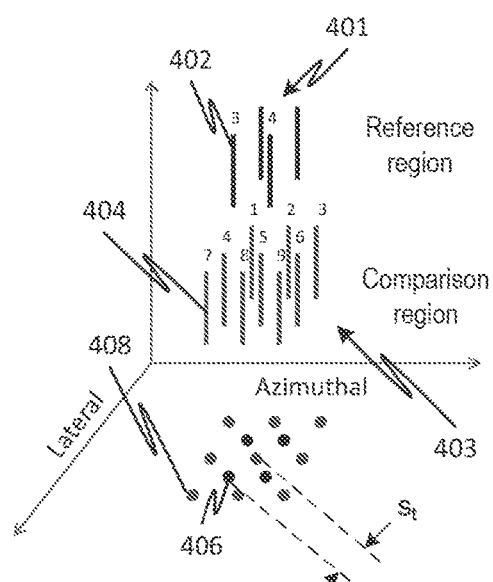
Fig. 11A
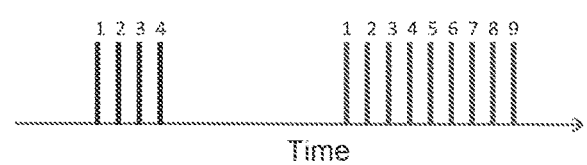
Fig. 11B

| # sectors | transmits per sector | MER |
|---|---|---|
| 1* | 12 | 65 |
| 1 | 12 | 272 |
| 2 | 6 | 544 |
| 3 | 4 | 897 |
Table 1: TUAS sector sizes and corresponding MERs. * indicates that motion estimation was performed over motion sampling intervals, allowing a lower MER to be achieved.
Fig. 36
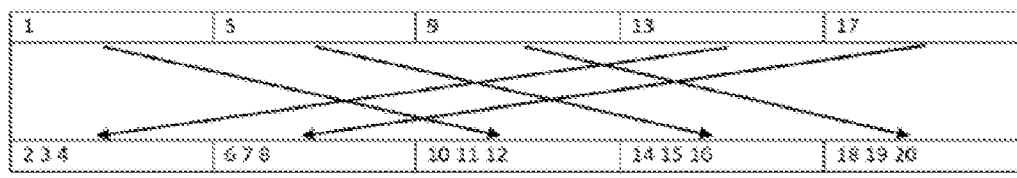
Fig. 37
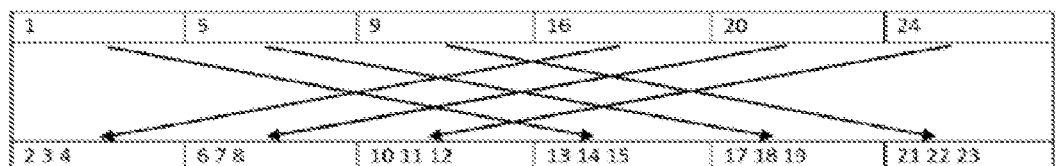
Fig. 38

ULTRASOUND DEVICES METHODS AND SYSTEMS

CROSS REFERENCE TO RELATED APPLICATIONS

This application is a divisional application of U.S. patent application Ser. No. 14/057,685, filed 18 Oct. 2013, which is a continuation in part of PCT/US12/35685, filed 27 Apr. 2012, which claims the benefit of U.S. Provisional Applications 61/500,858 filed 24 Jun. 2011; 61/504,687 filed 5 Jul. 2011; 61/532,266 filed 8 Sep. 2011; and 61/479,806 filed 27 Apr. 2011, each of which is hereby incorporated by reference in its entirety herein. This application is also a continuation in part of PCT/US12/34136, filed 18 Apr. 2012, which claims the benefit of U.S. Provisional Application 61/476,573, filed 18 Apr. 2011, each of which is hereby incorporated by reference in its entirety herein.

STATEMENT REGARDING FEDERALLY SPONSORED RESEARCH

This invention was made with government support under EB006042 and HL096094 awarded by the National Institutes of Health (NIH). The government has certain rights in the invention.

BACKGROUND

Electromechanical Wave Imaging (EWI) is an entirely non-invasive, ultrasound-based imaging method capable of mapping the electromechanical wave (EW) in vivo, i.e., the transient deformations occurring in response to the electrical activation of the heart. Achieving the optimal imaging frame rates necessary to capture the EW in a full-view of the heart poses a technical challenge due to the limitations of conventional imaging sequences, in which the frame rate is low and tied to the imaging parameters. To achieve higher frame rates, EWI is typically performed in multiple small regions of interest acquired over separate heartbeats which are then combined into one view. Yet, the frame rates achieved remain sub-optimal, because they are tied to the imaging parameters rather than being optimized to image the EW. More importantly, the reliance on multiple heartbeats precluded the study from application in non-periodic arrhythmias such as fibrillation.

Acoustic radiation force has been used to induce motion in living tissue to allow the non-invasive characterization of tissue properties in a live host. In U.S. Patent Publication No. 2007/0276242 to Konofagou, which is incorporated herein by reference as if set forth in its entirety herein, Konofagou describes systems, methods and apparatus which are used to focus ultrasound in a selected volume of tissue remote from an externally applied transducer to generate motion in the tissue. The techniques and devices of this reference may be employed in the new subject matter described in the disclosure below.

Tissue engineering methods devices and system that employ hydrogels incorporating microbubbles have been described in PCT Patent Publication No. WO 2011/028690 (PCT/US2010/047263) to Borden, et al., which is incorporated herein by reference as if set forth in its entirety herein. In this application, Borden, et al., describe tissue scaffolds with microbubbles and seeded with cells. The bubbles may be gas-filled to alter the mechanical properties of the tissue scaffold, for example, by making it compressible. Also, the microbubbles can ameliorate the movement (as by diffusion) of fluids such as perfusate through the tissue scaffold. Microbubbles of a suitable form are described in PCT/US2010/047263.

Tissue engineering requires the cultivation and development of cells in realistic environments. For example, some kinds of tissues may require mechanical stimulation or signaling in order to develop properly. Also, thick three-dimensional structures may make it difficult for chemical signaling and nutrient perfusion.

SUMMARY

The disclosed subject matter relates to the use of ultrasound for extracting spatio-temporal data from living tissue or other moving and/or deforming targets that can be imaged using ultrasound. This includes solid and liquid materials, for example, muscle tissue and blood. In embodiments, the disclosed subject matter, outgoing ultrasound energy is directed according to non-sequential patterns that permit different tradeoffs between temporal and spatial resolution of a target material. For example, an overall frame rate of a scan of an angular region can be reduced in order to generate brief delays between multiple (e.g., 2) scan lines in a particular, or each, region of a scan which are delayed by a selected interval that is less than the overall frame rate and then using cross correlation of the regions to extract high frequency motion information while obtaining lower rate motion and spatial information from the aggregate of the region scans. Other embodiments produce different tradeoffs.

A temporally-unequispaced acquisition sequence (TUAS) is described for which a wide range of frame rates are achievable independently of the imaging parameters, while maintaining a full view of the heart at high beam density. TUAS is first used to determine the optimal frame rate for EWI in a paced canine heart in vivo. The feasibility of performing single-heartbeat EWI during ventricular fibrillation is then demonstrated. These results indicate that EWI can be performed optimally, within a single heartbeat, and implemented in real time for periodic and non-periodic cardiac events. Other applications for high speed imaging, motion estimation, high frame rate imaging, and property determination exist with different emphases on the combination of a need for speed and spatial resolution. Spatially unequispaced embodiments are also described.

Objects and advantages of embodiments of the disclosed subject matter will become apparent from the following description when considered in conjunction with the accompanying drawings. The Summary is not intended to summarize all the disclosed or claimed subject matter.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 9A, 9B, and 9C are for describing apodization function features.

FIG. 10 illustrates axis conventions for describing experiments.

FIGS. 11A and 11B describe embodiments for imaging and motion estimation in 1D, 2D, and 3D with features for non-axial motion estimation.

FIGS. 12A and 12B describe further embodiments for imaging and motion estimation in 1D, 2D, and 3D with features for non-axial motion estimation.

FIG. 36 lists the sector sizes used in Example 1 and the corresponding MERs.

FIGS. 37 and 38 show the process of maximizing the distance between one principal line and the block of its sector while fulfilling a predefined constraint.

DETAILED DESCRIPTION OF THE EMBODIMENTS

Figure 1A:
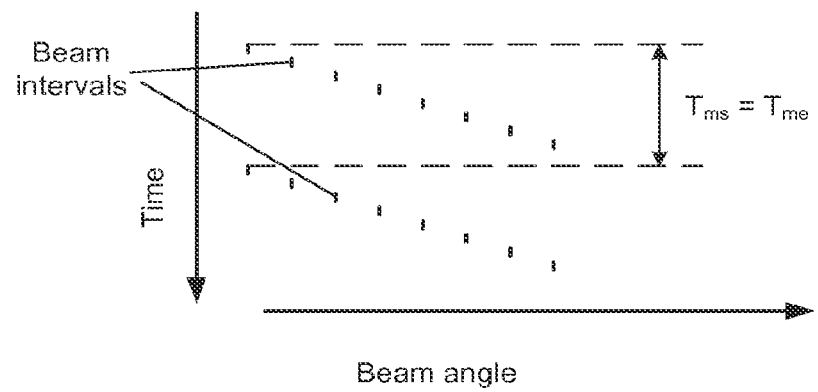
FIG. 1A shows a conventional imaging sequence according to the prior art.

Electromechanical Wave Imaging (EWI) is a non-invasive ultrasound-based imaging method that can map the transient deformations of the myocardium resulting from local electrical activation, i.e., the electromechanical wave (EW). The EW and electrical activation maps have been shown to be closely correlated, therefore indicating that EWI could become a low-cost, non-invasive, and real-time modality for the characterization of arrhythmias. EWI is a target application for the disclosed technology, but it can be used for other purposes as well. For purposes of describing the technology, EWI will be emphasized, however.

In EWI, inter-frame motion (or, displacement) may be estimated via cross-correlation of consecutive RF frames. From the displacements, the inter-frame strains (or, strains) depicting the EW may be generated by applying gradient operators on the displacement field. However, the heart is an organ that undergoes significant three-dimensional motion and large deformations, which both may lead to decorrelation of the RF signals and thus to the degradation of the motion and deformation estimation accuracy. To overcome this difficulty, the present embodiments adapt the time resolution of the motion estimation. For example the time lapse between frames may be optimized against the need for spatial resolution to prevent decorrelation from compromising the motion estimation. Short intervals covering a short interval may lie below the sensitivity of the motion estimator.

The present application describes validated methods, devices, and systems for capturing high speed motion over a large field of view. In embodiments, accurate motion estimation and anatomy are captured without reliance on cyclical repetition, such as cardiac cycles. Further, in embodiments, the capture is effective for evaluation of electromechanical wave propagation and distinguishing anomalies therein, particularly for the purpose of diagnosis and responsive medical treatment. The non-reliance on cyclical repetition allows the characterization of anomalies like arrhythmia and/or avoiding the need for patients to hold their breath during multiple cardiac cycles.

EWI maps the transient inter-frame strains (referred to here as 'strains' for brevity) occurring in the vicinity of the electrical activation of the heart. At the tissue level, the depolarization of myocardial regions triggers the electromechanical activation, i.e., the first time, at which the muscle transitions from a relaxation to a contraction state. Spatially, this electromechanical activation forms the EW front that follows the propagation pattern of the electrical activation sequence.

In embodiments, temporally-unequispaced acquisition sequence (TUAS) is used to acquire images of muscle deformation such as EW. In embodiments, TUAS employs sector-based sequence adapted to optimally estimate cardiac deformations. The TUAS was verified by an embodiment implemented on a conventional clinical ultrasound scanner. The embodiments of TUAS cover the simultaneous provision of a wide range of frame rates for motion estimation, high beam density for high resolution, and a large field of view in a single motion cycle, e.g., heartbeat. For a given set of imaging parameters, motion can be estimated at frame rates varying from a few Hz to kHz. To achieve this, the sampling rate of the motion estimation is reduced, as shown, such that there is little effect on the accuracy of EW maps. This is accomplished, in embodiments, by maintaining the sampling rate above a threshold selected for the target motion information.

In the TUAS embodiments, a wide range of frame rates can be achieved, including very high frame rates, independently of other imaging parameters. By maintaining a set of imaging parameters (e.g., field of view, imaging depth), the frame rate is selected responsively to the elastographic signal-to-noise ratio ($SNR_e$) and the EW. A probabilistic framework based on experimental data, acquired in a paced canine in vivo, was used to establish the technique for selecting an optimal frame rate. The single-heartbeat EWI at the optimal frame rate was used to study the electromechanical activity of fibrillation, a non-periodic arrhythmia.

In the study, which was approved by the Institutional Animal Care and Use Committee of Columbia University, a male mongrel dog, 18 kg in weight, was anesthetized with an intravenous injection of Diazepam 0.5-1.0 mg/kg IV as premedication, and Methohexital 4-11 mg/kg IV as induction anesthetic. It was mechanically ventilated with a rate- and volume-regulated ventilator on a mixture of oxygen and titrated isoflurane (0.5%-5.0%). Morphine (0.15 mg/kg, epidural) was administered before surgery, and lidocaine (50 micrograms/kg/h, intravenous) was used during the entire procedure.

To maintain blood volume, 0.9% saline solution was administered intravenously at 5 mL/kg/h. Standard limb leads were placed for surface electrocardiogram (ECG) monitoring. Oxygen saturation of the blood and peripheral blood pressure were monitored throughout the experiment. The chest was opened by lateral thoracotomy using electrocautery. Three pacing electrodes were sutured at the basal region of the lateral wall, at the left ventricular apex and at the right ventricular apex. Only one pacing electrode, located at the basal region of the lateral wall, was used to pace the heart in certain evaluation experiments. RF ablation of the left bundle branch was performed under fluoroscopy and a basket catheter (Boston Scientific, Natick, Mass.) was introduced in the left ventricle for the purpose of another study.

The motion-estimation rate $r_{me}$ is defined as the inverse of the time, i.e., $T_{me}$, lapsing between the two RF frames used to estimate motion. The motion-sampling rate $r_{ms}$ is defined as the inverse of the time, i.e., $T_{ms}$, lapsing between two consecutive displacement maps. In conventional imaging sequences, these two rates are equal, because a given frame is typically used for two motion estimations. Commonly an ultrasound image is constructed using a phased array to acquire a number of beams, typically 64 or 128, over a 90° angle. FIG. 1A illustrates the conventional scheme showing a simplified scheme with only a few beams repeated over two cycles for purpose of discussion. In FIG. 1A, the beams are acquired sequentially, and the process is repeated for each frame with each frame separated by an interval $T_{me}=T_{ms}$. The motion estimation interval ($T_{me}$) is defined as the inverse of the inter frame rate used to estimate motion, whereas the motion sampling interval ($T_{ms}$) is defined as the inverse of the displacement frame rate. That is, full frames are obtained and the motion estimated by cross-correlation of the images using known techniques. For example, a given beam angle will be repeated at a fixed interval $T_{me}=T_{ms}$.

Figure 1B:
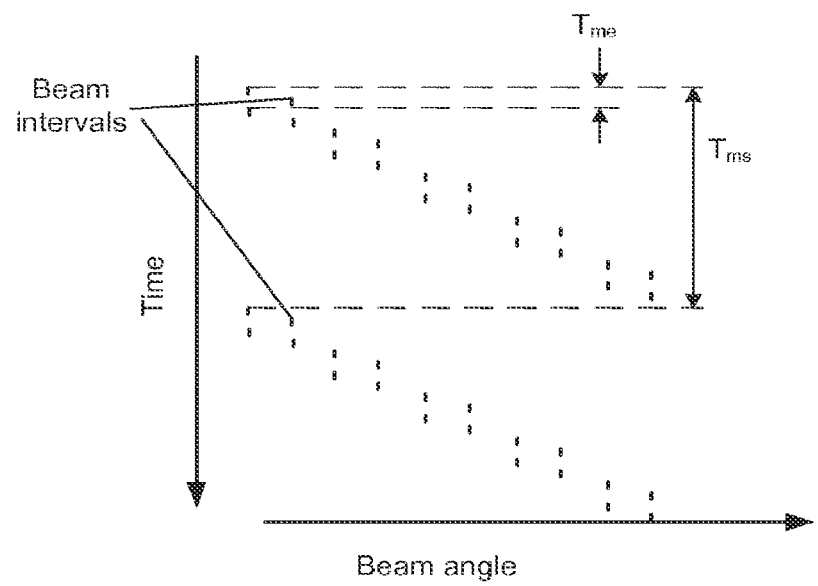
FIG. 1B shows a temporally unequispaced sequence according to an embodiment of the disclosed subject matter in which a displacement estimation is done between two RF lines separated by a first time interval and displacement estimations by a second interval that is greater than, and independent of, the first interval.

In some TUAS embodiments, the motion-estimation rate and the motion-sampling rate are different so that $T_{me} \neq T_{ms}$. In TUAS, the motion-estimation rate is selected independently of the sampling rate. As shown in FIG. 1B, only a fraction of the entire frame is scanned before the fraction is scanned again so that a fractional sector of the full 90 degree frame is scanned twice before the next sector (in the illustration there are only two beams at respective angles per a sector). A frame in the TUAS case provides motion estimation, thus drastically reducing the motion-sampling interval relative to the conventional method and thereby increasing the temporal resolution used for motion estimation. In the TUAS embodiments similar to that of FIG. 1B, the number of angles per sector can be varied to generate different ratios of $T_{me}$ to $T_{ms}$.

An acquisition performed at a 12-cm-depth with 64 beams with a conventional sequence may correspond to a frame rate of 100 Hz. However, while 100 Hz may suffice to satisfy the Nyquist sampling criterion of cardiac motion, it is, as described below, insufficient for accurate motion tracking using RF cross-correlation. Therefore, to reach a higher frame rate of, e.g., 400 Hz typically used for EWI, the conventional approach would be to divide the number of beams by four, and thereby reduce either the lateral resolution, the field of view, or both. At the same depth and beam density, TUAS provides a motion-sampling rate of 50 Hz and a motion-estimation rate that can be varied, as shown in the following section, within the following group: {6416, 3208, 1604, 802, 401, 201, 100} Hz. This has numerous advantages. For example, both the lateral resolution and the field of view can be maintained while estimating the cardiac motion with an optimal frame rate, which could be, for example, 401 or 802 Hz, depending on the amplitude of the cardiac motion. This results in a halving of the motion-sampling rate. However, the motion-sampling rate has little effect on the motion estimation accuracy. If this rate remains above the Nyquist rate of the estimated cardiac motion, this will have no effect.

Figure 2:
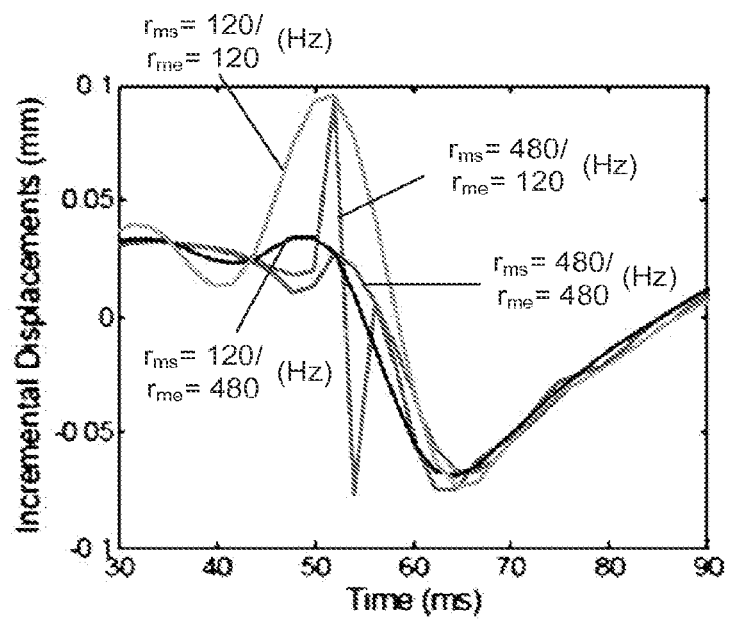
FIG. 2 shows a comparison of a high strain, high rate interval of an EWI scan for comparing motion estimate at different frame and motion estimation parameters.

To estimate the effects of the motion-sampling rate on the accuracy of the motion estimation, RF data acquired over multiple heartbeats at 480 Hz from a previous study was decimated to vary the motion-estimation and motion-sampling rates. At the scale of the full cardiac cycle, both rates have little influence on the general trend of the displacements but as shown in FIG. 2, during fast transients deformations, e.g., during the electrical activation, larger differences were observed. These larger differences also correspond to higher strain values than e.g., during end-systole. For a fixed motion-sampling rate, dividing the motion-estimation rate by four, leads to an error of approximately 100% in the displacements. However, when dividing the motion-sampling rate by four while maintaining a high motion-estimation rate, only small variations are observed in the incremental displacements. From experiments, it is estimated that at a motion-sampling rate above 120 Hz, the significance of the motion-sampling rate became negligible compared to the effect of the motion-estimation rate.

In a conventional imaging sequence, two consecutive frames with N beams per frame are acquired beam by beam in sequence resulting in a time between two frames of 2dN/c, where d is the imaging depth, N is the number of beams in the image, and c is the speed of sound. Motion is then estimated between the two consecutive acquisitions of beams at the same location. For example, motion is estimated through the cross-correlation of beam 1 acquired at time 1 and beam 1 acquired at time N+1. Therefore, identical motion estimation and motion sampling rates are obtained, equal to $c(2dN)^{-1}$.

Figure 3:
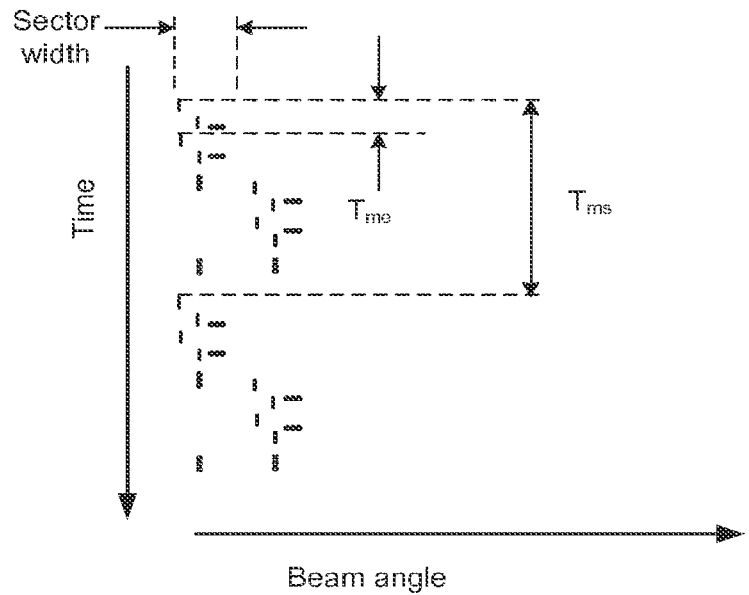
FIG. 3 shows a class of TUAS schemes in which a scan is performed sector by sector at intervals chosen responsively to the predicted motion (e.g. strain) rate of change in a target tissue.

TUAS was implemented in an open-architecture Ultrasonix MDP system (Ultrasonix Corp, Burnaby, BC, Canada) using the Texo Software Development Kit. In TUAS, the beams constituting two frames are acquired in a different order. Beams are acquired consecutively within sectors containing k beams, and then repeated. In FIG. 3 the k beams may be repeated twice for two sector-sized mini-frames for motion estimation. Alternatively, there may be more than two sector-sized mini-frames to obtain two inter-mini frame motion estimates which may be stored separately with respective times or averaged to form a single motion estimate for the sector. The number of beams comprising a sector is labeled "sector width" (angular spacing of adjacent beams multiplied by the number of beams per sector k) assuming a regular spacing of the beams in a sector. The time interval between mini-frames of a single sector is indicated as $T_{me}$. The time interval between frames of the entire regular frame is indicated as $T_{ms}$. Note that the beams per sector can be varied between sectors or the spacing between beams in a sector or among different sectors can be different. Note that k can be equal to one up to a fraction of the total beams per global frame.

Axial motion is estimated between two beams acquired consecutively at the same location, which results in a motion estimation rate of $c(2dk)^{-1}$. Since k needs to be a divisor of N, i.e., div(N), the group of available motion-estimation rates for a given number of beams is given by $c(2d)^{-1}\{(div(N))^{-1}\}$. The highest motion estimation rate occurs at k=1, i.e., $c(2d)^{-1}$, and the lowest motion estimation rate occurs at k=N, and is equal to that of a conventional imaging sequence, i.e., $c(2dN)^{-1}$. If motion is estimated only between the two closest acquisitions of the same beam in time, the motion-sampling rate is $c(4dN)^{-1}$. Note that in addition to motion being estimated between beams separated by $T_{me}$, lower motion-estimation rates can also be achieved by estimating motion between beams separated by $T_{ms}$-$T_{me}$ (See FIGS. 1A, 1B, and FIG. 3 and attending discussion), corresponding to a motion-estimation rate of $c(2d(N-k))^{-1}$, in which case the motion-sampling rate would be $c(2dN)^{-1}$.

A 3.3-MHz phased array was used to image the myocardium in vivo. Axial displacements were estimated using a 1D cross correlation algorithm using RF signals sampled at 20 MHz. The window size used was 4.60 mm and the overlap 90%. The heart was segmented using an automated contour tracking technique. The incremental axial strains were estimated with a least-squares method and a kernel size of 10.7 mm. Images were acquired at different motion-estimation rates, i.e., {41, 82, 163, 350, 452, 855, 1100, 1283, 1540} Hz and their corresponding motion-sampling rates {163, 163, 163, 163, 211, 132, 128, 119, 119} at a 10-cm depth.

To assess the accuracy of a strain measurement, the $SNR_e$ was used, which is defined as:

$$SNR_e = \frac{\mu}{\sigma}, \tag{1}$$

where μ is the local average of strains ε at a given time, and σ the corresponding standard deviation. In experiments, the $SNR_e$ at different motion-estimation rates was computed by averaging and calculating the standard deviation of the incremental strains within an axial window of 4.85 mm for individual pixels over multiple frames, corresponding to up to 5 heart cycles, after segmenting the heart. This provides the $SNR_e$ as a function of space and time, $SNR_e(x,y,t)$ where x and y are the lateral and axial directions, respectively and t is the time. Previous literature on the strain-filter indicates that the $SNR_e$ will depend mostly on the value of the strains to be measured, when the imaging parameters are fixed. This theoretical framework allows the construction of an upper limit on the $SNR_e$ as a function of the strain amplitude (a.k.a., the strain-filter). The strain filter corresponds, in this case, to the Ziv-Zakai Lower Bound (ZZLB) on the variance. The ZZLB is a combination of the Cramér-Rao Lower Bound (CRLB) and the Barankin bound (BB). The ZZLB transitions from the CRLB to the BB when decorrelation becomes important to the point that only the envelope of the signal contains information on the motion. In the correlation model used here, this transition occurs only at very large strains. The strain filter was adapted to the imaging parameters used in this study as a reference. For that purpose, the RF data SNR of 1500 (60 dB) was assumed, similar to what was previously considered in prior literature. Such a high value is justified since acquisition was performed in an open-chest setting.

The motion-estimation rate is directly linked to the strain distribution in the heart. Consider the cumulative strain function at a given point $(x_o, y_o)$, $e(x_o, y_o, t) = e(t)$. Then, the strain at a time to can be defined as $$\varepsilon(t_0) = e(t_0 + T_{me}) - e(t_0) \qquad (2)$$

When expanding e(t) in Taylor series around to, the result is $$\varepsilon(t_0) = e(t_0) + e'(t_0)(T_{me} + t_0 - t_0) - [e(t_0) + e'(t_0)(t_0 - t_0)] + O(T_{me}^2) \qquad (3)$$

$$= e'(t_0)(T_{me}) + O(T_{me}^2)$$

$$\approx \frac{e'(t_0)}{r_{me}},$$

where $e'(t_0)$ is the strain rate, and is independent of the motion-estimation rate $r_{me}$. Let consider the same heart with two strain distributions acquired at a rate $r_{me1}$ and $r_{me2}$ comprised in $\varepsilon_1 \pm \Delta\varepsilon_1$ and $\varepsilon_2 \pm \Delta\varepsilon_2$. Then, $$\varepsilon_2 \pm \Delta\varepsilon_2 \approx \frac{r_{me1}}{r_{me2}}(\varepsilon_1 \pm \Delta\varepsilon_1) = \left(\frac{r_{me1}}{r_{me2}}\varepsilon_1 \pm \frac{r_{me1}}{r_{me2}}\Delta\varepsilon_1\right) \qquad (4)$$

Therefore, if $r_{me2} = 2r_{me1}$, $\varepsilon_2 \pm \Delta\varepsilon_2 = \varepsilon_1/2 \pm \Delta\varepsilon_1/2$. In other words, when doubling the motion-estimation rate, both the center and width of the strain distribution are halved. Finding the optimal motion-estimation rate is thus equivalent to finding the optimal strain distribution.

To perform this optimization, the probability of obtaining a $SNR_e$ value is determined within a given interval, e.g., $[s_1, s_2]$, for a given strain $\varepsilon_0$, i.e., in a probabilistic framework, $P(s_1 < SNR_e < s_2 | \varepsilon = \varepsilon_0)$. $SNR_e$ and $\varepsilon$ are simultaneously measured. As a result, their two-dimensional histogram can be constructed and used to determine their joint probability density function (pdf), i.e., $f(SNR_e, \varepsilon)$. The individual pdf of SNRe and $\varepsilon$ can also be obtained from 1-D histograms. Finally, the conditional pdf $f(SNR_e | \varepsilon)$ can be obtained through the following relationship:

$$f(SNR_e \mid \varepsilon) = \frac{f(SNR_e, \varepsilon)}{f(\varepsilon)}, \qquad (5)$$

Note that $f(SNR_e)$, $f(SNR_e, \varepsilon)$ and $f(SNR_e | \varepsilon)$ also depend on the motion-estimation rate, $r_{me}$, and on the temporal portion of the heart cycle of interest, $\Delta t_e$, i.e., $$f(SNR_e \mid \varepsilon; r_{me}, \Delta t_c) = \frac{f(SNR_e, \varepsilon; r_{me}, \Delta t_c)}{f(\varepsilon; r_{me}, \Delta t_c)} \qquad (6)$$

The analysis below is based on assumptions a and b:
a) $f(SNR_e | r_{ME}, \Delta t_c) = f(SNR_e | \varepsilon; r_{ME})$, i.e., the relationship linking $SNR_e$ and $\varepsilon$ does not explicitly depend on the cardiac phase. For example, a 1% strain occurring during systole will lead to the same $SNR_e$ distribution as a 1% strain occurring during diastole.
b) $f(SNRe | \varepsilon; r_{ME}) = f(SNRe | \varepsilon)$, i.e., the relationship linking SNRe and $\varepsilon$ does not explicitly depend on the motion-estimation rate. For example, a 1% strain measured with a motion-estimation rate of 1500 Hz will lead to the same $SNR_e$ distribution than a 1% strain measured at 400 Hz. This assumption is stronger than a). Effectively, theoretical models of the correlation coefficient typically rely, for fixed imaging parameters, only on the strain value, which would support assumption b). However, in the heart, the decorrelation effect of out-of-beam motion might be important. In such a case, a high motion-estimation rate would reduce decorrelation caused by out-of-beam motion in comparison with a lower motion-estimation rate and thus modify the relationship between $SNR_e$ and $\varepsilon$.

Finally, the expected value of the SNRe was obtained as follows:

$$E\{SNR_e; r_{me}, \Delta t_c\} = \int_0^{+\infty} E\{SNR_e \mid \varepsilon; r_{me}\} f(\varepsilon; r_{me}, \Delta t_c) d\varepsilon, \qquad (7)$$

where the conditional expected value is given by $$E\{SNR_e \mid \varepsilon; r_{me}\} = \int_0^{+\infty} SNR_e f(SNR_e \mid \varepsilon; r_{me}) dSNR_e, \qquad (8)$$

under assumption (a).

This expected value of $SNR_e$ varies during the cardiac cycle, i.e. as a function of $\Delta t_c$, as indicated in eq. (7). Two strain distributions were constructed: $f(\varepsilon; r_{ME}, \Delta t_t)$ and $f(\varepsilon; r_{ME}, \Delta t_a)$ where $\Delta t_t$ and $\Delta t_a$ correspond to five cardiac cycles (approx. 3000 ms) and the 20 frames following the R-wave (approx. 100-170 ms), respectively. $f(\varepsilon; r_{ME}, \Delta t_t)$ was used to construct a robust conditional pdf, i.e., $f(SNR_e | \varepsilon; r_{ME})$, based on a large enough number of samples (approx. 300, 000) under assumption a). By averaging $f(SNR_e | \varepsilon; r_{ME})$ over all the motion-estimation rates, $f(SNR_e | \varepsilon)$ was obtained under assumption b).

Figure 4:
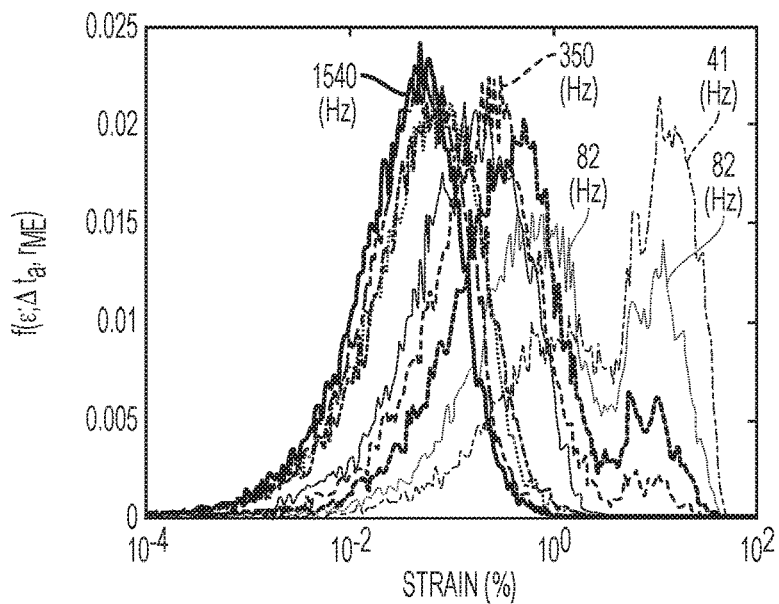
FIG. 4 shows a graph of strain distribution as a function of the motion-estimation rate during activation.

The strain distribution was found to have varied both during the cardiac cycle and at different motion-estimation rates. Analysis of the variation of the strain distribution as a function of the motion-estimation rate during activation indicates that at high motion-estimation rates, a bimodal distribution is obtained. A local minimum consistently occurs at an approximately 4% strain. This is in contradiction with eq. 4, which predicts a shift of that minimum. However, as the motion-estimation rate increases, the distribution translates towards lower strain values, narrows and becomes unimodal. As predicted by eq. 3, the center and width of the strain distribution decreases in $(r_{me})^{-1}$. These observations may be seen in FIG. 4.

Highly variable strain distributions as a function of time were observed, during the cardiac cycle both during pacing and during sinus rhythm (for the sinus rhythm case only, data was acquired in a different canine using the automatic composite technique). For example, high strain values were observed during the electrical activation (0-100 ms) and following repolarization (350-450 ms). During diastole, strain amplitudes vary greatly, i.e., from very high values (500-600 ms) to very low values (600-700 ms).

The probability of measuring a $SNR_e$ value simultaneously with a given strain value of (i.e., the joint pdf) was plotted. For low motion-estimation rates (41 Hz), the joint pdf spreads towards larger strain values and is associated with small values of $SNR_e$. At 452 Hz, the probability of higher $SNR_e$ values is higher, and located between 0.01% and 1% strains. At large motion-estimation rates (1540 Hz), the pdf is concentrated in lower strain values and lower $SNR_e$ values are more probable. These joint pdfs directly depend on the probability of measuring strain. As a result, if, for a given motion-estimation rate, the probability of measuring a given strain was low, the probability of measuring the $SNR_e$ associated with that strain value was also low. To normalize this effect, the conditional pdf was analyzed. In that case, the probability is normalized for each individual strain value. The different conditional pdfs obtained for different motion-estimation rates were very similar in overlapping domains at different motion-estimation rates, therefore indicating that assumption b) can be used. To obtain a complete representation of the conditional pdf, it was averaged over nine different motion-estimation rates. The $SNR_e$ remained below the CRLB, with the conditional expected $SNR_e$ value being approximately one order of magnitude lower. An experimental transition zone corresponding to a minimum observed at 4% strain was also added and corresponded to a sharp transition in the conditional pdf. For strains higher than 4%, the conditional pdf remained limited by the BB. The motion-estimation rates corresponding to the center of the strain distribution over 5 cardiac cycles and during activation only are also shown, by computing e'(to) in eq. (3). The average value of e'($t_0$) over five cardiac cycles, i.e., e'($\Delta t_c$), and during activation only, i.e., e'($\Delta t_a$), was 155.5 s$^{-1}$ and 389.1 s$^{-1}$, respectively. The same conditional pdf with the conditional expected value of the $SNR_e$ showed the peak conditional expected value of the $SNR_e$ is located between approximately 0.1% and 1% strain, which corresponds to 1555 and 155 Hz over 5 cardiac cycles, and to 3891 and 389 Hz during activation only, respectively.

Figure 5A:
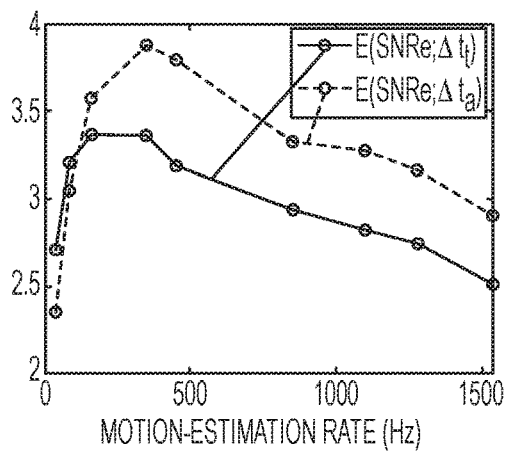
FIG. 5A is a plot of expected value of the $SNR_e$ as a function of the motion-estimation rate for five cardiac cycles and during activation.
Figure 5B:
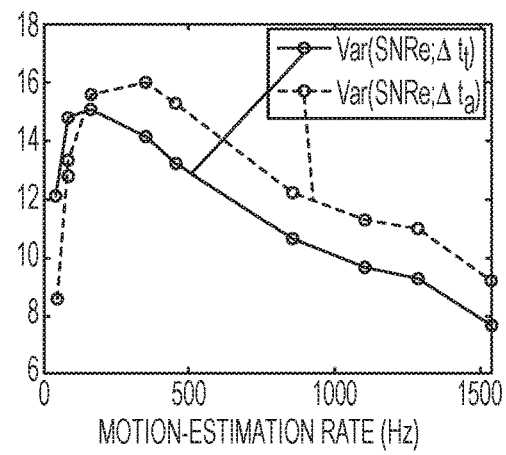
FIG. 5B is a plot of variance of the $SNR_e$ as a function of the motion-estimation rate for five cardiac cycles and during activation.
Figure 5C:
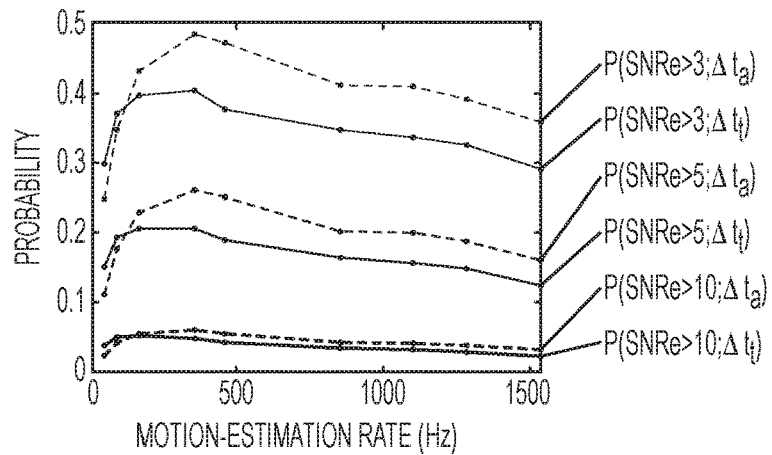
FIG. 5C is a plot of probability of obtaining a $SNR_e$ value higher than 3, 5 and 10 as a function of the motion-estimation rate for five cardiac cycles and during activation.

The expected value of the $SNR_e$ as a function of the motion-estimation rate was then obtained following eq. (7) for five cardiac cycles and during activation only (FIG. 5A). Note that unlike the conditional expected value shown in FIG. 4, the expected value encompasses an entire strain distribution. A sharp increase in the expected value of the $SNR_e$ is observed as the motion-estimation rate transitions from low values up to a maximum at 163 Hz and 350 Hz over five cardiac cycles and during activation only, respectively. The expected value of the $SNR_e$ then slowly decays with the motion-estimation rate. A similar behavior is observed in the variance of the $SNR_e$ (FIG. 5B): a maximum is achieved at 350 Hz that decays at higher motion-estimation rates. Finally, the probability of obtaining a $SNR_e$ value higher than 3, 5 and 10 was also explored (FIG. 5C). A maximum value also occurred at 350 Hz. For example, it is approximately twice as likely to obtain a $SNR_e$ higher than 3 at 350 Hz than at 41 Hz during activation.

The EW was imaged during a single heartbeat using TUAS in a full four-chamber view of a canine heart in an open-chest canine in vivo. Image frames were overlayed with color maps indicating the axial incremental strains. For example, the axial incremental strains may be shown for a sequence showing the EW imaged with a 1100 Hz motion estimation rate and a 137 Hz motion sampling rate. Such images showed features of the EW that are expected during pacing from the basal region of the lateral wall. In the parasternal four-chamber view, electrical activation results mostly in thickening of the myocardium; therefore, activation appears as a transition from thinning to thickening. The EW first appears in the basal region of the lateral wall, approximately 30 ms after pacing. The EW was initiated at the epicardium and traveled towards the endocardium of the lateral wall. Its average velocity over a region of 5 cm can be estimated to be approximately 1.0 m/s, which corresponds to the expected velocity of the electrical activation in the cardiac muscle. The image sequence indicated that the EW then propagated to the septum and then the right ventricle.

In embodiments, the time interval for estimating motion is selected responsively to the error sources captured by the foregoing analysis. In embodiments, the motion capture frequency is optimized to ensure a low random signal component and a low risk of distortion of the motion estimation resulting from strain (motion other than pure displacement).

Using TUAS, it is possible to image cardiac abnormalities that are not periodic, such as fibrillation and this was demonstrated. This was proved experimentally. After prolonged pacing, a heart underwent ventricular fibrillation. The heart was imaged with a motion-estimation rate of 2000 Hz. An acquisition was performed during 8 seconds. No, or very little, wall motion was observed on a B-mode image sequence. However, the incremental strains mapped depicted small, local and oscillating deformations. While pacing from the basal region of the lateral wall was maintained during fibrillation, no clear propagation was observed from the pacing origin.

In the experiments, a TUAS-based imaging sequence was developed and implemented in vivo. Such a method increases the motion-estimation rate at the cost of a lower motion-sampling rate, thus allowing very high frame rate motion estimation while maintaining a high lateral resolution and a full view of the heart. Using this technique, the optimal motion-estimation rate for EWI was obtained within a probabilistic framework. Finally, the feasibility of imaging non-periodic arrhythmias in a full field of view with a high motion-estimation rate is demonstrated.

To show the importance of optimally selecting the motion-estimation rate to perform accurate strain estimation, the $SNR_e$ was estimated in vivo in a paced canine, with a wide range of motion-estimation rates available with TUAS. Since the motion-estimation rate can be used as a means to translate and narrow the strain distribution, one can find the optimal value by studying the link between the strains and the $SNR_e$. By constructing first the joint pdf of the $SNR_e$ and the strains, the conditional pdf was obtained for every motion-estimation rate. By averaging these conditional pdf's, a combined conditional pdf spanning a large range of strains values was obtained. This combined pdf was in agreement with the strain-filter theory, which provides a higher bound on the $SNR_e$. Electronic noise at low strains values and decorrelation at high strain values prevented high $SNR_e$'s in these ranges. The ZZLB predicts a sharp transition between the CRLB and BB when decorrelation becomes important to the point that the phase of the signal does not contain information about motion. Using a model of correlation that takes into account only strains, this transition was expected to occur at 40% strains. However, the findings suggest that this transition occurs in the vicinity of 4% strains instead, indicating that other causes resulting in decorrelation such as out-of-beam motion have large consequences on the value of the $SNR_e$. It was confirmed that the combined conditional pdf is comprised within the CRLB up to approximately 4% before it becomes comprised within the BB. A sharp decrease in the expected value of the $SNR_e$ is also observed at 4% strain, underlying the importance of using the phase information of the RF signal for accurate strain measurements. It was also observed that the strain distribution lacked values around this transition. A distortion in the strain distribution may indicate that while a high $SNR_e$ can be maintained, the accuracy of the strain estimator is impaired at low motion-estimation rates, i.e., less than 350 Hz in this case. Four measures were used to determine the optimal motion-estimation rate: the expected value of the $SNR_e$ and the probability of obtaining a $SNR_e$ value larger than 3, 5 and 10. For all these measures, the optimal motion-estimation rate was found to be 350 Hz. However, 350 Hz also corresponded to the highest variance in the $SNR_e$. In other words, a motion-estimation rate of 350 Hz provides the highest SNRe but is also riskier, in the sense that the SNRe will not be homogeneous within one image. By increasing the motion-estimation rate further, the expected value of the $SNR_e$ decreases but so does the variance. Therefore, there is a trade-off between the expected value of the SNRe and the likelihood of obtaining this value.

These results are, however, tied to the context of this study. This validation was performed in an open-chest setting, which provides very good image quality with the ultrasound system used. In a more clinically-relevant transthoracic imaging, the signal-to-noise ratio of the RF signals themselves are expected to be lower, shifting the ZZLB towards higher strain values and thus modifying the optimal motion-estimation rate value. Inversely, in a context of higher RF signal-to-noise ratio such as in trans-esophageal echocardiography, the ZZLB may be expanded towards lower strains, thus improving the $SNR_e$ associated with higher motion-estimation rates. Because of the wide range of motion-estimation range available when using TUAS, an optimization process similar to the one developed here could be adjusted on an individual basis.

The effect of reducing the motion-sampling rate was also investigated. At motion-sampling rates of 120 Hz, it was found possible to depict the EW. This indicates that the motion-sampling rate can be reduced at very little cost in terms of motion estimation performance. The location of the activation was detected because of the high precision achieved for the motion estimation. This shows that the trade-off of TUAS, i.e., halving the sampling rate compared to a conventional sequence with the same beam density, does not jeopardize the EW depiction. Decoupling the two frame rates may thus be a solution to improving the precision of the axial estimation without sacrificing the lateral resolution.

It was shown that TUAS is capable of accurately depicting non-periodic events at high temporal resolution. Effectively, the ability to image the displacements and strains in a fibrillating canine heart, in a full-view and with high beam density, was demonstrated. Strain patterns expected during such a phenomenon were depicted, such as a disorganized contraction, leading to little-to-no large scale motion of the heart. Regions of the myocardium were oscillating rapidly from thinning to thickening and thickening to thinning over time. Studying the frequencies of these oscillations could be useful in understanding the mechanisms of fibrillation.

Various focusing patterns designed may be used to improve the motion estimation/spatial resolution trade-off. The following discusses embodiments which may be implemented in combination with composite imaging (combining samples from multiple repeating cycles) or TUAS.

A focused beam may be used as in a standard acquisition sequence in which the frame rate is increased by sending only a limited number of transmits and creating multiple lines per transmit as has been described with reference to FIGS. 1B and 3.

Figure 6A:
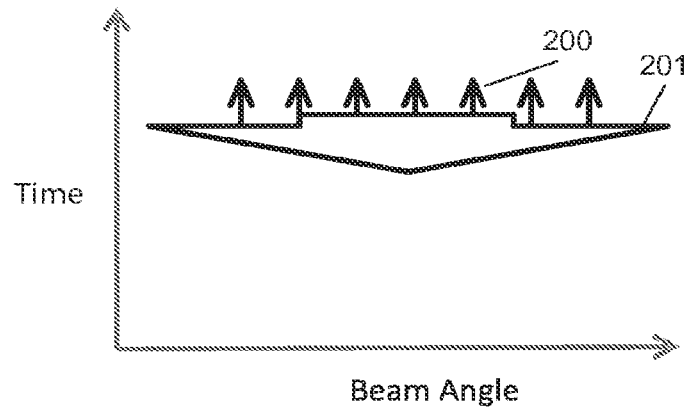
FIGS. 6A, 6B, and 6C illustrate embodiments employing, flash or plane wave imaging, which may increase the temporal resolution of displacement estimates in ultrasound scans.

Flash or plane wave mode (FIG. 6A) consists of sending non focused transmit waves 201. In this case, all the elements of the probe fire at the same time resulting in a wavefront parallel to the probe. An image is created from a single transmit event so that $FR=c/2d$ The flash (could also be plane wave—will use "flash" hereon for convenience) sequence may produce lower image quality since no focus is present. Also, the energy emitted is distributed over the field of view making this technique more sensitive to reflections from high-impedance tissues such as bones. A single flash pulse 201 may be emitted and receive beam forming used to generate receive beams 200. As is understood in the art, the receive beams may be used to create an image. The process is repeated to create an image sequence from which motion can be estimated.

Figure 6B:
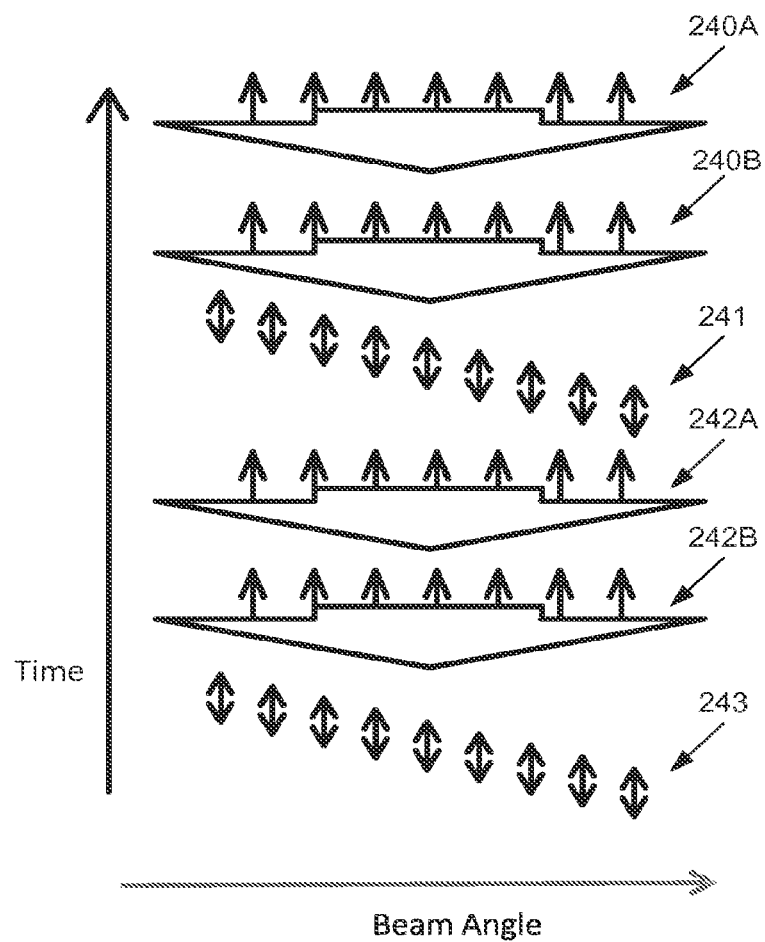
Figure 6C:
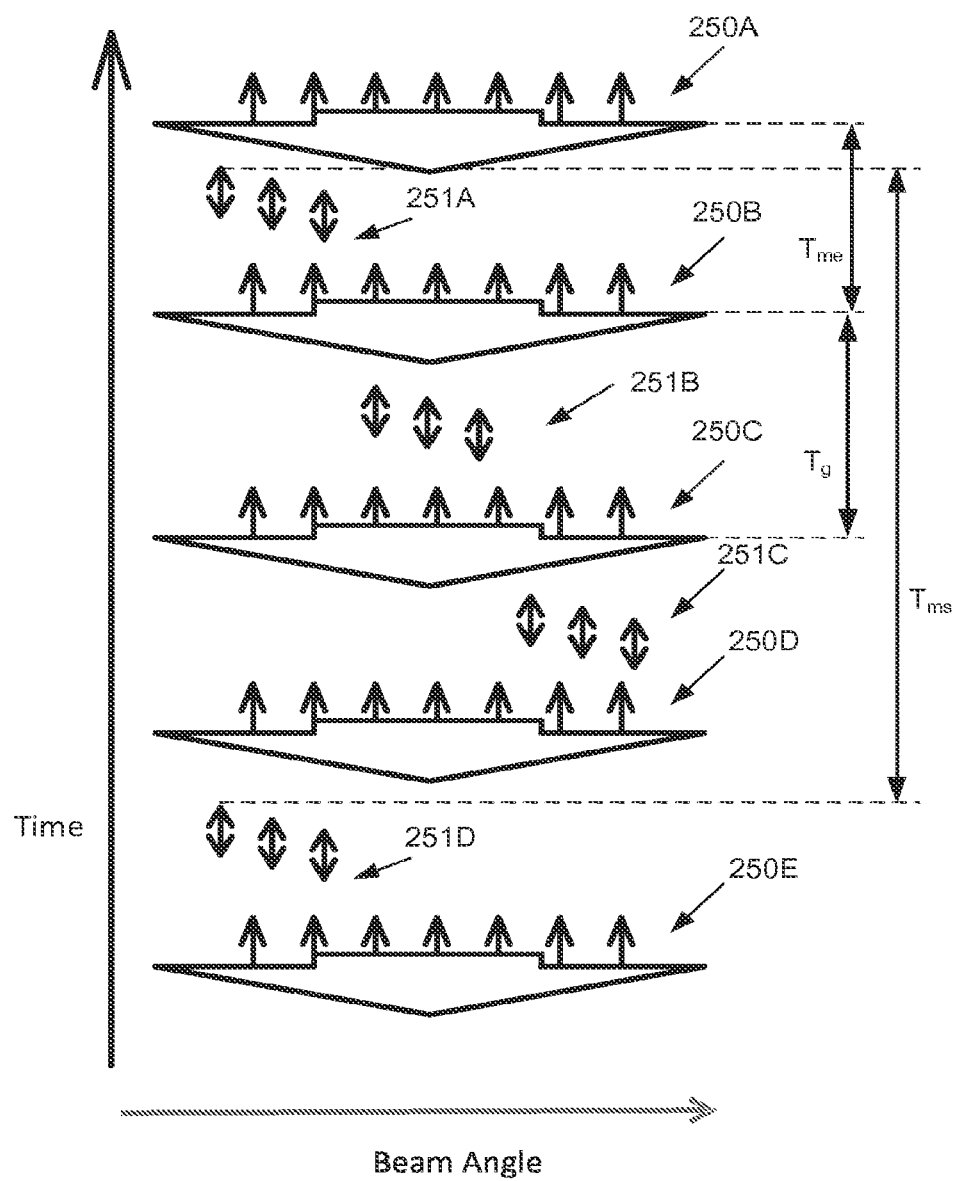

FIG. 6B illustrates a combination of flash mode image acquisition and conventional frame scanning (B-mode) image acquisition. The flash mode produces less resolution but fast motion estimation. So flash mode acquisition pairs 240A, 240B and 242A, 242B are used for high frequency motion estimation and further image frames are generated on a longer time base by conventional focused beams 241, 243. The pattern repeats for the duration of the scan. FIG. 6C shows that the temporal separation between the flash acquisitions and the conventional focused beam acquisitions is flexible in that the flash acquisitions 250A, 250B, 250C, 250D, 250E etc. can be temporally interspersed among the lines of the focused beams 251A, 251B, 251C 251D etc. The time gap $T_g$ between pairs of flash acquisitions may be varied independently. The focused beams 251A, 251B, 251C form a single image frame. The image frames provided by the focused beam image frames provide the detailed anatomical information and gross motion while the flash modes can provide motion estimation and these can be overlaid on an output display. It will be evident that a user may select the temporal spacing of the flash and focused beam acquisitions to permit the $T_{me}$ and $T_{ms}$ intervals to be substantially independently selected. The additional flash acquisitions may be combined with focused frame acquisitions to generate or improve the quality of interpolation frames as well as provide more frequent displacement estimations.

Figure 7A:
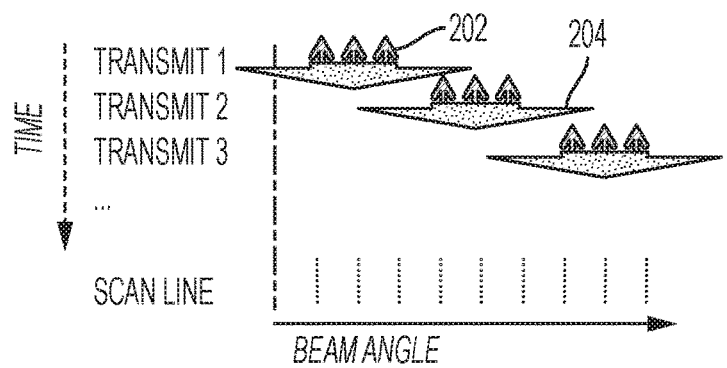
FIGS. 7A, 7B, and 7C illustrate embodiments, employing broad transmit beams, which may increase the temporal resolution of displacement estimates in ultrasound scans.

Partial defocusing or "Explososcan" lies between the standard and flash sequences. The size of the focus is increased making the formation of more than one line per transmit more efficient as illustrated in FIG. 7A. This may be done by appropriate beam forming or by using a Hanning window. Receive beam forming is used as indicated by the multiple return arrows 202 for each transmit event 204, i.e. less transmits are necessary to illuminate a given area. The size of the focus and the number of lines consequently formed can be varied as much as wanted. The size of the focus can be easily chosen by varying the size of the aperture. In this case, the drawback is also a reduced image quality since resolution becomes smaller as focus size increases. In the partial defocusing imaging sequence the beam is focused at the desired focal length and steered across the field of view. The partial defocusing sequence is similar to the standard sequence, but the size of the focus is bigger, thus decreasing the number of transmits required to illuminate a given area.

Figure 8:
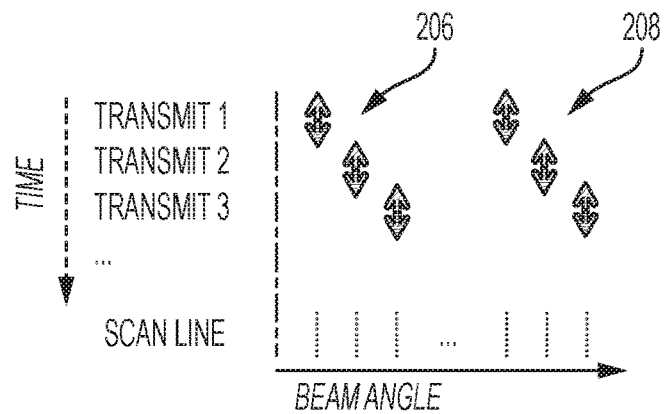
FIG. 8 illustrates embodiments in which multiple focused beams are simultaneously transmitted.

In another embodiment, an imaging technique consists of creating multiple foci for each transmit as shown in FIG. 8. The beam is focused at multiple angles, thus creating multiple beam lines in parallel to permit simultaneous acquisition of multiple beams 206A and 206B. It can be implemented different ways and is easily understood with an example; assuming three foci are desired. Firstly, it is possible to create three foci by sending three pulses on each element. The pulses have to be delayed by the amount of time needed to reach the different foci spots. This may be implemented on a scanner configured to transmit multiple pulses per element. In addition, equation 9, the well-known Fraunhofer approximation, shows that the pressure field is the Fourier transform of the pressure at the aperture.

$$P_{focal} \cong \mathcal{F}\{P_{aperture}\} \quad (9)$$

Figure 7B:
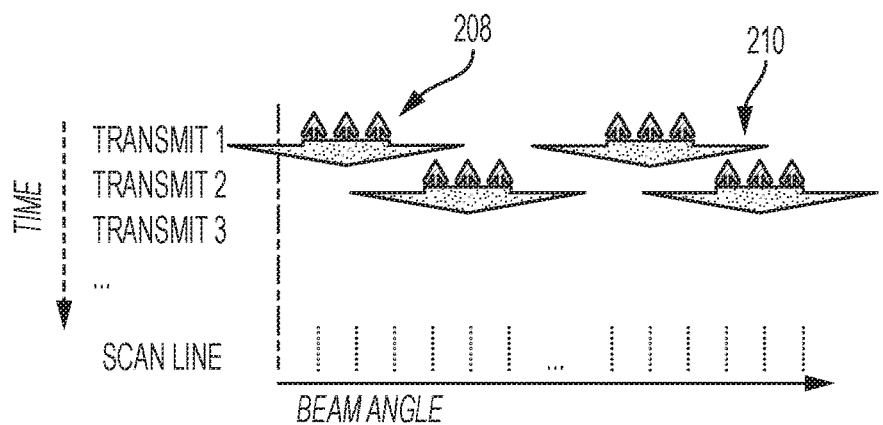

Another embodiment creates multiple foci through the application of an appropriate apodization function. FIG. 7B illustrates a variation of the embodiment of FIG. 8 in which multiple partially defocused transmit beams 208, 210 are emitted in parallel.

Figure 7C:
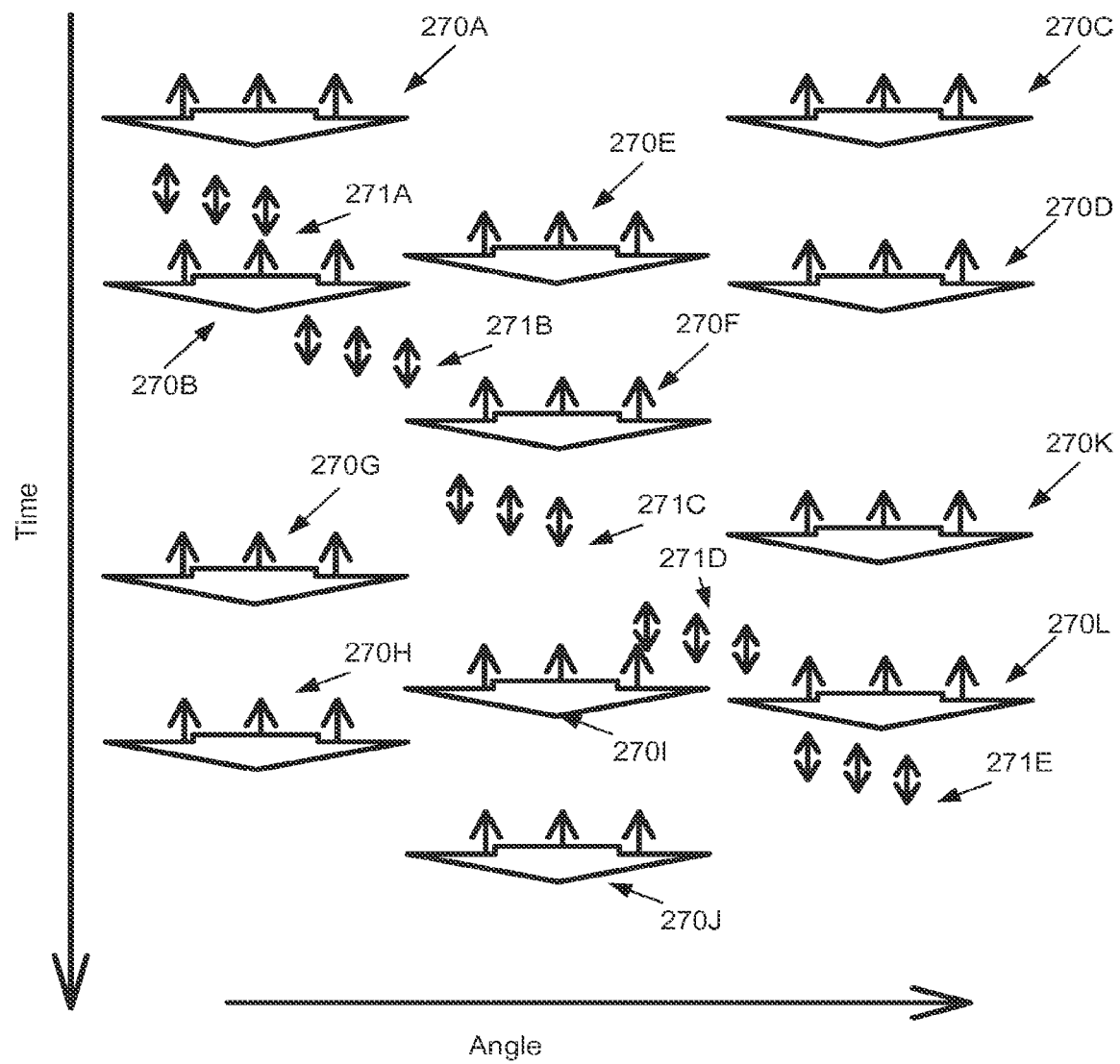

FIG. 7C shows another embodiment in which pairs of broad (defocused) transmit beams are used to acquire motion data as pairs 270A, 270B; 270C, 270D; 270E, 270F; 270G, 270H; 270I, 270J; and 270K, 270K. The pairs are interspersed among focused beam trains 271A, 271B, 271C, 271D, and 271E which in combination form a single image frame.

In evaluation experiments, four transmit patterns (focused, flash, partial defocusing and multi-foci) were implemented in combination with TUAS on an ultrasound scanner as follows for purposes of experimental evaluation: the embodiment of FIG. 7C may, as described with reference to FIG. 6C be used to provide arbitrary number of motion estimates per image frame using partially defocused transmit beams. The motion estimates may be used to increase the time resolution of motion estimation changes as well as to improve interpolation of image data acquired using the focused beams.

For the focused pattern, a conventional focusing method was used using suitable delays as in conventional beamforming. For the flash pattern, the delays in transmit were not set to zero. For the experiment, using a phased array, the field of view would have been too small if the wavefront was parallel to the probe. A diverging beam was used instead of the conventional approach with a larger probe. In the present approach, the focus was located behind the probe at a distance $z=(d/2)/\tan(\pi/4)$, where d is the size of the aperture.

For the partial defocusing example, the beam was focused following the conventional method, but an apodization window narrowing the aperture was used to increase the size of the focus. Several windows were implemented (rect, Hanning, Tukey, Blackman).

For the multiple focus example, in the same way as for the partial defocusing method, the beam was focused while applying an apodization window. The duality property of the Fourier transform shows that taking two Fourier transforms in a row results in inverting the input function and scaling it by a factor $2\pi$.

$$f(t) \Leftarrow F(\omega) \quad (10)$$

$$F(t) \Leftarrow 2\pi f(-\omega) \quad (11)$$

To obtain three foci, a function whose Fourier transform has three distinct peaks was used, a Battle wavelet (FIGS. 9A to 9B). The Battle wavelet is shown in FIG. 9A, its Fourier transform which serves as the apodization function in FIG. 9B, and the Fourier transform of the apodization function predicts the pressure field at the focal distance in FIG. 9C.

The example embodiments were tested using an ultrasound system that could store signals for each transducer in the array separately. For a 64 element phased array, this is 64 times the data compared to a conventional ultrasound system. Image depth for sampling was set to 12 cm. A tissue mimicking phantom was used which produced strain and motion using a pulsatile flow of water. The phantom was placed in a water tank which was filled to provide coupling. A 2.5 MHz phased array was used.

The image reconstruction is completely independent of the apodization function, so the same method was applied for each sequence. A pixel-based method was used instead of a conventional reconstruction where a line is computed by summing the data of each element over time. The pixel-based reconstruction computes the value of each pixel by summing only the RF data contributing to image the specific location. Contrarily to a conventional method where each line is computed by applying one set of delays to the RF, the pixel-based reconstruction applies different sets of delays for each pixel. Assuming the axis convention shown in FIG. 10 (A set of time delays is computed for each pixel based on the time needed for a wave to travel back and forth) and a constant speed of sound through the medium, the value of the pixels are given by $$s(x,z) = \int_{array} RF(k,t(k,x,z))dk$$

where (x,z) are the coordinates of the pixel wanted and t(k,x,z) is the time needed for a sound wave to travel back and forth from the point (x,z) to the element k on the probe. This reconstruction technique has been described for a flash sequence and adapted for our specific cases. A reconstruction was done for each transmit resulting in one sub-frame per transmit.

Displacements were estimated using a fast cross-correlation technique. 2D motion (axial and lateral) was estimated using a 1D kernel (5.0 mm) in each direction. There was a 80% overlap in the axial direction. In the lateral direction, the RF signals are interpolated along the lateral direction of the ultrasound beam to perform sub-beam lateral displacement estimation. Displacement maps were obtained after a two-steps process: firstly, displacements were estimated between sub-frames i and i+N, for [t=1, 2, 3, . . . , N−1], where N is the number of transmits used to image the complete field of view. The indexes and N+t correspond to the sub-frames reconstructed with the same transmit angle. Secondly, the displacement maps between two frames were computed as the sum of the N−1. maps previously obtained. Strains were computed as the spatial derivative of the displacements.

Laboratory tests showed that the partial defocusing and multi-foci methods could be used to estimate displacements. Both techniques created artifacts on the B-mode, but did not lead to any significant consequences on the displacements. The focused, partial defocusing, multi-foci and flash methods were implemented on the ultrasound scanner. Raster scans were performed in order to characterize the beam profiles and to assess a safety limit specific for each method. All the imaging techniques were tested in a phantom study and have shown to be capable of providing promising and coherent strain maps of a moving phantom.

In experiments with a canine heart, imaging sequences used a global frame rate of 131 Hz, a local frame rate of 418 Hz and 12 transmits per frames. The flash sequence was as described above. RF data were acquired as described above. The partial defocusing method was co-registered with cardiac mapping for comparison.

A pixel-based reconstruction was performed followed by displacement and strain estimation. The latter allowed the computation of isochronal maps of the electromechanical wave. On both isochrones, a wave propagating from the earliest activation point to the base and to the apex is clearly visible. Also, the last segment to be activated was the basal septum. The electrical activation times were compared with the onset of the EW at the approximate location of the electrodes.

A strong correlation was found between the isochrones of both techniques. This result demonstrates that the imaging technique implemented was suitable for EWI allowing an isochronal map to be obtained that was highly correlated with the measurements made with the cardiac mapping. The experiment was performed over a single heart cycle showing that the new imaging technique could replace composite imaging which requires multiple cycles and repeating motion.

In further experiments, axial displacements were estimated at a 500-Hz motion-estimation rate in both cases and at a 2000-Hz and 137-Hz motion-sampling rates in flash and wide beams sequences, respectively. A 1D cross-correlation algorithm of RF signals reconstructed at 20 MHz in a phased array configuration was used. The window size was 4.60 mm and the overlap 90%. The heart was segmented using an automated contour tracking technique. The incremental axial strains were estimated with a least-squares method and a kernel size of 10.7 mm. The strains were then overlaid onto the B-mode image acquired immediately following the flash sequence. Finally, isochrones were constructed as in previous studies.

The wide beam sequence was used in an open-chest animal and correlated with the electrical activation sequence during pacing from the apical region of the lateral wall. The heart was imaged in the four-chamber view, but with the ultrasound probe positioned parasternally. In that view, activation results mostly in thickening of the tissue (since the ultrasound beam is aligned with the radial direction of the heart). EWI shows activation originating from the apical region of the lateral wall, followed by the activation of the right-ventricular wall and finally by the septum. Corresponding EWI isochrones reflected this behavior. The EW and the electrical activation mapped using the basket catheter were highly correlated. A slope of 1.31 (R2=0.99) was obtained between the electrical activation and the EW onset.

EWI at 2000 fps was then performed in a standard apical four-chamber view in a normal, conscious canine during sinus rhythm using the flash sequence. In that view, the EW is expected to mostly result in shortening (negative strains) of the tissue, since the ultrasound beam is aligned with the longitudinal direction of the heart. During sinus rhythm, the natural pacemaker is the sinus node, located in the right atrium. Signals are generated spontaneously at the node, travel through the atrium (during the P-wave), to the atrio-ventricular node, the bundle of His and finally the Purkinje fiber network and the ventricular myocardium (during the QRS complex). Complex activation patterns are expected when imaging the ventricles, since activation will originate from multiple locations following the Purkinje fiber network. It was confirmed that the EW follows such a pattern. The EW originated from the right atrium and propagated towards the left atrium. Between the P- and the Q-wave on the ECG, little or no propagation is observed. During the QRS complex, activation originating from multiple sources, located for example at the mid-level of the septum, high on the lateral wall and near the right apex are observed. These results are in accordance with previous studies of the normal electrical activation of the heart and with previous studies using EWI with ACT.

The same animal was then imaged during pacing from the right ventricle after the ablation of the atrio-ventricular node. In that case, the electrical activation of the atria and the ventricles are dissociated, i.e., the activation of the sinus node do not necessarily results in the activation of the ventricles. This phenomenon was observed on an ECG trace, where multiple P-waves without a following QRS complex were observed. During the P-wave, the EW was initiated from the right atrium and propagated in the left atrium. This was expected, since the atria are still driven by the sino-atrial node as during sinus rhythm. During the QRS complex however, activation was triggered by the pacemaker located near the apex of the right ventricle. Therefore, the EW was expected to propagate from the right ventricle near the apex towards the other regions of the heart. EWI displayed such a pattern: the EW originated near the right ventricular apex and propagated towards the septum and the lateral wall.

The feasibility of flash- and wide-beam acquisition types for EWI in a full view of the heart were experimentally evaluated and confirmed. Experiments were first conducted in open-chest canines to allow for simultaneous cardiac electrical mapping using a basket catheter and confirming that a high correlation between EWI and cardiac mapping is maintained when using new transmit sequences. Then, experiments were conducted in a closed-chest setting In these canines, EWI was performed both during sinus rhythm and during right-ventricular pacing following atrioventricular dissociation, i.e., a non-periodic rhythm. EWI performed in a closed-chest setting while respecting the Food and Drug Administration standards is more prone to artifacts originating from reflections, e.g., from the rib cage, and thus similar to the clinical setting. Therefore, this study indicates that flash- and wide-beam EWI can be applied in humans and permits the study of irregular arrhythmias in patients.

FIG. 11A shows an example of a temporally unequispaced acquisition in 3D. The principles are applicable to estimation of motion in 1D and 2D along any axis of set of axes. A reference region 401 is first illuminated, in this case, by four beams 402 and echoes acquired to form a reference frame. Subsequently, a short time later, a comparison region 403 in the same plane is illuminated by, in this case, nine beams and the echoes acquired to form a comparison frame. The projection of beams 402 and 404 are shown at 406 and 408 respectively. The beams in the reference and comparison regions are recorded at the same axial depth, though are separated in the axial direction in figure for the sake of clarity. The time of transmit and acquisition of echoes of each beam is shown in FIG. 11B with each line numbered 1-4 and 1-9 indicating a corresponding beam as in FIG. 11A. This technique can be applied in either 1-D, 2-D, or 3-D estimations. The comparison beams 404 are arrayed around a respective one of reference beams 402 a spacing (st) and number such that an expected magnitude of displacement in the lateral and azimuthal directions may be detected. If only axial displacement is to be detected the reference and comparison beams can be arranged collinearly. In addition there may be different numbers of reference and comparison beams.

Referring to FIG. 12A, a larger region may be scanned by illuminating and acquiring multiple sets of reference 420 and comparison 422 regions rather than illuminating the entire global region 430 at once using the same TUAS technique as described above with reference to axial displacement estimation. The example TUAS sequence is depicted for three regions. Note that the reference and comparison regions are at the same axial depth, though are separated in this figure for clarity. The amount of time between the acquisition of a reference region and its corresponding comparison region may remain constant. A time graph of the sequence is shown in FIG. 12B. The bars 430, 431, and 432 bracket complementary pairs of regions 420 and 422. It is evident that a region may be scanned in interleaving steps. FIG. 12B shows the time is constant between the three separate regions. This technique can be applied in 1-D, 2-D, or 3-D estimations.

With regard to the scanning of reference and comparison regions, it may be desirable for motion estimation interval $T_{me}$ to be constant and as close as possible to an optimum (See FIGS. 5A-5C and discussion) because a small $T_{me}$ will generate a noisy motion estimation and a large $T_{me}$ will result in poor inter-frame correlation as a result of the deformation of structures. Assuming this and also the requirement that any group of beams must be acquired sequentially, which is the case for most ultrasound scanning systems in which the ultrasound signals are not multiplexed, though this is not an absolute requirement and the following may be adjusted for systems where beams can be transmitted simultaneously.

In the 1D, 2D, and 3D embodiments and embodiments where lateral (or non-axial) motion estimation is to be done, each reference beam (which will be called a principal line or PL) uses a group of beams (which will be called blocks) that are transmitted after an interval of $T_{ms}$. It is assumed that the members of the blocks will be transmitted consecutively so that the time between them is minimal and therefore they can best approximate transmission at a single instant of time. Using an index, a single principal line and a block of three lines could be designated i1, i2, i3, and i4.

In the case of 12 lines (i1 to i12) consisting of three blocks and three PLs, the lines can be arranged in 12! possible sequences. The possible arrangement will be reduced to satisfy two constraints mentioned above and restated here:

Constraint 1: i4, i5, i6 must be consecutive, as well as i7, i8 and i9 together and i10, i11 and i12 together.

Constraint 2: The second constraint is that the time between i1 and i4, i2 and i7 and i3 and i10 must be equal to ensure same motion estimation rate in each sector.

The sequencing problem can be described as one of placing 3 PLs into 12 possible spaces each corresponding to a beam transmit time. Below, each underscore represents a possible space where there can be a PL. Between two blocks there can be 0, 1, 2 PLs, because constraint 2 eliminates 3 PLs being together so the problem is locating the PLs into the spaces indicated by numbered spaces below.

| | block | | | | block | | | | block | | | | | | |
|---|---|---|---|---|---|---|---|---|---|---|---|---|---|---|---|
| 1 2 3 | 4 5 6 | 7 | 8 9 10 | 11 | 12 | 13 14 15 | 16 | 17 |

The potential positions for the PLs are: 1, 2, 6, 7, 11, 12, 16 and 17 since the blocks occupy {3, 4 and 5}, {8, 9 and 10} and {13, 14 and 15}. The first index of each block is: 3, 8, and 13.

The method now described is a constructive method that provides at least one sequence of the given number of sectors. The method may not be the only solution. For an odd number of PLs the PLs are placed every 4 positions starting from 1 (example: 1 5 9 and 13, which leaves {2,3,4}, {6,7,8}, {10,11,12}, {14,15,16} for the blocks). To maximize the distance between one PL and the block of its sector while fulfilling the requirement of constraint 2, the process is as shown in FIG. 37.

Divide the motion estimation rate by 10−1=9. For an even number of PLs place the PLs every 4 positions starting from 1 until half of the total number of positions are reached and then place PLs every 4 positions starting from the last possible index until half of the total number of positions is reached. For example: 1, 5, 9, 24, 20, and 16, leaves {2,3,4}, {6,7,8}, {10,11,12}, {13,14,15}, {17,18,19}, and {21,22, 23} for the blocks. Then maximize the distance between one PL and the block of its sector while fulfilling the requirement of constraint 2. Here the motion estimation rate is divided by 13−1=1. (See FIG. 38.)

So in a class of embodiments, a single temporal sequence of spatially separated ultrasound transmission beams is ordered in time in the following manner. A fraction of the beams are principal beams and the remaining are divided among the principal beams, two, three, four or more to each principal beam, each of these being called a "block." Each principal beam is separated in time from its respective block by a fixed time interval. All the beams of a given block are temporally adjacent one another. Each principal beam is separated from the members of its corresponding block by a predefined distance (or the distance may vary by region of the target structure or time depending on an expected rate of motion). Since the beams in a block are not temporally coincident, the time difference between a principal beam and its corresponding block is the time difference between one of its members and the principal beam. The predefined distance is selected responsively to the rate of movement of the target structure and the fixed time interval such that an axial pattern imaged by the reference beam will be identifiable the fixed time interval later (or prior) in an image from at least one of the members of the corresponding block.

In other embodiments, at a first time, the system transmits a reference beam and subsequently transmits corresponding comparison beams where each comparison beam is spatially separated from the reference beam within a range of displacements around the reference beam, the range of displacement being responsive to a predicted rate of displacement and the time interval $T_{ms}$ (a predefined interval) between the reference and one of the comparison beams. At a second time, multiple reference beams are transmitted which are spatially separated from another reference beam (the another reference beam not yet being transmitted at the second time) within a range displacements which are also responsive to the predicted rate of displacement and the time interval $T_{ms}$ between one of the comparison beams and the reference beam. After the second time, the corresponding reference beam is transmitted, which is located spatially in the middle of, or at least adjacent, the comparison beams. In embodiments, the comparison beams corresponding to the reference beam are temporally adjacent (i.e., they are transmitted together without any other beams being transmitted temporally between them). So essentially what this is saying is that sometimes the reference beam of a reference beam-comparison beam block pair will be transmitted in that order and sometimes they will be transmitted in reverse order.

Figure 14:
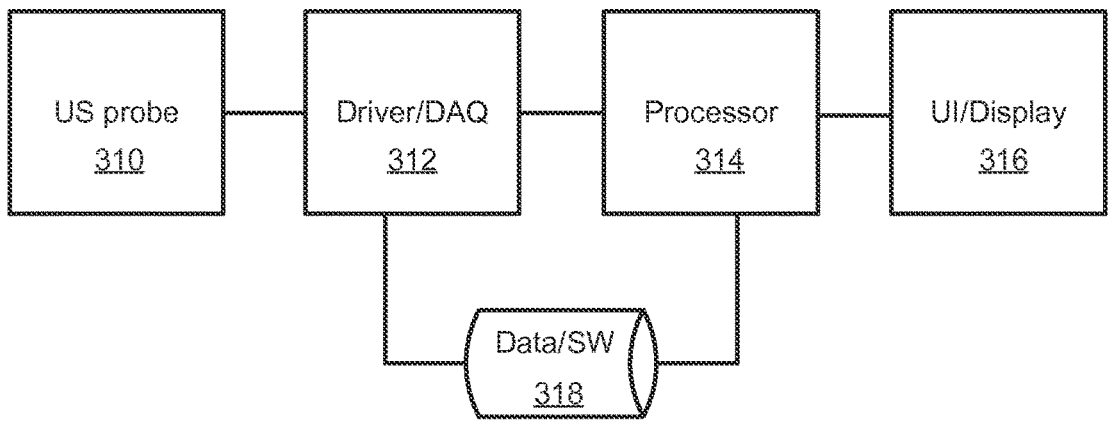
FIG. 14 figuratively illustrates a TUAS system.

FIG. 14 shows an ultrasound system 301 including one or more ultrasound probes 310, a driver/data acquisition element 312, a processor 314, and a user interface and display element 316. The driver/data acquisition element 312 and a processor 314 communicate with a data store 318 for raw ultrasound signal data, reduced data such as images, image sequences, and motion estimation data, and software. The ultrasound probe 310 may include multiple probes that are used simultaneously (frequency encoded, for example) or a kit of probes that are used at different times. Also the ultrasound probe 310 may be a combined probe with multiple heads that are automatically driven at different times such as flash sequence probe and a phased array probe combined as a unit that can generate both flash pulses and focused beams for combined scans, for example as discussed above with reference to FIGS. 6B and 6C. The system 301 is figurative and it should be clear based on the state of the art in digital data acquisition and control systems that any of the elements of the system 301 may include one or more components for each function or the functions combined into combined elements.

Figure 13:
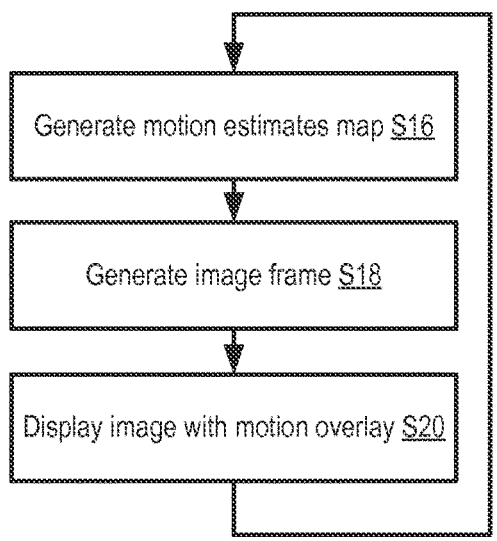
FIG. 13 illustrates processes for setting up and generating output for TUAS systems.
Figure 13:
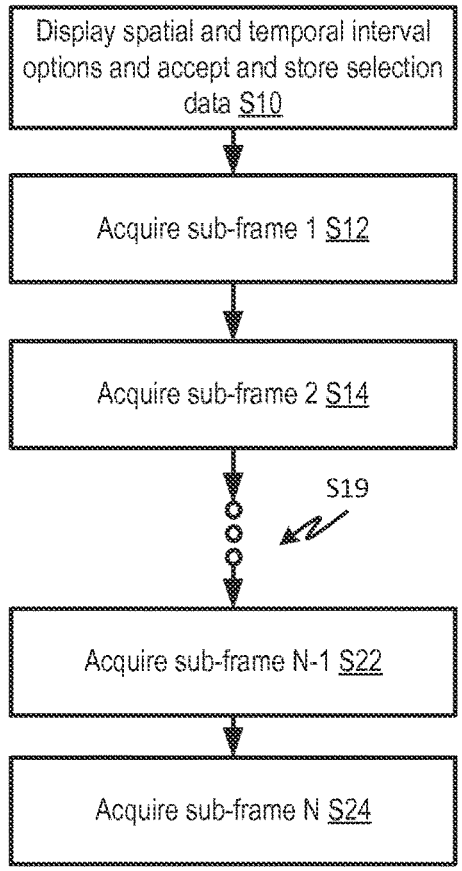

FIG. 13 shows a process 280 for generating a display which runs in parallel with a process 282 for acquiring sample data which is passed by a data store or transfer channel to the process 280. At S10, parameters of the scan are displayed on the user interface and selected. For example, the parameters may be displayed on a touch screen and selected by touch. Alternatively names profiles may be stored and provide grouped selections. The parameters that may independently on a per session or per profile basis may include the following or equivalents.

Type of scan (TUAS narrow beam, TUAS broad beam, Flash with B-mode, etc.)

$T_{ms}$—the temporal spacing of ultrasound image frames.

$T_{me}$—the temporal spacing of motion/strain estimation frames.

$s_t$—the spacing of comparison region lines from corresponding reference region lines.

Number of beams.

Virtual origin of diffuse beam approximation of flash (if phased array used to generate).

In addition, conventional parameters of ultrasound may also be chosen as well as any other parameters of the embodiments described herein.

At S12, a first subframe or flash acquisition is made and at S14 a second subframe or flash acquisition is made. One or more focused beam acquisition may occur between the flash acquisitions if flash mode embodiments are being performed. The steps are repeated as indicated by the elipses S19 and S22, S24 while in the contemporaneous process 280, the acquired data is processed into images and motion data in S16, S18 and displayed S20. The processing of process 280 may take advantage of delays in process 282 or may employ hardware and I/O and data storage subsystems and techniques to permit completely independent execution of S280 and 282. As a result, real time or near real time display of anatomy and motion data may be provided.

In all of the disclosed embodiments where transmit focused or partially focused beams are used, the ultrasound images can be generated from stored data received at all transducers in an array (2D or 3D) of the ultrasound probe from a wide or flash beam transmit using known signal processing techniques under the general category of receive beam forming. Thus additional embodiments can be generated from the above disclosure by making this change in the structures and methods.

Figures 17A, 17B, 17C:
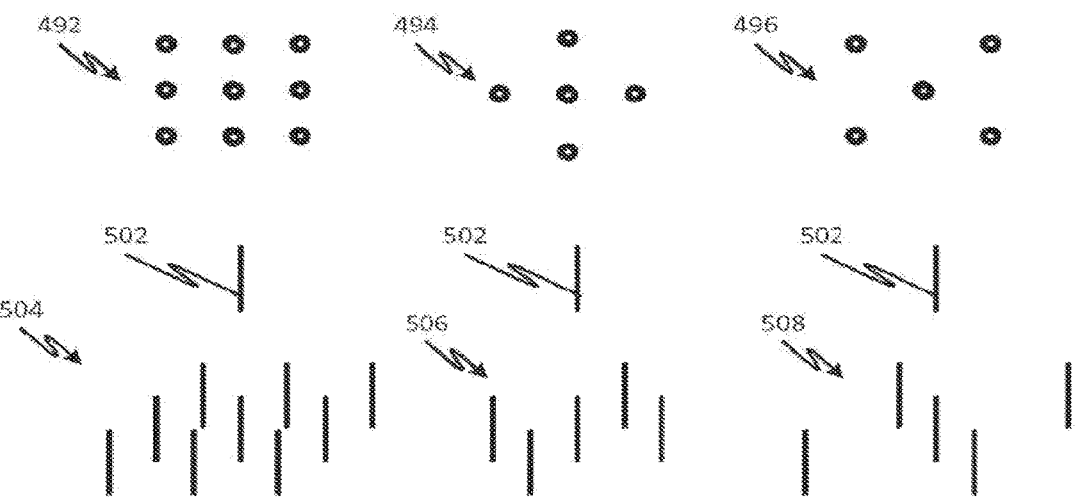
FIGS. 17A, 17B, and 17C show alternative variations of the beam layouts of FIGS. 11A, 11B, and 12A, 12B for lateral strain estimation in 3D.

FIGS. 17A, 17B, and 17C show alternative variations of the beam layouts of FIGS. 11A, 11B, and 12A, 12B for lateral strain estimation in 3D. In FIG. 17A, the principal beam 502 has a block 504 of 9 beams with one beam collinear with it. The plan view is shown at 492. In FIG. 17B, the principal beam 502 has a block 506 of 5 beams with one beam collinear with it. The plan view is shown at 494. In FIG. 17B, the principal beam 502 has a block 508 of 5 beams with one beam collinear with it. The plan view is shown at 494. These three layouts can be modified by the removal of the collinear beam to form new embodiments. These figures are included to highlight that various beam layouts are possible.

Figures 17D, 17E:
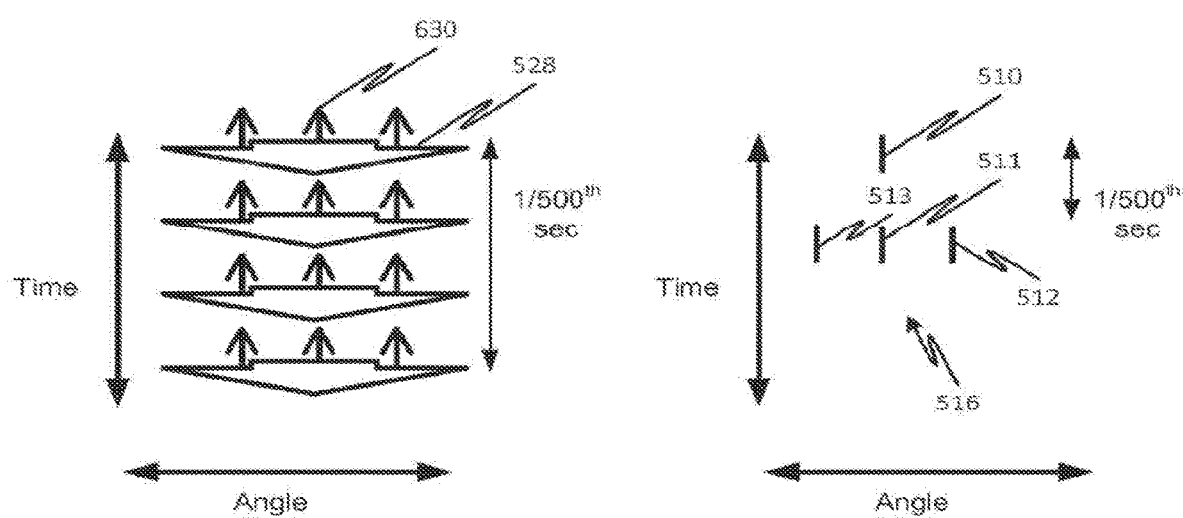
FIGS. 17D and 17E illustrate a 2D arrangement for lateral strain estimation that was validated by experiment.

FIGS. 17D and 17E illustrate a 2D arrangement for lateral strain estimation that was validated by experiment. The acquisition was of a canine heart using flash 528 sequences with the receive beams 630 indicated for illustration. The beamforming can be done using stored data and was done that way in the validation experiment. The frequency of flash transmits was 2000 Hz. Four flash transmits are shown but 4000 were generated over the 2 sec. cycle of the data acquisition. Each flash is used to generate a principal beam which is compared to block of beam formed from a flash ⅟500 sec. removed and this is repeated for the nearly 4000 flash pulses for which it is possible.

In the experiment, images were acquired using a phased array probe with 64 elements. Images were acquired at 2000 fps during 2 sec. interval followed immediately by the acquisition of a 128 line, 30 fps, B-mode image over 1.5 s. An electrocardiogram (ECG) was acquired simultaneously. RF signals were reconstructed from the element data in a pixel-wise fashion. As mentioned, lateral displacements were estimated at a 500 Hz motion-estimation rate and at a 2000 motion-sampling rate.

The incremental lateral displacements that occurred from end-diastole to end-systole were integrated to obtain the cumulative lateral displacement. For each pixel, appropriate registration between consecutive displacement images was performed in order to ensure that the cumulative displacement depicted the motion in the same myocardium region. The cumulative lateral strains were estimated from the cumulative lateral displacements with a least-squares method and a kernel size of 10.7 mm. The strains were then overlaid onto the B-mode image acquired immediately following the flash sequence to generate a display sequence which was reviewed with the following observations.

The cumulative lateral strain showed that during systole, the left and right segments of the myocardium exhibit lateral lengthening, while the top and bottom segments show slight lateral shortening. These results show the feasibility of lateral tracking in a canine myocardium.

Figure 15A:
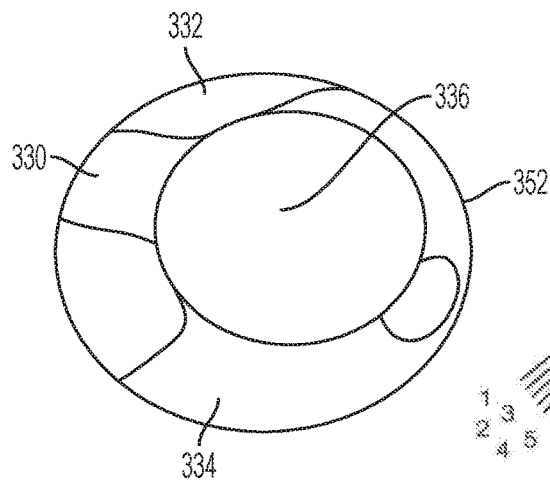
FIGS. 15A through 15C illustrate features of output display embodiments where signals received for motion estimation of body structures and fluid flows are combined as enabled by the time resolution of TUAS.
Figure 15B:
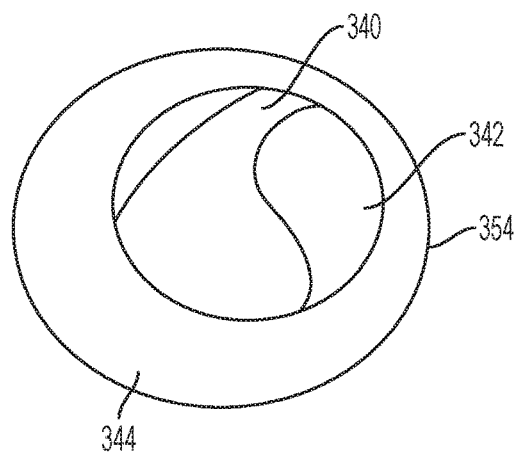
Figure 15C:
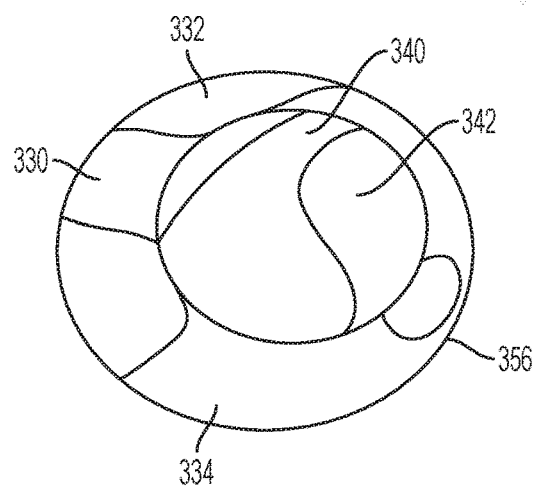

In all of the foregoing embodiments, the motion capture and estimation is not limited to tissue structures such as muscle. The velocity of fluid such as blood can be captured using the higher rate data. The flow of blood in the ventricles may be simultaneously captured along with motion such as the electromechanical wave. The user interface may allow a selective display of the fluid (e.g. Blood) data and other tissue as illustrated in FIGS. 15A through 15C. In FIG. 15A, displacement contour or color maps (regions indicated by 330, 332, 334) for non-fluid tissue structure (such as myocardium) are shown in an image sequence. One or more controls may be actuated to switch to motion data display of fluid near or within the tissue stricter 354 in a further display of FIG. 15B (showing, for example, velocity contour map regions 340, 342) or combined in FIG. 15C.

Figure 16A:
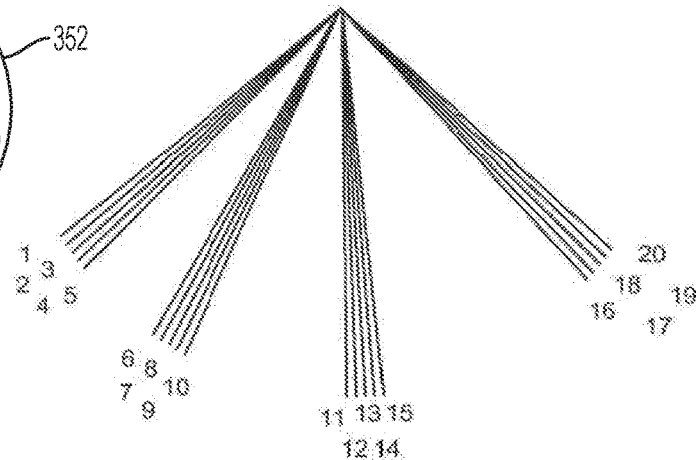
FIGS. 16A and 16B illustrate spatially unequispaced and temporally unequispaced beam embodiments.
Figure 16B:
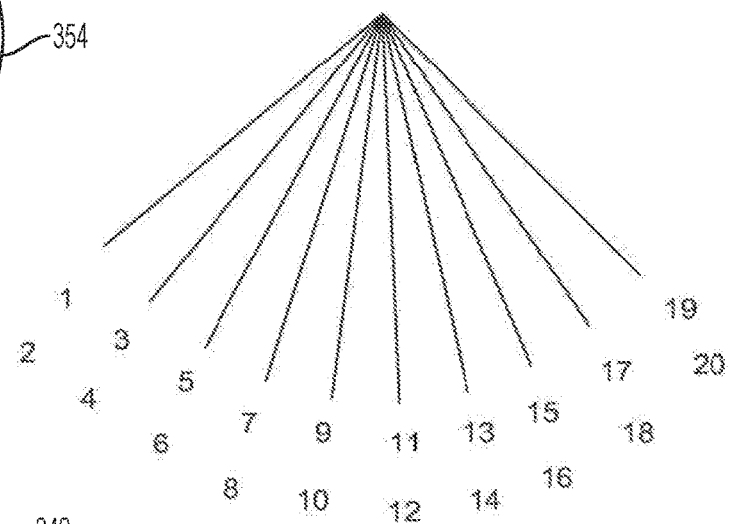

FIG. 16A illustrates a spatially unequispaced transmit beams, which may be focused or unfocused. The embodiment increases the local beam density. This may be used to spend the line density budget where it can provide the most benefit. For example, it may be known a priori or through a prior registration imaging cycle, that the motion to be imaged occurs at particular regions. These regions can be imaged with high beam density and surrounding regions may be imaged with lower line density. For example, the progress of EW in myocardium may be known or determined from prior imaging and used to change the beam density during a cardiac cycle so as to improve the relevant image. Also this may permit high temporal resolution by permitting a smaller line count to be used. An another alternative, the beams are expanded and focused variably over a single scan in a manner similar to FIG. 7C embodiments, but responsively to the locations where spatial resolution is needed. For example, low resolution requirement regions are scanned with broad transmit beams and high resolution requirement regions with narrow beams. In FIGS. 16A and 16B, the beams are indicated by number indicating the timing of the beam in a sequence. FIG. 16B shows a special case of the embodiment of FIG. 3 in which the beams are scanned twice in a row to be used for motion estimation.

In all of the foregoing embodiments, various methods devices and systems are described at least for addressing the problems of EWI. In EWI, inter-frame motion (or, displacement) is estimated axially via cross-correlation of consecutive RF frames. From the displacements, one can then obtain the inter-frame strains (or, strains) depicting the EW by applying gradient operators on the displacement field. However, the heart is an organ that undergoes significant three-dimensional motion and large deformations, which both lead to the decorrelation of the RF signals and thus to the degradation of the motion and deformation estimation accuracy. Increasing the imaging frame rate reduces these effects. However, imaging at high frame rates over a large field of view and at high resolution constitutes a technical challenge which is addressed by the present technology.

In any of the foregoing embodiments, the data handling burden may be limited by scanning at a specific point in a cyclical event, such as a cardiac cycle. This may be done by scanning for a few cycles and then predicting the next cycle start and end times and controlling the ultrasound acquisition to begin and end within those times.

In many of the foregoing embodiments, the sequence of the transmit beams is such that spatially adjacent beams are transmitted consecutively.

In many of the foregoing embodiments, the sequence of the transmit beams is such that scanned beams (beams other than flash) are repeated for each frame. However, it will be clear that this is not a requirement in that beams that are close to, but not coincident with, prior beams, can still be used to generate images that can be compared to generate motion estimates and image sequences. Thus, all of the foregoing embodiments may be modified such that beams making up mini-frames and partly defocused beams may be aimed differently even for those forming a pair to be compared for motion estimation. For example, transmit beam 270A and 270B in FIG. 7C may be shifted spatially (angle-wise) relative to each other, within limits.

According to embodiments, the disclosed subject matter includes an ultrasound system for imaging a target structure that moves or deforms with time. The system includes an ultrasound imaging device configured to image at a spatial resolution and sample a predefined field of view no faster than a frequency $1/T_{ms}$. The target structure is one which moves or deforms such that relative displacement of portions of the target structure of a size equal to the inverse of the spatial resolution are substantially uncorrelated at time intervals greater than a time interval $T_{me}$. The target structure is also one where relative displacements propagate over time scales many times greater than $T_{me}$ where $T_{me}$ is much smaller than Tms. The system has a controller configured to control the ultrasound imaging device to image the target structure at a frequency of $1/T_{me}$ and to capture relative displacement data responsive thereto. The controller is further configured to generate an image sequence representing the field of view in which the relative displacement data is shown on the image sequence.

The controller may be configured to acquire multiple first image frames consecutively in time which first image frames are smaller than the field of view. The controller may further be configured to assemble first image frames to form second image frames spanning the field of view.

According to embodiments, the disclosed subject matter includes method for estimating properties of motion of a body structure. The method includes directing at least a first ultrasonic beam into a first angular sector of the body structure. The method further includes directing at least a second ultrasonic beam into a second angular sector of the body structure. The method further includes directing at least a third ultrasonic beam into the first angular sector of the body structure prior to the directing at least a second ultrasonic beam into the second angular sector of the body structure. The method further includes detecting motion of the body structure in the first angular sector by detecting a magnitude of a displacement of a portion of the body structure occurring between return echoes from the at least a first ultrasonic beam and the at least a third ultrasonic beam.

According to embodiments, the disclosed subject matter includes a method for estimating properties of motion of a body structure. The method includes directing a first at least three ultrasonic beams into respective angular sectors of the body structure, the angular sectors combining to span a field of view of an ultrasonic transducer, wherein the beams are separated by at least first and second angular intervals so that the angular beam density varies over the field of view. The method further includes repeating said directing for a second at least three ultrasonic beams and receiving return echoes from the first and second at least three ultrasonic beams. The method further includes detecting motion of the body structure by detecting a magnitude of a displacement of a portion of the body structure occurring between the return echoes from the at least three ultrasonic beams.

According to embodiments, the disclosed subject matter includes a method for estimating properties of motion of a body structure. The method includes generating a reference ultrasound scan of region of the body structure at a selected axial depth using a pattern of first beams distributed over a first angular range and directed at respective first angles. The method further includes generating a comparison ultrasound scan of the region of the body structure at the selected axial depth using a second pattern of beams distributed over substantially the first angular range and directed at respective second angles. The first angles and the second angles are non-collinear. The first angles may be distributed over solid angular ranges. The first and second angles may be distributed over solid angular ranges. The first angles may lie between respective ones of the second angles.

According to embodiments, the disclosed subject matter includes a method for estimating properties of motion of a body structure. The method includes generating a first reference ultrasound scan of a region of the body structure at a selected axial depth using a pattern of first beams distributed over a first angular range and directed at respective first angles. The method further includes generating a first comparison ultrasound scan of the region of the body structure at the selected axial depth using a second pattern of beams distributed over substantially the first angular range and directed at respective second angles. The method further includes generating a second reference ultrasound scan of region of the body structure at a selected axial depth using a pattern of first beams distributed over a second angular range and directed at respective third angles. The method further includes generating a second comparison ultrasound scan of the region of the body structure at the selected axial depth using a second pattern of beams distributed over substantially the second angular range and directed at respective fourth angles. The first, second, third, and fourth angles are non-collinear.

The first angular range may be a solid angular range. The first and second angular range may be a solid angular range. The first angles may lie between respective ones of the second angles.

According to embodiments, the disclosed subject matter includes a method for estimating properties of motion of a body structure including directing, into the body structure, first and second broad ultrasound beams in respective first and second transmit events. For each of the transmit events, the multiple receive beams may be formed to form first images of said body structure at first and second times. The method further includes generating motion information by comparing the first images. The method further includes generating first and second ultrasound image scans using focused beams generated by first and second sets of transmit events. The first and second transmit events and the first and second sets of transmit events all occur during a single motion event of said body structure.

The single motion event may be induced by an electromechanical wave in a heart muscle. The first set of transmit events may occur at a time between the first and second transmit events. The first and second transmit events and the first and second sets of transmit events may have substantially the same spatial scope. The method may also include generating a B-mode image responsively to the first and second ultrasound scans and overlaying motion data resulting from the step of generating motion information. The method may further include generating a B-mode image sequence responsively to the first and second ultrasound scans and overlaying motion data resulting from the step of generating motion information.

According to embodiments, the disclosed subject matter includes a high frame rate ultrasound image acquisition method. The method includes generating waveforms with respective time delays and respective apodization weightings determined to cause selected transducer elements of a transducer array to transmit respective transmit beams along corresponding transmit beam paths toward a body structure to be imaged during a first transmit event such that the first transmit event is distributed over a first portion of a field of view. This is followed by transmission of respective transmit beams along corresponding transmit beam paths during a second transmit event distributed over a second portion of the field of view. The method includes acquiring a first plurality of spatially separated beam lines at selected transducer elements during a first receive event subsequent to said first transmit event along corresponding receive beam paths, and acquiring a second plurality of spatially separated beam lines at selected transducer elements during a second receive event subsequent to said second transmit event along corresponding receive beam paths. The first plurality of spatially separated beam lines are acquired multiple times in succession before acquiring the second plurality of spatially separated beam lines.

According to embodiments, the disclosed subject matter includes a method for estimating properties of motion of a body structure using ultrasound. The method includes directing a first beam into the body structure, directing multiple second beams into the body structure, where a and b are repeated in the sequence: at least two a) events followed by at least one b) event which sub-sequence is repeated multiple times with each sequence is the same or different from other sequences, from multiple a) events, estimating the displacement of anatomical portions of said body structure to generate at least first motion estimates from echoes of the first beams. from multiple b) events. The method further includes estimating at least the relative positions of anatomical portions of said body structure from echoes of said second beams over time to generate images of said body structure, and combining the images and first motion estimates to form a display indicating motion within the body structure.

The first beams may be wider than the second beams. The first beams may be parallel beams. The first beams may be single pulses spanning a field of view of the body structure.

According to embodiments, the disclosed subject matter includes a method for estimating properties of motion of a body structure using ultrasound, comprising: generating a first beam aimed a first fraction of a field of view of the body structure. The method includes receiving multiple beams from a received echo to generate a first image frame. The method further includes generating a second beam aimed the first fraction of the field of view of the body structure. The method further includes receiving multiple beams from a received echo to generate a second image frame. The method further includes comparing the first and second frames and generating motion estimates from a result of the comparing. The method further includes repeating the foregoing generating and receiving while aiming the first and second beams at a second fraction of the field of view to generate successive image frames covering the entire field of view. The method further includes combining the motion estimates and successive image frames to generate an output signal indicating tissue deformation in said body structure as well as the movement of anatomical features of said body structure.

The output signal may represents a video sequence. The combining may include compensating gross motion information represented in the successive image frames.

According to embodiments, the disclosed subject matter includes a method for estimating properties of motion of a body structure using ultrasound, comprising: generating a first beam aimed at the body structure. The method includes receiving multiple beams from a received echo to generate an image frame. The method includes repeating the foregoing generating and receiving to generate successive image frames covering the entire field of view. The method further includes cross-correlating the image frames to generate motion estimates. The method further includes combining the motion estimates and the successive image frames to generate an output signal indicating tissue deformation in said body structure as well as the movement of anatomical features of said body structure.

According to embodiments, the disclosed subject matter includes a method for estimating properties of motion of a body structure using ultrasound. The method includes generating a first and second beams simultaneously from a first ultrasound transmission and focused at first respective regions of the body structure. The method further includes generating a third and fourth beams simultaneously from a second ultrasound transmission and focused at second respective regions of the body structure. The method includes receiving echos to generate an image frame from the foregoing generating. The method further includes repeating the foregoing generating and receiving to generate successive image frames covering the entire field of view and cross-correlating the image frames to generate motion estimates. The method further includes combining the motion estimates and the successive image frames to generate an output signal indicating tissue deformation in said body structure as well as the movement of anatomical features of said body structure.

According to embodiments, the disclosed subject matter includes a method for estimating properties of motion of a body structure using ultrasound. The method includes imaging a field of view in multiple sectors, the images for each sector being taken sequentially at first frame rate. The method further includes reconstructing a composite image of the entire field of view by appending the images for each sector together, estimating motion corresponding to the first frame rate from the images for respective sectors and combining with the composite image.

The method may further include repeating the imaging and reconstructing to form a composite image sequence.

In any of the disclosed methods, the motion estimates may include axial displacement magnitude. Also, in any of the disclosed methods, the image frames may include phase information and the motion estimation may be generated by comparing phase information of the reflected ultrasound.

According to embodiments, the disclosed subject matter includes an ultrasound method for acquiring sequential images of a target sample that moves in a unique pattern over an interval of a single movement cycle, the method being for constructing an image sequence of fractional image frames from a plurality of beam lines. The beam lines are spatially separated from each other. The method includes varying an acquisition order of multiple beam lines, a beam line size, and/or a shape of a beam focus over the interval of the single movement cycle to acquire successive fractions of the movement cycle during the single movement cycle.

The varying the acquisition order may include: dividing an image frame into a plurality of image frame sectors, sequentially imaging the image frame sectors over multiple frames, and combining the acquired image frame sectors to obtain a complete image of the target sample.

The varying the acquisition order may include acquiring a plurality of lines in a first region of the target sample before acquiring lines from an adjacent region thereby increasing locally the line density (i.e., temporally-unequispaced acquisition sequences (TUAS)). The varying the acquisition order may include acquiring the same line in a target region before the end of a frame acquisition, thereby reducing the time between consecutive lines (i.e., temporally-unequispaced acquisition sequences (TUAS)). The varying the acquisition order may include acquiring a plurality of lines in a first region of the target sample before acquiring lines from an adjacent region thereby increasing locally the line density and acquiring the same line in a target region before the end of a frame acquisition, thereby reducing the time between consecutive lines (i.e., temporally-unequispaced acquisition sequences (TUAS)). The varying the size and/or shape of the beam focus may include transmitting a limited number of the available beam lines over the target sample, each transmission including multiple beam lines, thereby generating multiple focused transmit events scanned across a field of view (i.e., focused sequences). The varying the size and/or shape of the beam focus may include transmitting all available beam lines at the same time across the target sample thereby generating a single transmit event distributed over a field of view (i.e., plane-wave or flash sequences). The varying the size and/or shape of the beam focus may include sequentially scanning spatially separated beam lines across the target sample while varying the size of the focus thereby controlling the size of the focus and the number of lines per transmit (i.e., partially-defocused sequences). The varying the size and/or shape of the beam focus may include generating multiple focus points for each beam line transmit (i.e., multi-foci sequences).

According to embodiments, the disclosed subject matter includes a method of identifying an optimal sequence acquisition method for electromechanical wave imaging (EWI) of a target sample. The method includes (a) performing an image sequence acquisition on a target sample to reconstruct an image of the target sample according to any of the describe methods. The method further includes (b) estimating axial, lateral, and/or elevational displacements based on the image obtained from (a), and comparing the results in (b) with previously generated axial, lateral, and/or elevational displacements. The previously generated axial, lateral, and/or elevational displacements may be generated at an optimal frame rate.

According to embodiments, the disclosed subject matter includes a system to generate a cardiac activity map of a target sample. The system has a plurality of electrodes positioned along a portion of the target sample to detect electrical activity at respective locations and a measuring device connected to the plurality of electrodes and configured to measure potential differences between adjacent electrodes and generate corresponding data signals. The system further includes a processing device adapted to process the data signals received from the measuring device and to generate a 3D electrical activation map based on the processed signals and a display device to display the generated electrical activation map.

The system may further include a device for filtering and amplifying the data signals prior to generating the electrical activation map. The device may include a printed circuit board. The system may further include a controlling device to control the pacing of the target sample.

According to embodiments, the disclosed subject matter includes a method of imaging a biological tissue. The method includes capturing at least two successive frames of a first subsection of the biological tissue. The method further includes subsequently capturing at least two successive frames of a second subsection of the biological tissue. The method further includes generating a still or moving image of the combined first and second subsections from both the at least two successive frames and generating motion estimation data respective to each of the first and second subsections from the respective at least two successive frames corresponding to the each of the first and second subsections from a comparison of the each of the at least two successive frames.

The capturing may include imaging with ultrasound.

According to embodiments, the disclosed subject matter includes a method of imaging biological tissue including using ultrasound to acquire image sequence data representing motion of the biological tissue at a first frame rate and also motion information at a second frame rate that is faster than the second frame rate by scanning each of the respective subsections of the biological tissue at the second frame rate at least enough times to produce motion estimation data for the respective subsection, and scanning multiple subsections in the aggregate at least enough times for form the image sequence.

The method may further include superposing the motion estimation or data derived therefrom onto an image sequence captured at the first frame rate. The method may further include scanning a first subsection twice and scanning a second subsection twice, then returning to the first subsection and repeating. The biological tissue may be a myocardium.

According to embodiments, the disclosed subject matter includes a method of imaging a electromechanical wave by using ultrasound to capture a moving image of a myocardium at a first frame rate over a single cardiac cycle, the capturing including scanning to permit the acquisition of motion estimates from motion estimation frames representing images of a fraction of the myocardium where a time difference between the motion estimation frames is shorter than the inverse of the first frame rate.

According to embodiments, the disclosed subject matter includes a method of generating ultrasound motion information. The method includes scanning multiple A or RF beam lines to obtain spatial information of a target medium. The scanning includes scanning beam lines separated by a first spatial separation over a first spatial scanning range and separated by a second spatial separation over a second spatial scanning range to capture a first frame and repeating for multiple frames to obtain locally higher line density in a first region of the target medium and lower line density in a second region of the target medium to capture a first frame and repeating for multiple frames to obtain locally higher line density in a first region of the target medium and lower line density in a second region of the target medium.

According to embodiments, the disclosed subject matter includes a method of generating ultrasound motion information including scanning multiple A or RF beam lines to obtain spatial information of a target medium, the scanning including scanning a first beam line a selected number of times, at least twice in succession, to obtain a higher motion estimation rate along the first beam line than a frame rate, and repeating for multiple frames.

According to embodiments, the disclosed subject matter includes a method of generating ultrasound motion information that includes the two foregoing methods in combination.

According to embodiments, the disclosed subject matter includes an ultrasound method for acquiring sequential images of a target sample for reconstructing an image frame from a plurality of beam lines, the lines is spatially separated from each other. The method includes acquiring a plurality of lines in a first region of the target sample before acquiring lines from an adjacent region thereby increasing locally the line density.

According to embodiments, the disclosed subject matter includes an ultrasound method for acquiring sequential images of a target sample for reconstructing an image frame from a plurality of beam lines, the lines being spatially separated from each other. The method includes acquiring the same line in a target region before the end of the frame acquisition, thereby reducing the time between two consecutive lines.

According to embodiments, the disclosed subject matter includes a system for mapping transient deformations of a myocardium resulting from electrical activation (i.e., electromechanical wave imaging) within a single heartbeat using an ultrasound method as in any of the described method.

According to embodiments, the disclosed subject matter includes a system for detecting and characterizing periodic and non-periodic cardiac events using electromechanical wave imaging within a single heartbeat using any of the methods described herein.

Note that the mentioned non-periodic events may include arrhythmias, such as fibrillation.

According to embodiments, the disclosed subject matter includes a method for mapping transient deformations of the myocardium within a single heartbeat at an optimal frame rate, wherein the optimal frame rate includes a frame rate which is adapted to accurately estimate cardiac deformations.

According to embodiments, the disclosed subject matter includes a method for identifying an optimal frame rate for electromechanical imaging of the target sample. The method includes varying a frame rate while maintaining a set of imaging parameters constant and determining the optimal frame rate based on an elastographic signal-to-noise ratio.

According to embodiments, the disclosed subject matter includes a method for estimating properties of motion of a body structure using ultrasound. The method includes scanning the body structure using multiple focused beams from a phased ultrasound array of transducer elements according to a predefined sequence. The beams form spatially adjacent groups. The sequence defines the temporal order in which the beams are transmitted. The sequence is such that each spatially adjacent group is transmitted twice a predetermined interval apart before another spatially adjacent group is transmitted.

The scanning may be performed using a phased array of transducer elements. The body structure may be a myocardium. The method may be applied for body structures that are myocardium and with no external source of motion other than the natural motion of the myocardium and the ultrasound used for scanning is present. The time difference between the successive transmits used to capture motion estimation data may be selected responsively to an estimate of image cross-correlation or noise.

In any of the disclosed methods, the time difference between the successive transmits used to capture motion estimation data may be selected responsively to a probabilistic estimate of signal to noise ratio.

According to embodiments, the disclosed subject matter includes a method for estimating properties of motion of a body structure using ultrasound. The method includes generating single temporal sequence of spatially separated ultrasound transmission beams ordered in time. A fraction of the beams are principal beams and the remaining are divided among the principal beams, with multiple beams corresponding to each principal beam forming a corresponding block. Each principal beam is separated in time from its respective block by a predetermined motion estimation time interval, wherein the time difference between a principal beam and its corresponding block is taken as the time difference between one of its members and the principal beam. The beams of each block are mutually temporally adjacent (i.e., generated one right after the other without any other intervening beams). Each principal beam is separated from the members of its corresponding block by a predefined distance.

The predefined distance may be selected responsively to the rate and variability of the movement of the target structure and the fixed time interval such that an axial pattern imaged by the reference beam is identifiable the fixed time interval later (or prior) in an image from at least one of the members of the corresponding block. The at least one of the blocks may be transmitted before its corresponding principal beam. The at least one of the principal beams may be transmitted before its corresponding block. The predefined distance may vary by region of the target structure or time depending on a predicted rate of motion of the region of the target structure. The predefined distance may vary by region of the target structure or time responsively to a predicted rate of motion of the region of the target structure. The members of each block may be arrayed in two dimensions around its corresponding principal beam. The members of each block may be three in number. The members of each block may vary in number and average between 2 and four in number.

According to embodiments, the disclosed subject matter includes a method for estimating properties of motion of a body structure using ultrasound, comprising: at a first time, transmitting a reference beam and subsequently transmitting corresponding comparison beams where each comparison beam is spatially separated from the reference beam within a range of displacements around the reference beam, the range of displacement being selected responsively to a predicted rate of displacement and a time interval Tms between the reference and one of the comparison beams. The method including, at a second time, transmitting multiple comparison beams, the comparison beams is spatially separated from another reference beam, the another reference beam not yet being transmitted at the second time, located within a range displacements which are also responsive to the predicted rate of displacement and the time interval Tms after the second time. The method including transmitting the another reference beam the time interval Tms later, the reference beam being located spatially adjacent, the corresponding comparison beams. The comparison beams may correspond to a given reference beam are mutually temporally adjacent, i.e., they are transmitted together without any other beams is transmitted temporally between them. The another reference beam may be spatially between the corresponding reference beams.

According to embodiments, the disclosed subject matter includes a method for estimating properties of motion of a body structure using ultrasound, comprising: scanning the body structure using ultrasound to generate a series of image frames at an sampling rate, each image representing the configuration of the body structure at a point in time and spanning a field of view of an ultrasound scanner, the scanning including capturing displacements of portions of the body structure at intervals less than an inverse of the sampling rate.

According to embodiments, the disclosed subject matter includes a method for estimating properties of motion of a body structure using ultrasound, comprising: receiving a first input signal from a user interface representing data indicating a sampling rate. The method includes receiving a second input signal from a user interface data indicating a motion estimation frequency. The method includes scanning the body structure using ultrasound to generate a series of image frames at the sampling rate, each image representing the configuration of the body structure at a point in time and spanning a field of view of an ultrasound scanner. The scanning may include capturing displacements of portions of the body structure at the motion estimation frequency and outputting a result of said scanning in the form of an image sequence showing representations of the image frames as a video sequence with motion data responsive to the displacements superposed thereon. The time difference between the successive transmits used to capture motion estimation data may be selected responsively to a predicted quality of the motion estimates based on strain in the body structure. The time difference between the successive transmits used to capture motion estimation data may be selected responsively to a predicted quality of the motion estimates based on strain in the body structure and random error. The method of any of the foregoing claims wherein the time difference between the successive transmits used to capture motion estimation data is selected responsively to a predicted quality of the motion estimates based on an optimum responsive to a random signal component and a competing distortion of the motion estimation resulting from strain, i.e., motion other than pure displacement.

According to embodiments, the disclosed subject matter includes a system for estimating properties of motion of a body structure using ultrasound, comprising: an ultrasound probe connected to a driver and data acquisition element and a programmable processor with a user interface having a display and a data storage element. The system includes software instructions recorded on the data storage element, the software instructions defining a procedure for operating at least the ultrasound probe, driver and data acquisition element in order to execute the method of any of the foregoing claims.

According to embodiments, the disclosed subject matter includes a system for estimating properties of motion of a structure using ultrasound, comprising: at least one ultrasound probe configured to scan a structure using ultrasound. a controller configured to control the at least one ultrasound probe to transmit ultrasonic beams into the structure and receive echoes thereof. The controller is further configured to transmit multiple beams repeatedly over an inspection interval such that the echoes may be used to form a representation of the structure over the entire spatial scope of detection of the ultrasound probe which can be updated no more frequently than a sample frequency. The controller is further configured such that the echoes may be used to determine displacements of portions of the structure occurring within fractions of the spatial scope of detection and within fractions of the sample frequency.

The controller may be configured to accept data representing a magnitude $T_{me}$ of said fractions of the sample frequency. $T_{me}$ may represent the time separation between image samples of said portions of the structure generated by said controller responsively to said echoes. $T_{me}$ may be selected responsively to a predicted or measured maximum of a cross-correlation time scale between said image samples.

The controller may transmit beams in pairs at a frequency that is greater than the sample frequency, where each pair covers less than the spatial scope of detection.

It will be appreciated that the modules, processes, systems, and sections described above can be implemented in hardware, hardware programmed by software, software instruction stored on a non-transitory computer readable medium or a combination of the above. For example, a method for imaging can be implemented using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of ultrasonography and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, imaging methods devices and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The following example illustrates the implementation of two different ultrasound sequences used to obtain high frame rate 2-D cardiac strain estimation in vivo over a single heart cycle. Qualitative results in a standard clinical imaging setting indicate that each method can be used to obtain physiologic strains. An evaluation framework based on the expected value of the SNRe was explained and used to study the influence of frame-rate, or more specifically MER, on both axial and lateral strains. The results indicate a strong relationship with the concept of the strain filter. Strain estimation quality was found to increase with MER, at least for the axial direction, and MER should be at least ≥500 Hz to avoid the suboptimal motion estimation governed by the Barankin bound. Results in the lateral direction indicate that lateral strain estimation is less tied to MER. This study also finds little difference in strain estimation quality using a conventionally focused beam compared to a diverging beam.

Example 1

A. Experimental Set-Up

Using a protocol approved by the Institutional Review Board of Columbia University, three, healthy male volunteers aged 23-28 were scanned in the lateral decubitus position by a trained cardiac sonographer. All patients were scanned with a 2.5 MHz phased-array probe connected to a Verasonics scanner using two custom imaging sequences described in the next section. For each sequence, acquisition lasted for 2 seconds to ensure the capture of an entire cardiac cycle. The same view was taken in all patients; namely, the parasternal short-axis view at the papillary muscle (mid-) level. Because the objective was to analyze and compare both axial and lateral strain estimations, the short-axis view was chosen so that the magnitudes of the strains would be similar in each direction.

B. Imaging Sequences

Figure 18A:
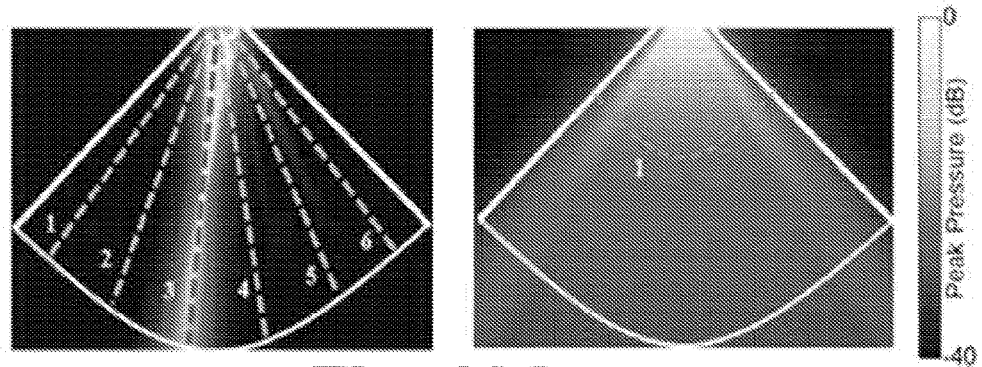
FIG. 18A shows the preak pressure versus angle to compare the TUAS sequence with the unfocused sequence.
Figure 18B:
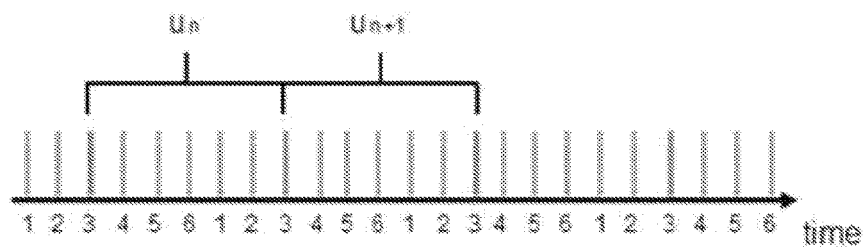
FIG. 18B illustrates the temporal profile of displacement estimation using a traditional sequence.
Figure 18C:
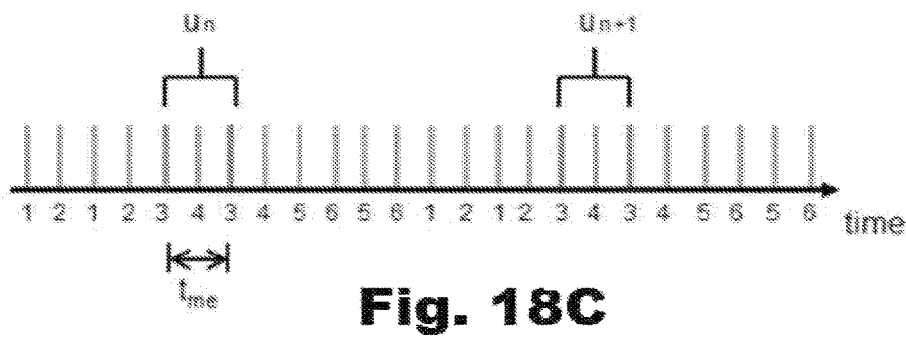
FIG. 18C illustrates the temporal profile of displacement estimation using TUAS sequence.
Figure 18D:
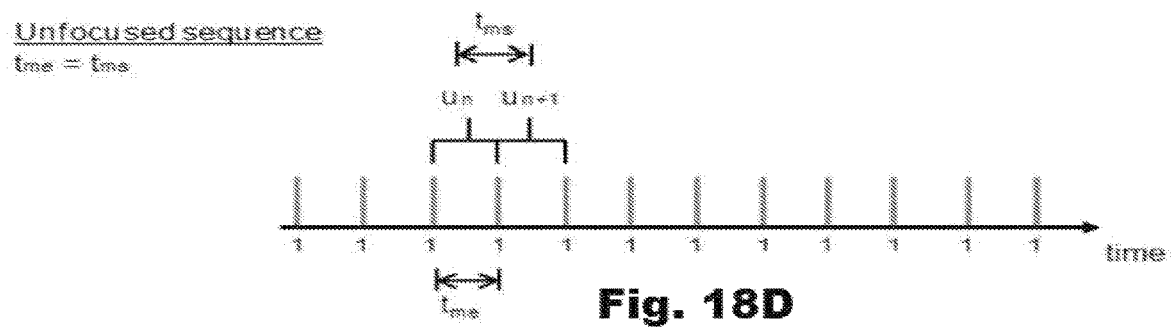
FIG. 18D illustrates the temporal profile of displacement estimation using an unfocused sequence.
Figure 19A:
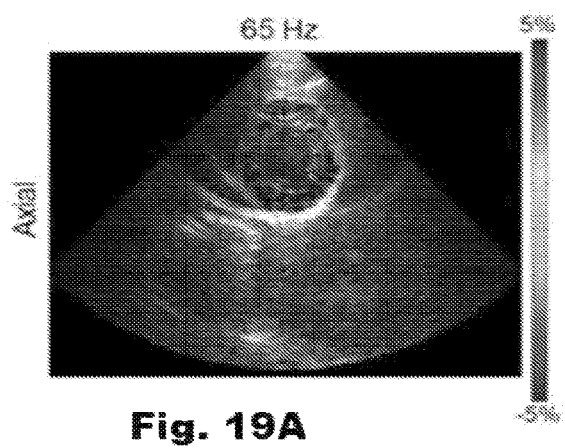
FIGS. 19A, 19B, 19C, and 19D depict single frames of axial and lateral incremental strain estimation using TUAS at MERs of 65 Hz and 815 Hz.
Figure 19B:
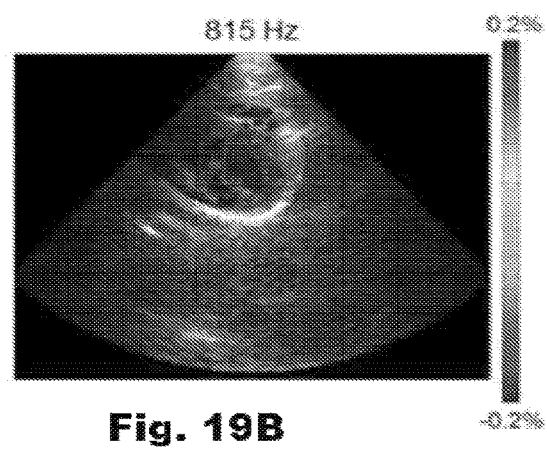
Figure 19C:
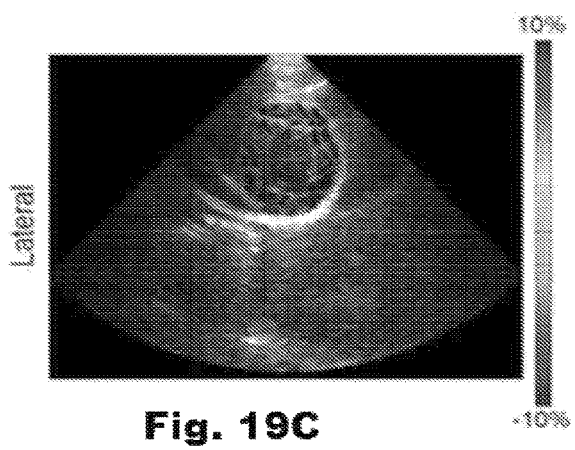
Figure 19D:
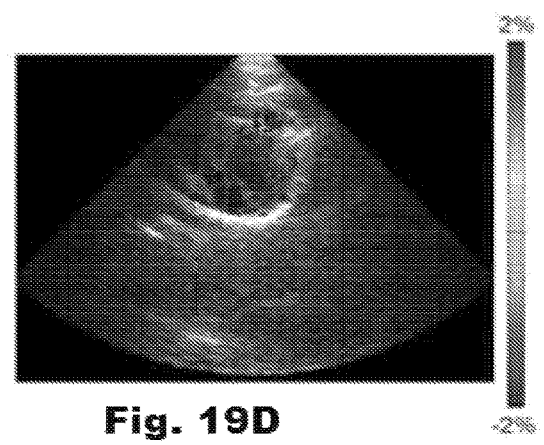

Two custom imaging sequences were used in this study in order to achieve high frame-rate imaging in a single heart-beat without compromising field of view, depth, or number of lines. The first sequence is referred to as temporally unequispaced acquisition sequence (TUAS), and relies on the modification of the transmission order of focused beams to achieve high frame rate motion estimation. The second imaging sequence, referred to as the unfocused sequence, uses a single, diverging beam to interrogate the tissue instead of multiple focused beams. Traditional echocardiography is performed by emitting and receiving focused acoustic waves in a sequential fashion. Equation 12

$$Frame\ Rate_{max} = \frac{c}{2Nd} \qquad (12)$$

describes the fundamental relationship between frame rate, beam density (N=number of lines), imaging depth (d), and speed of sound (c) using a traditional acquisition sequence. A single image frame in time consists of N consecutive lines that form a circular sector field of view; typically, at least 64 lines that cover a 90° field of view are used. Displacement estimation is performed between lines of two frames acquired consecutively in time. FIG. 18B illustrates the temporal profile of displacement estimation using a traditional sequence. Each of the displacement estimations ($u_n$ and $u_{n+1}$) is made using the same line, which corresponds to "3" on the graph. The time elapsed between two consecutive acquisitions of the same line is denoted by $t_{ME}$. This time represents the time over which motion estimation occurs. Similarly, the time elapsed between two motion estimation measurements is denoted as $t_{MS}$. The inverses of these two time intervals are referred to as the motion estimation rate (MER) and motion sampling rate (MSR) respectively. In practical terms, the MER influences the quality of the motion estimation, while the MSR represents the sampling frequency of that motion estimation. In conventional ultrasound imaging, the MER is equal to the MSR (FIG. 18B The utility of TUAS is derived from the fact that by decreasing the MSR, a higher MER is able to be achieved. The increase of MER in TUAS is achieved by the repeated acquisition of smaller sectors of the heart (FIG. 18C). These repeated acquisitions allow for a few lines to be imaged twice in the very short period of time—increasing the MER—although those same lines are not imaged again for an extended period of time—decreasing the MSR. Since motion estimation relies on the repeated acquisition of the same line, the MER for each sequence will depend on the number of lines per repeated sector. In this sense, Equation 12 could be used to compute the MER for each TUAS, with N being the number of lines per sector. FIG. 36 (Table 1) lists the sector sizes used in this report and the corresponding MERs. Note that the MERs are slightly lower than those predicted by Equation 12 due to data transfer times inherent to the scanner. The 1-sector sequence at 272 Hz can be considered the conventional sequence; however, to achieve the even lower MER of 65 Hz, motion estimation was also performed over the large, MSR interval (i.e. $t_{ms}$ in FIG. 18) instead of the smaller MER interval.

The unfocused sequence differs more drastically from the conventional sequence than does TUAS. Instead of multiple, focused beams being transmitted per frame, the unfocused sequence uses a diverging wave that interrogates the entire view only once per frame (FIGS. 18A through 18D). The reconstruction of the entire field of view is made possible by the acquisition of individual-element radiofrequency (RF) data, permitting synthetic focusing in post-processing to create multiple image lines. This synthetic focusing procedure is performed for both the TUAS and unfocused sequence, and is explained in further detail in the next section. Because each frame is formed using only a single transmit, motion estimation can be performed on a given frame using both the previous and the next frame in the sequence.

Therefore, similarly to a conventional sequence, the MER and MSR for the unfocused sequence are equivalent, although greatly increased due to the fact that only a single transmit per frame is required. Individual frames were acquired at a MER of 2000 Hz, and were also downsampled in time to 250, 500, and 1000 Hz by using every eighth, fourth, and second frame respectively for motion estimation.

C. Data Acquisition

For each sequence, pre-beamformed radiofrequency (RF) data was sampled at 10 MHz and recorded for each of the 64 individual traducer elements. The data were fairly large, approximately 1 GB for 2 seconds, and were transferred to an on-board CPU and stored. For beamforming, a standard delay-and-sum algorithm was used to reconstruct 128 lines of post-beamformed RF data per frame. For the TUAS, this corresponds to the construction of approximately 11 RF lines per transmit beam; while in the unfocused sequence, all 128 lines were constructed from a single transmit. A 90° field of view at a depth of 20 cm was used to mimic standard clinical settings. ECG measurements were also acquired in parallel with the ultrasound measurements.

D. Strain Estimation

A fast, normalized cross-correlation function was used on RF lines from adjacent frames to compute two-dimensional motion. The cross-correlation function used a 1-D kernel (length=8.0 mm, overlap=90%) in a 2-D search to estimate both axial and lateral displacements. When searching in the lateral direction, RF data was interpolated by a factor of 10 in order to improve lateral displacement resolution. A least-squares kernel (9.2×9.5 mm) was then used to compute the 2-D strains. The calculated displacements were taken from a reference point of the first frame in each estimation pair yielding incremental (inter-frame) displacements and strains, as opposed to performing accumulation over the entire cardiac cycle. Therefore, the strain values at each point in time reflect the behavior of the tissue at that specific time point, without being influenced by any previous behavior. A standard B-mode image was reconstructed from the RF data, allowing for the segmentation of the myocardial border. These contours were automatically tracked through time using a previously described technique.

E. Performance Evaluation

A probabilistic framework has been used here in order to compare the strain estimation quality of the various sequences used in this study. First, the elastographic signal-to-noise-ratio ($SNR_e$) was calculated for each sequence over the entirety of the heart cycle. $SNR_e$ is computed for every point in an image using Equation 13.

$$SNR_e = \frac{\mu}{\sigma} \quad (13)$$

In (3), μ and σ refer to the mean and standard deviation of the strain magnitudes within a small 2-dimensional window. Since both strain and $SNR_e$ are computed for each myocardial point during systole, a large number (>600,000) of strain-$SNR_e$ pairs were generated for each sequence. This paired data can be used to generate a two-dimensional histogram (f($SNR_e$,ε)) that displays the probability density function (pdf) of $SNR_e$ for a set of discrete strain values. However, since the strain distribution measured in the heart is non-uniform, the 2-D pdf will be biased towards strain values that occur more frequently. To remove this bias, the conditional pdf was calculated according to $$f(SNR_e \mid \varepsilon) = \frac{f(SNR_e, \varepsilon)}{f(\varepsilon)} \quad (14)$$

where f($SNR_e$,ε) is the 2-D pdf and f(ε) is the 1-D strain distribution. It is important to keep in mind that f($SNR_e$|ε), f(SNR$_e$,ε), and f(ε) will be affected by the quality of strain estimation and thus be dependent on the MER.

To simplify the information obtained from the 2-D conditional pdf, which manifests as a 3-D plot, the conditional expected value of SNR$_e$ for each strain was calculated as $$E(SNR_e|\varepsilon) = \int_0^{+\infty} SNR_e f(SNR_e|\varepsilon) dSNR_e \qquad (15)$$

E(SNRe|ε) curves are generated for each sequence, which allows for a relatively easy comparison to be performed between different sequences for a wide range of strain values.

However, since incremental strains are being used, it is important to keep in mind that the same deformation will be measured differently by sequences with different MERs. For instance, a 1% strain measured at 1000 Hz would be measured as a 2% strain at 500 Hz. Therefore, in order to compare strain magnitudes between sequences, strains have been multiplied by MER for normalization. Final magnitudes of normalized strain are presented in decibels, with the reference of 0 dB being a 1% strain measured at 100 Hz.

Results

A. Qualitative Results

Figure 20A:
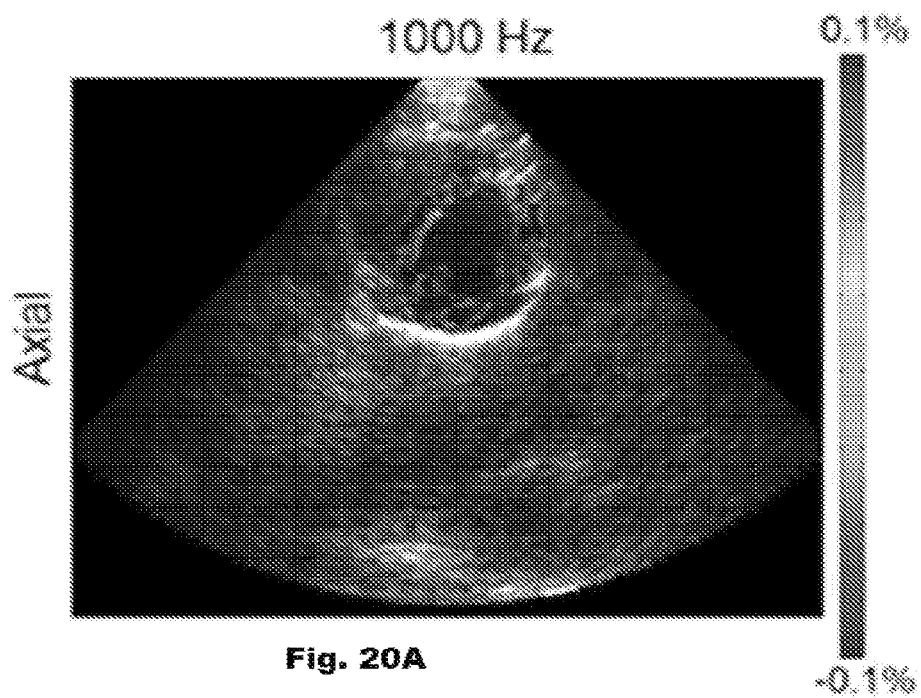
FIGS. 20A and 20B present qualitative results for the unfocused sequence at an MER of 1000 Hz.
Figure 20B:
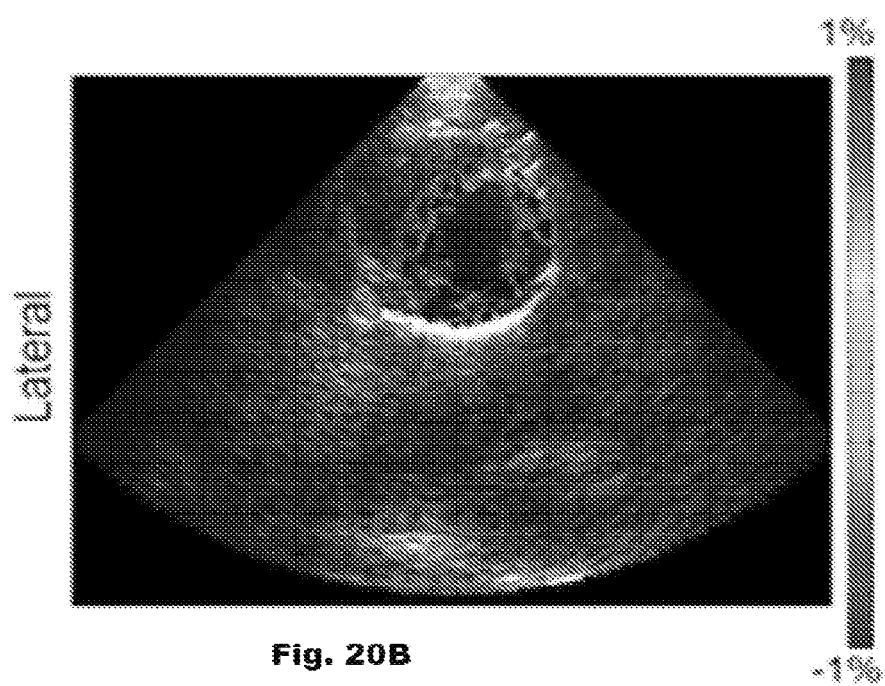

FIG. 19 depicts single frames of axial and lateral incremental strain estimation using TUAS at MERs of 65 Hz and 815 Hz. All images were taken at the first incremental step following end-diastole, defined as the time of QRS peak amplitude on the ECG. No filtering was performed on the displacements or strains in these images. Note that strain magnitudes are presented in percent, instead of the normalized strain used for the quantitative analysis. Because these strains are incremental instead of cumulative, their magnitude will be dependent on the MER used, since the estimation interval is longer for lower MERs. FIG. 20 presents qualitative results for the unfocused sequence at an MER of 1000 Hz, also taken immediately following end-diastole.

B. Axial Strain

Figure 21:
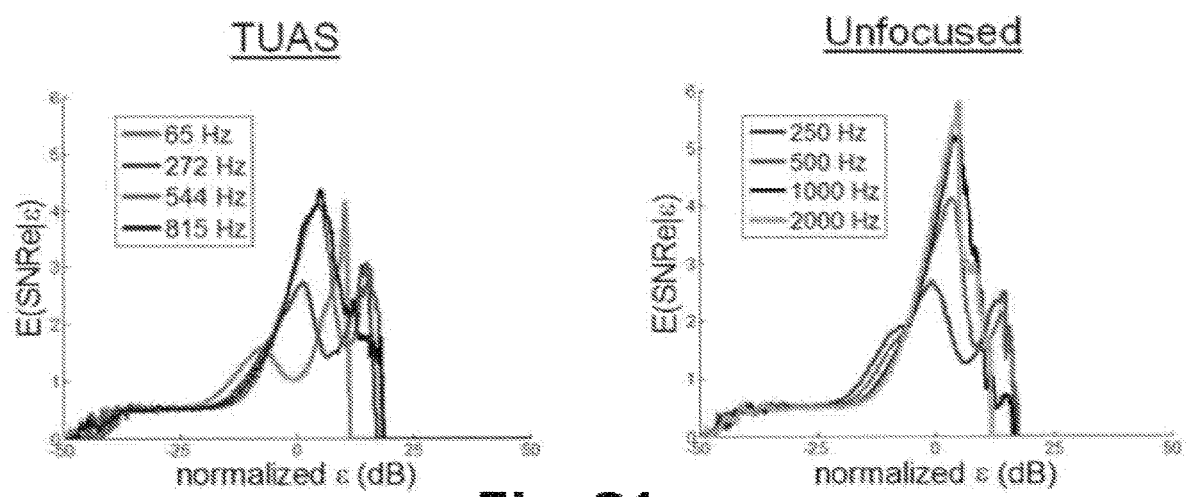
FIG. 21 shows an E(SNRe|ε) curve for the axial strain for both TUAS and unfocused sequences at various MERs.
Figure 22:
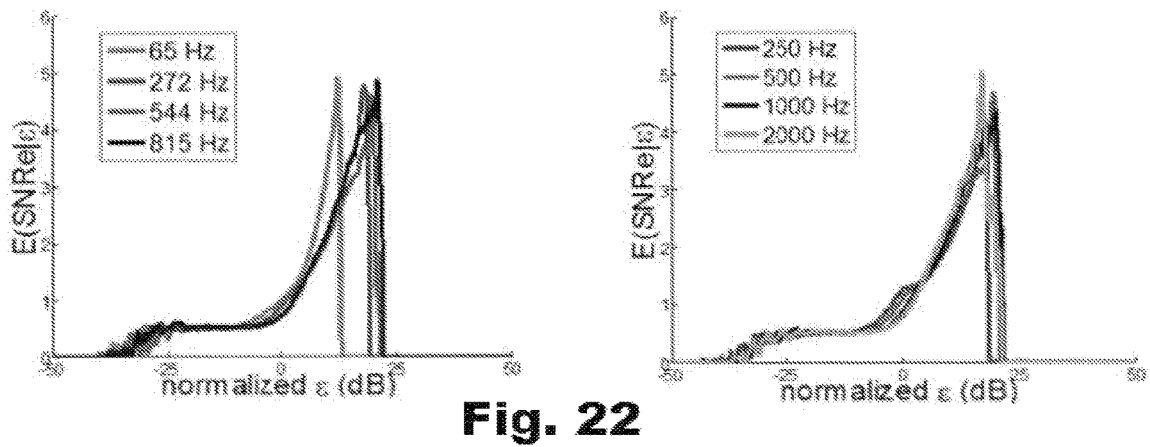
FIG. 22 shows an E(SNRe|ε) curve for the lateral strain for both TUAS and unfocused sequences at various MERs.

E(SNRe|ε) curves are shown in FIGS. 21 and 22 for both sequences at various MERs. For the axial case, the curves exhibit a two-peaked, bimodal distribution. The locations of both peaks shift towards larger values of strains for higher MERs. This shift becomes less apparent at MERs 500 Hz, in which case the locations of the first peak are clustered at approximately 10 dB. This phenomenon occurs for both the TUAS and unfocused sequence, although the shifting behavior is more apparent using TUAS since the MERs tested are lower. The amplitudes of the first peaks also increase with MER while the amplitudes of the second peaks decrease, causing the shape to approach unimodal at higher MERs. The maximum value of E(SNRe|ε) for any sequence is 5.8, occurring for the unfocused sequence at an MER of 2000 Hz at a strain of approximately 10 dB. This magnitude corresponds to an incremental strain magnitude of 0.16% at 2000 Hz. The curves for the two sequences at similar MERs (272 and 544 Hz for TUAS; 250 and 500 Hz for unfocused) have approximately the same shape and magnitude of the first peak, although the magnitude of the second peak is slightly decreased in the unfocused sequence.

C. Lateral Strain

In contrast to the bimodal distributions observed for the axial direction at low MERs, all E(SNRe|ε) curves appear unimodal for the lateral direction, regardless of MER. However, similar to the axial direction, the curve peaks shift to the right with increasing MER in the TUAS case, although this phenomenon is less clear above 272 Hz. For higher MERs, the locations of the peaks do not change significantly and are clustered around 40 dB. Unlike the axial direction, the magnitudes of the peaks of the curves do not seem to change significantly with MER; the maximum magnitude of each curve is approximately 4.7. Again, at similar MERs, the TUAS and unfocused sequence curves appear similar in magnitude and shape.

Discussion

The qualitative results presented in FIGS. 19 and 20 show the feasibility of measuring in vivo cardiac strain using each sequence, provided the MER is sufficiently high. It can be seen from FIG. 19 that the estimated strain at 65 Hz is much less uniform compared to 815 Hz, as well as being much less reflective of the underlying pathology. At end-diastole, the left ventricle is just beginning to contract, leading to positive radial strain (thickening) in the short axis view. This phenomenon would manifest as positive axial strain at the anterior/posterior walls, as well as negative axial strain at the septal and lateral walls. FIG. 19C clearly shows thickening in the anterior/posterior walls, as well as axial thinning in the septum. However, strains in FIG. 19A do not seem to be isolated to a particular wall segment in a way that makes pathological sense. Conversely, lateral strain should manifest as negative strain in the anterior/posterior walls and positive strain in the septal and lateral walls. This distribution can be seen in FIG. 19A, but is less apparent in FIG. 19C. It is important to note that since the two MERs were obtained with two separate sequences and acquisitions, it is difficult to capture the exact same time point, especially since the incremental strain distribution changes so rapidly. However, ECG recordings synchronized with the ultrasound measurements were used to identify approximately the same point in the cardiac cycle.

The qualitative results for the unfocused sequence depicted in FIG. 20 were taken at the same point in the cardiac cycle as the images from FIG. 19, immediately following end-diastole. Therefore, the physiological deformations occurring should be similar to those described above. Again, it was difficult to ensure the selection of the exact same time point due to the separate acquisitions. Indeed, the axial and lateral strain distributions in FIG. 20 are not exactly the same as in FIG. 19, although they do show similarly reasonable results. Axial thickening and lateral shortening is observed in the posterior wall, as well as axial shortening and lateral thickening in the septal and lateral walls.

The transition zone occurs at high strains when decorrelation becomes too great and motion must be tracked on the basis of signal amplitude only, i.e. the signal envelope, instead of using both the amplitude and the phase information inherent to any RF signal. Smaller strains below the transition zone are tracked using both amplitude and phase information, with estimation quality being governed by a modified version of the Cramer-Rao lower bound (CRLB) for time-delay estimators. For larger strains above the transition zone, phase information is lost due to significant signal decorrelation, and the estimation quality is instead governed by the Barankin bound (BB). For strains near the transition zone, the method of motion estimation is ambiguous and inconsistent, causing a local minimum of SNRe. In this work using E(SNRe|ε), similar, two-peaked results are reported, with the disappearance of the second peak above an MER of 544. The disappearance of the second peak is due to the fact that smaller incremental strains will be measured at high MERs. If MER is sufficiently high, the majority of strain values will be below the transition zone, leading to a disappearance of the second peak.

Motion estimation using RF signal envelope has consistently been shown to be less accurate than using both phase and amplitude; thus, any axial motion estimation technique should aim to minimize the amount of strains estimated using only the envelope. Sequences with a single-peaked distribution of E(SNRe|ε) should be preferred over a sequence with a two-peaked distribution.

The E(SNRe|ε) distribution of the lateral strain estimation is single-peaked for all MERs. A single-peaked distribution is expected for the lateral direction due to the difference method of motion estimation compared to the axial direction. Although axial phase information is used to increase the accuracy of the lateral motion estimation, there is no lateral phase information inherent in a collection of 1D RF lines. Therefore, the lateral cross-correlation function is only sensitive to variations in the lateral envelope. There is also a discernible rightward shift of all E(SNRe|ε) curve peaks for both directions as MER increases. This trend is much more noticeable at the lower MERs of TUAS, and is fairly insignificant at the high MERs of both sequences. To explain this shift, recall that strain magnitudes were normalized by the multiplication of MER. For the 815 Hz sequence, a maximum occurs at an axial normalized strain of 10 dB, which corresponds to a strain of 0.4% estimated at 815 Hz. This strain magnitude reflects the optimal deformation amount for motion estimation at 815 Hz. However, for the same value of normalized strain, estimation with a 65 Hz MER will experience significantly more decorrelation compared to an MER of 815 Hz, since the estimation interval is longer. Therefore, the peaks corresponding to optimal motion estimation for the 65 Hz sequence must exist at a lower normalized strain value, where there will be less decorrelation. This explanation can be applied to the lateral E(SNRe-|ε) curves as well. At high MERs, decorrelation is significantly decreased, causing the locations of the curve maxima to settle at one particular value, which is 10 dB and 40 dB for axial and lateral strains respectively.

Figure 23:
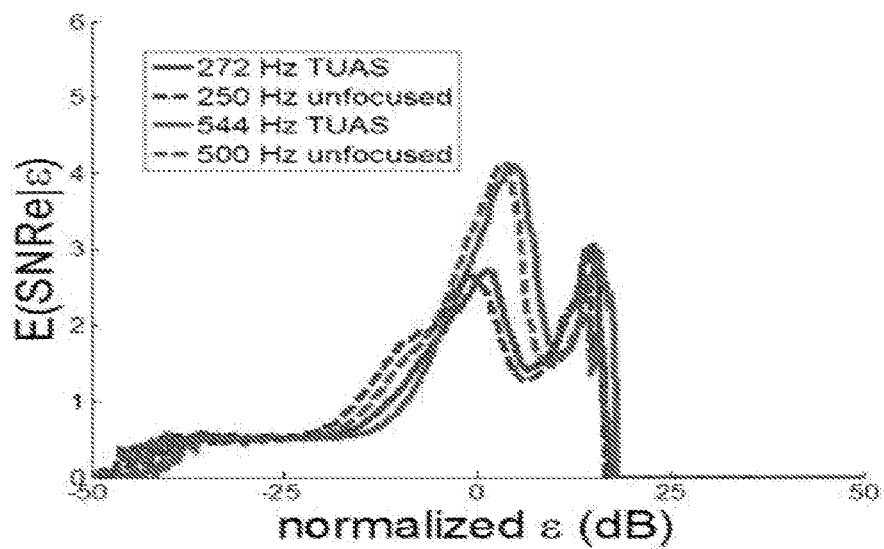
FIG. 23 compares the TUAS sequence at 272 and 544 Hz with the unfocused sequence at 250 and 500 Hz.

The high MERs used in this study were achieved by the use of two different sequences, TUAS and the unfocused sequence. The differing nature of the beam used by each sequence was thought to potentially have an impact on the quality of strain estimation, especially in the lateral direction. Indeed, previous studies using simulations and ex vivo phantoms have explicitly shown the effect of beam width, among other parameters, on the quality of lateral motion estimation. A comparison between the two sequences can be performed at similar MERs, since the parameters of depth, field of view, and beam density are held constant in the data processing phase (FIG. 23). In comparing the TUAS at 272 and 544 Hz with the unfocused sequence at 250 and 500 Hz, it is clear that each sequence produces fairly similar curves for both axial and lateral strains. The similarities in the curves extend to both magnitude and shape. A slight difference is noted for axial strains, as the amplitude of the second peak is increased in the TUAS compared to the unfocused sequence, although the relative amplitude of the first peak is still larger in both sequences. This observation suggests that, in terms of evaluation metric and study design, the 2-D strains estimated by each sequence are equivalently reliable, assuming that imaging and strain estimation parameters are held constant. Microbubbles may be employed in agent delivery devices, methods, and systems. They may allow on-demand ultrasound-triggered release of agents, enzymes, and other factors that are useful in tissue engineering. Methods and systems for controlling the release of drugs in a patient using encapsulated drug depots as described in International Patent Publication WO/2011/075557 to Kohane, et al., which is hereby incorporated herein by reference as if set forth in its entirety herein. This publication describes injectable or implantable drug delivery vehicles that permit the release of drugs by ultrasound in a patient. The described systems employ a drug depot and a drug-encapsulated in an encapsulating material. The present embodiments may employ similar depot structures and systems to release bioactive agents into tissue scaffolds.

Figure 24:
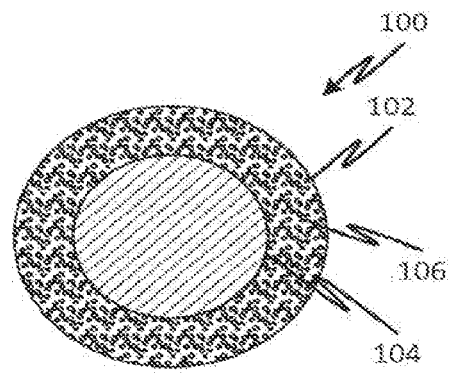
FIG. 24 shows an agent depot which comprises an agent-containing material encased in an encapsulating shell that may be disrupted by ultrasound to permit the diffusion of the agent into a surrounding environment.

Referring to FIG. 24, presently disclosed are agent depots, one of which is shown at 1. It contains an agent 104 (depicted as a separate structure 104 but may be a single structure combining the encapsulating material and agent as well) that influences the growth or behavior of cells in an engineered tissue or precursor thereof. The agent 104 may include a hydrogel or other material, including polymers that form non-hydrogel matrices following crosslinking. The agent 104 may contain one or more agents, enzymes, nutrients, or other biologically active agents. An encapsulating shell 102 may be of similar or identical material as combined with the agent to form the core 104, but which further incorporates microbubbles 106 such as liposomes. The microbubbles may contain any biocompatible gas or mixture of gases. The microparticles enhance the release of agent from the core 104 when ultrasound is applied to the shell and the energy absorbed by the microbubbles causing them to disrupt the shell or fill the microbubbles thereby permitting or enhancing diffusion or convection of the core materials into the surrounding material.

Figure 25:
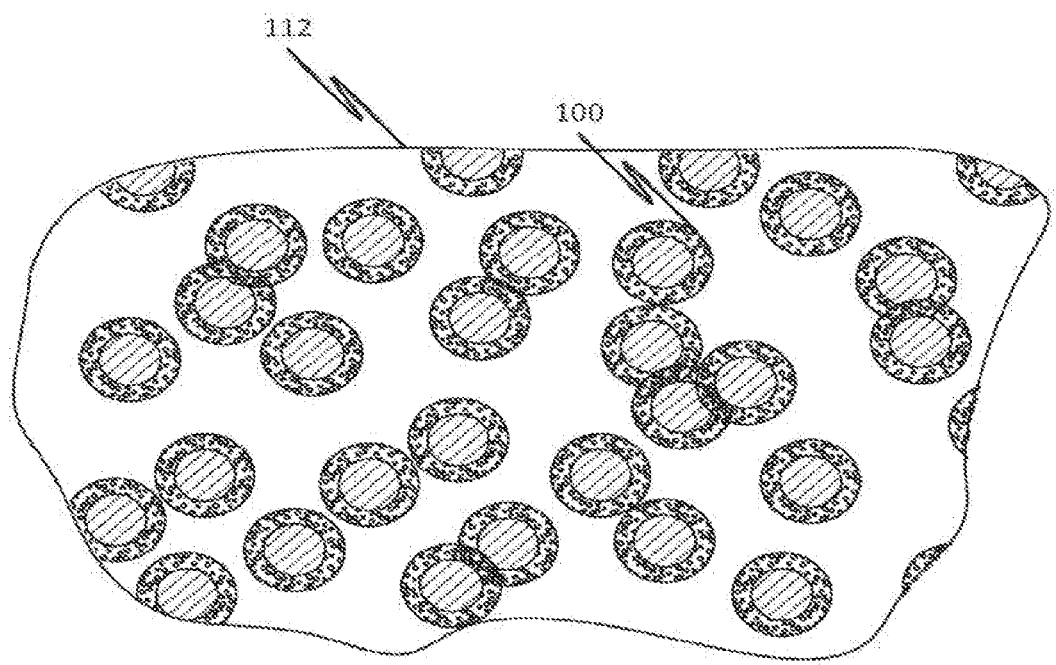
FIG. 25 shows the agent depot in a tissue scaffold, for example, a polymerizable material such as a hydrogel such as alginate which may be cell-seeded.
Figure 26A:
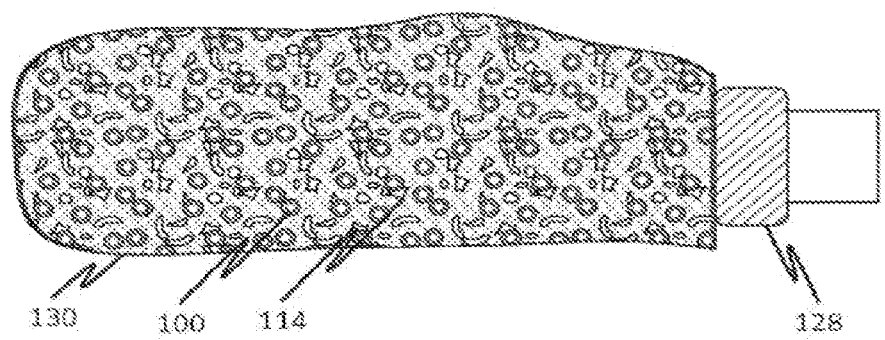
FIG. 26A shows a cell-seeded tissue scaffold with embedded agent depots with an ultrasonic emitter configured to focus ultrasound energy on selected parts of the tissue scaffold to release an agent into the tissue scaffold and influence the development of cells.
Figure 26B:
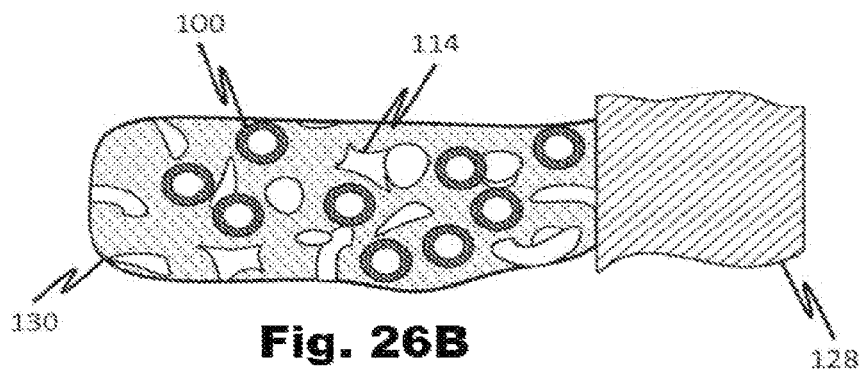
FIGS. 26B and 26C are close-ups of the configuration of FIG. 26A showing, respectively, intact agent depots with isolated contents and agent depots whose encapsulating shells have been opened.
Figure 26C:
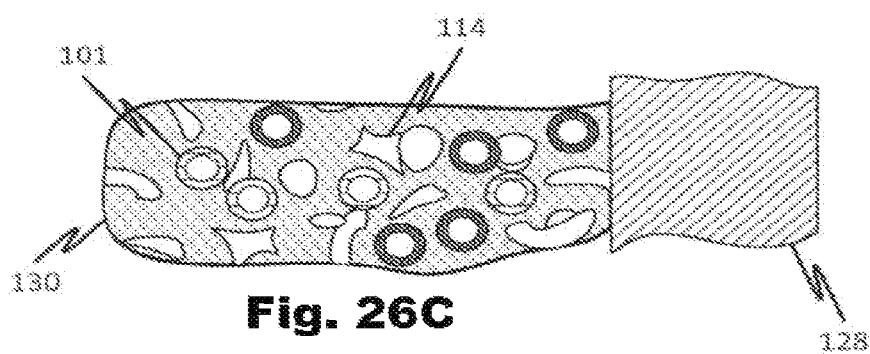

Referring to FIG. 25, agent depots 100 may be formed and incorporated in a tissue scaffold 112 such as by combining with a hydrogel precursor prior to forming of the tissue scaffold. The tissue scaffold may be seeded with cells. Referring to FIG. 26A, a tissue scaffold 130 contains agent depots 100 and cells 1. Referring also to FIGS. 26B and 26C, an ultrasound transducer 128 directs focused sound energy into the tissue scaffold causing the encapsulated agent in agent depots 100 to be released into the tissue scaffold 130 at the parts of the tissue scaffold where the ultrasound energy is focused. A disrupted agent depot is indicated at 1. The ultrasound transducer 128 may employ electronic focusing or may use a reflector or other device to mechanically focus the ultrasound energy.

The depot may be a hydrogel. However, other materials, including polymers that form non-hydrogel matrices following crosslinking, may be used. The depot contains one or more agents or biologics to be delivered encapsulated in an encapsulating material. In a preferred embodiment the agent is encapsulated in liposomes. However, other encapsulating materials, such as nanoparticles, microparticles, or particles greater than 500 microns in size may be used. In a particularly preferred embodiment, the depot also contains microbubbles. The microbubbles may contain any biocompatible gas or mixture of gases. The microparticles enhance agent release from the encapsulating material in response to ultrasound by increasing the difference between baseline and peak release rates compared to the release from the same agent depot in the absence of the microparticles.

Agents incorporated in the depots 100 may include hormones, nutrients, growth factors, angiogenesis factors, or any biological agent that may influence cell growth, movement, or other behaviors. Scaffolds may include any suitable hydrogels or other water soluble polymers or other cross-linking materials with water. Agent depots may be formed by any of the mechanisms and using any of the materials described in International Patent Publication WO/2011/0755 Formed agent depots may be combined with tissue scaffold precursor prior to formation of a tissue scaffold which may include molding three-dimensional structures. Agent depots can be substantially larger than the drug depot described in the foregoing publication. This may permit the use of further casting and assembly techniques. For example, depots may be a millimeter or more in size.

Figure 27A:
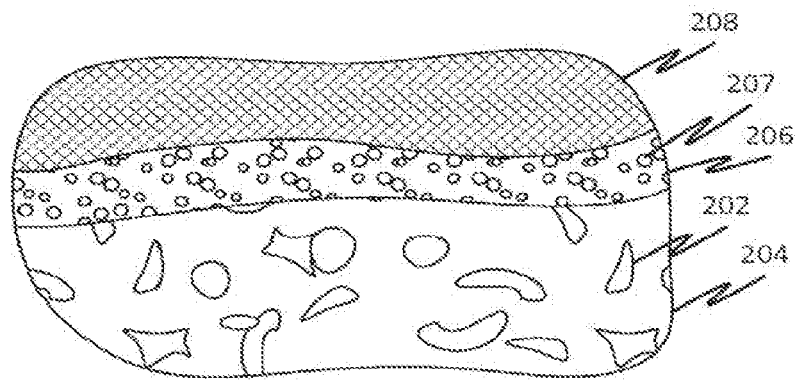
FIGS. 27A, 27B, and 27C illustrate a tissue scaffold and agent store separated by a barrier layer with microbubbles which can be disrupted at selected portions to allow the transport of an agent across the barrier layer to affect the activity of cells in the tissue scaffold.
Figure 27B:
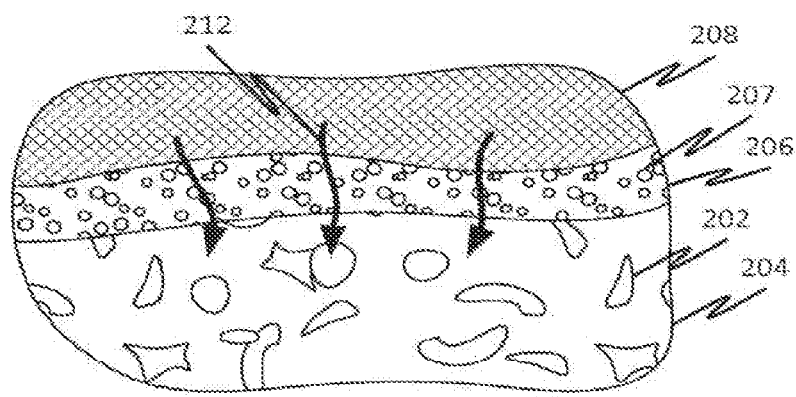
Figure 27C:
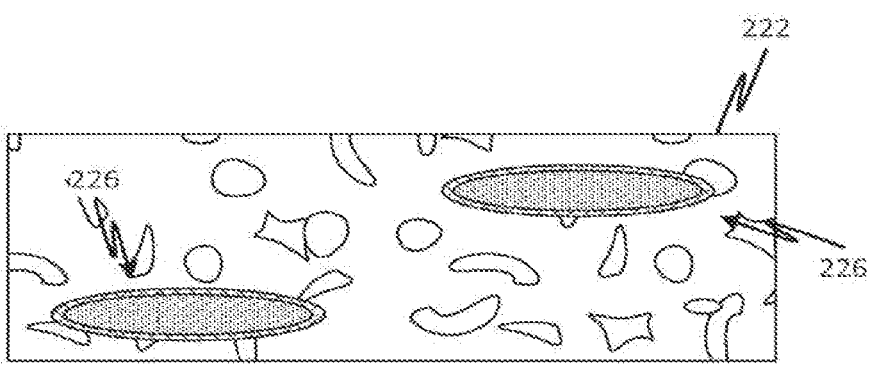

Referring to FIGS. 27A and 27B, agent depots may be macro-sized substructures adjacent to, or included in, a tissue scaffold structure such as one based on a hydrogel. A tissue scaffold 204 with cells 202 is adjacent to, or incorporates, a barrier structure 206 filled with air filled microbubbles 207 which isolates from target cells 202 an agent containing structure 208 which may be of the material used for storing agents in the foregoing agent depot embodiments. The structures 204, 206, and 208 may be of any arbitrary form and variegated dimensionally along any and all of three orthogonal axes to form arbitrary three-dimensional shapes. At an outer boundary, an ultrasound transducer may be contacted to one of the structures 204, 206, and 208, through a coupling medium such as a liquid if desired, and ultrasound energy focused onto selected parts of the barrier structure 2. The dissipation of ultrasound energy in the microbubbles 207 may disrupt the material of the barrier structure 206 (e.g., same material as described above such as hydrogel) forming channels therein. The channels may permit the convection or diffusion of agent from the agent-containing structure 208 as indicated by arrows 212 in FIG. 27B. Ultrasound energy may be directed to focus narrowly on the barrier structure to form one or more channels by disrupting the microbubbles and/or surrounding regions of the barrier structure. Note that barrier structures may be part of one or more macrosized (e.g., multiple millimeter or centimeter sized) castings 226 embedded in tissue scaffold 222 as indicated in FIG. 27C. The barrier structure may include microbubbles.

Figure 29A:
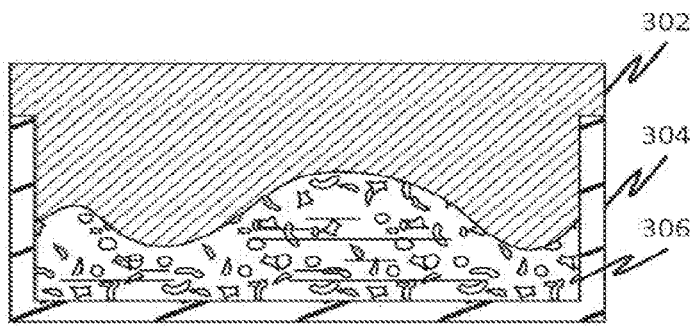
FIGS. 29A, 29B, and 29C illustrate a method of forming a three-dimensional tissue scaffold with agent depot and barrier layer features.
Figure 29B:
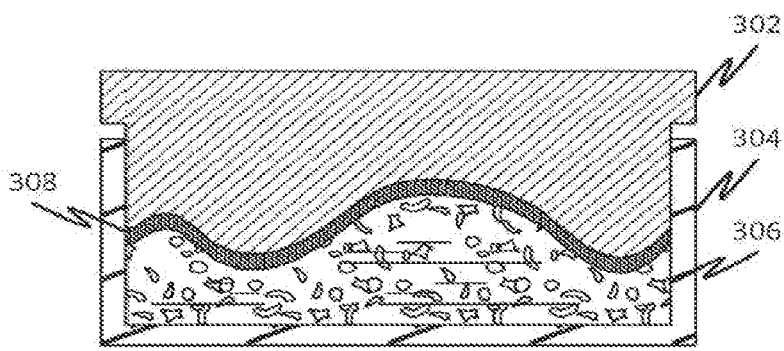
Figure 29C:
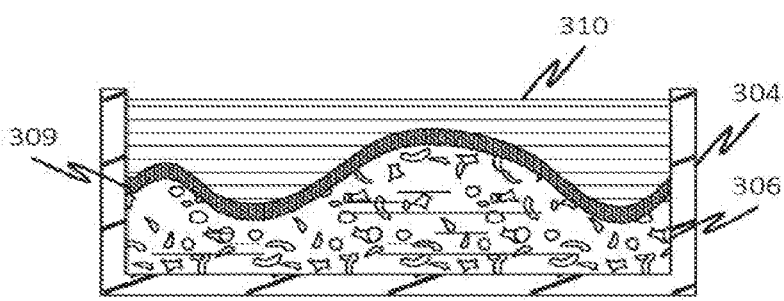

FIGS. 29A through 29C illustrate one method of forming the tissue scaffold, barrier structure, and agent-containing structures described above. A tissue scaffold 306 structure may be formed such as by casting in a mold 302, 3. A flowing precursor 308 of the barrier layer with incorporated gas-filled microbubbles may be added and molded using the formed tissue scaffold to shape an adjacent surface thereof as shown in FIG. 29B. After forming the barrier structure 309, the mold 302 can be removed. Then the agent-containing precursor 310 can be flowed into an adjacent volume and formed as illustrated in FIG. 29C.

Figure 28A:
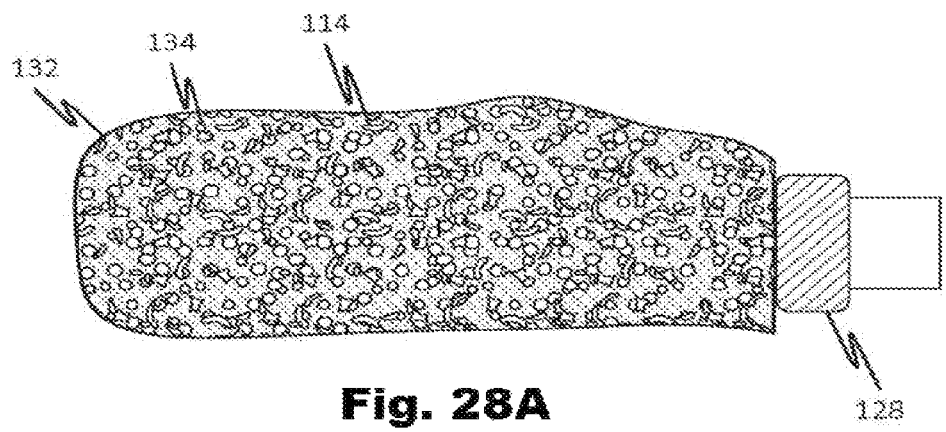
FIG. 28A shows a tissue scaffold seeded with cells and microbubbles with an ultrasonic emitter configured to focus ultrasound energy on selected parts of the tissue scaffold to disrupt selected microbubbles causing them to fill with fluid from the scaffold thereby enhancing diffusion or convection through channels or low diffusion resistance regions defined thereby.
Figure 28B:
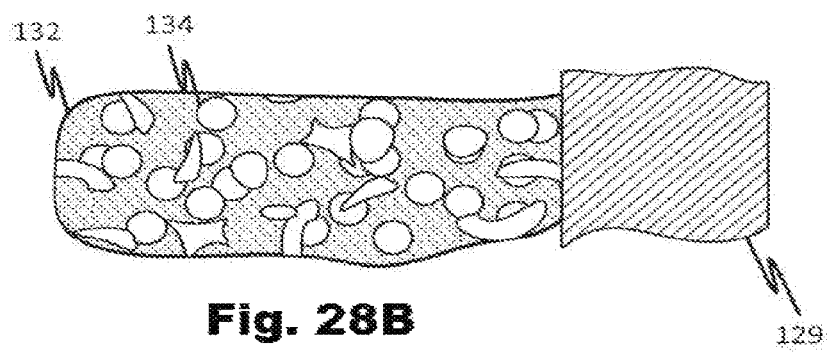
FIGS. 28B and 28C show close-ups of the configuration of FIG. 28A and, respectively, intact microbubbles and selectively disrupted microbubbles.
Figure 28C:
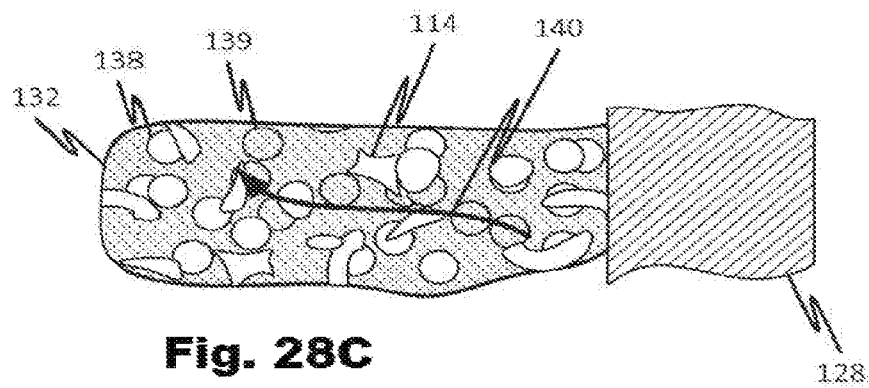

Referring now to FIGS. 28A and 28B, a cell (114)-containing tissue scaffold 132 includes microbubbles 1. A focusing ultrasound emitter 128 is in direct contact with the scaffold 132 or contacts the scaffold 132 through a coupling material such as a perfusate bath. The ultrasound emitter 128 (shown in part at 129 in the zoomed in illustration of FIGS. 28B and 28C) direct energy to specific internal regions of the tissue scaffold 132 to disrupt the microbubbles as indicated in 139 causing them to fill with fluid from the surrounding scaffold. The diffusion or convection of fluid through the now-filled microbubbles is enhanced. Multiple microbubbles may be disrupted along a path to form channels 140 in the tissue scaffold 1. The same ultrasound emitter 128 or a different one may, upon forming the channels by so disrupting the microbubbles, induce convective motion of fluid through the channels or more porous medium using acoustic streaming by applying a constant or slowly changing acoustic radiation force to the scaffold where the channels are defined. Cell seeded hydrogel tissue scaffolds with microbubbles according to the present disclosure may be as formed and described in International Patent Publication WO2011/028690 to Mark Borden, et al., filed 31 Aug. 2010. This publication also describes using ultrasound to cause the microbubbles to be disrupted using ultrasound and to enhance diffusive transport.

In preferred embodiments, the agent depot contains microbubbles that encapsulate a gas. The microbubbles enhance the agent release when ultrasound is applied compared to the same system in the absence of microbubbles. In a preferred embodiment, the agent delivery system contains an encapsulating material, preferably liposomes, an agent to be delivered, microbubbles, and at least two hydrogel-forming precursor components. In embodiments, the agent depot also contains microbubbles that encapsulate one or more gases. The microbubbles enhance the agent release when ultrasound is applied compared to the same system in the absence of microbubbles. As used herein, microbubbles refer to micron range-sized spherical gas-filled particles, which can be stabilized by an organic coating, such as a lipid shell, at the gas-liquid interface. Microbubbles having a diameter of 10 microns or less can be generated and used as contrast agents. Depending on controlled ultrasound parameters, the microbubbles may be destroyed by externally applied ultrasound of sufficient intensity so as to release shell material as well as any gas contained by the microbubble shell.

Figure 30:
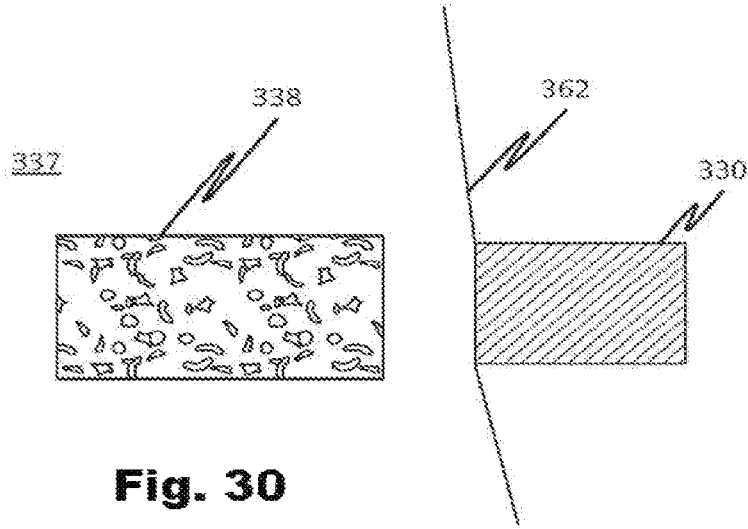
FIGS. 30 and 31 illustrate a tissue scaffold supported in an acoustical coupling medium/nutrient bath in an arrangement which may mechanically stimulate the tissue scaffold and/or generate acoustic streaming of the coupling medium/nutrient bath fluid.
Figure 34:
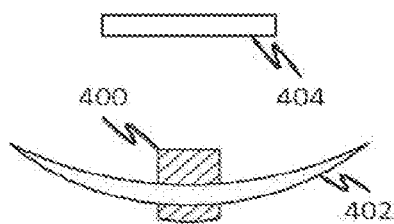
FIGS. 34 and 35 illustrate mechanical stimulation of engineered tissue structures or tissue scaffolds.
Figure 35:
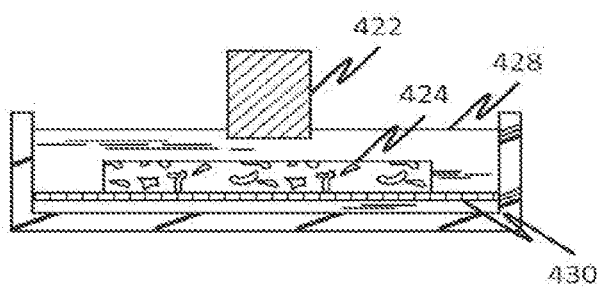

In further embodiments, in vivo, implanted, and ex vivo engineered tissues or tissue scaffolds are mechanically stimulated using ultrasound. Apparatus and methods that are suitable for this are described in United States Patent Application 20070276242 to Elisa Konofagou et al., filed 6 Apr. 2007, hereby incorporated by reference herein. Therein acoustic radiation force is applied to tissue structure and modulated at high frequency for purposes of measuring tissue properties. In the present subject matter, engineered tissue constructs or scaffolds with growing cells are loaded mechanically using the same force but modulated at power levels and frequencies suitable for the mechanical stimulation of the growing cells. Referring to FIG. 30, a tissue scaffold 338 with cells is stimulated mechanically by an oscillating acoustic radiation force from an ultrasonic emitter 3. The acoustic energy may be coupled to the tissue scaffold 338 via a medium or applied directly. The coupling may be through a living host tissue 337 where the tissue scaffold or engineered tissue 338 is implanted in a living host. The ultrasonic emitter may be pressed against the skin 362 or to the wall of a body lumen. FIG. 34 shows a tissue construct 404 (scaffold or engineered tissue) to which acoustic radiation force is applied by an emitter having a transducer 400 and focusing reflector 4. As illustrated in FIG. 35, a tissue scaffold or engineered tissue is attached to or resting on a membrane 430 and held in a liquid medium 4. An ultrasound emitter applies regular patterns of acoustic radiation force to the tissue scaffold 424 to stimulate growth, migration, differentiation, signaling or any other biological activity. The acoustic radiation force may also be used to enhance movement of perfusate through the tissue construct, for example, the coupling medium 428 may be a perfusate bath. Focusing by the emitter 422 may be electronic or mechanical.

Figure 31:
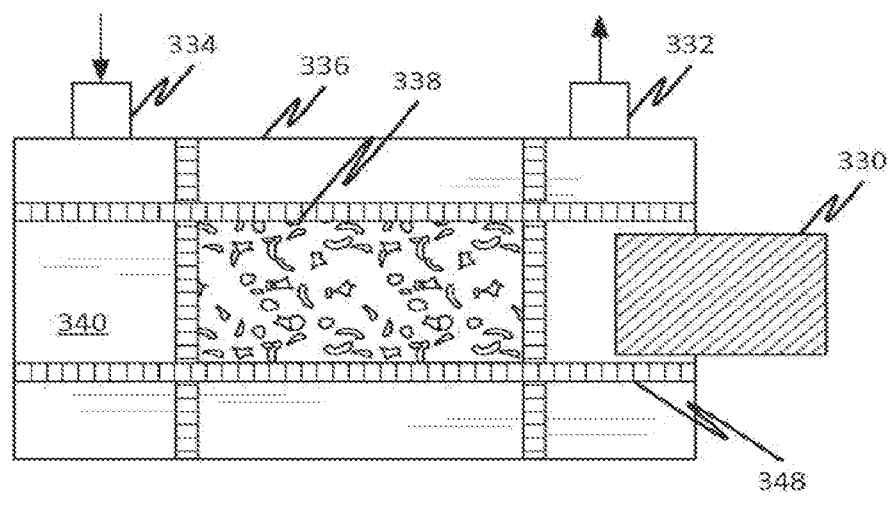
Figure 32:
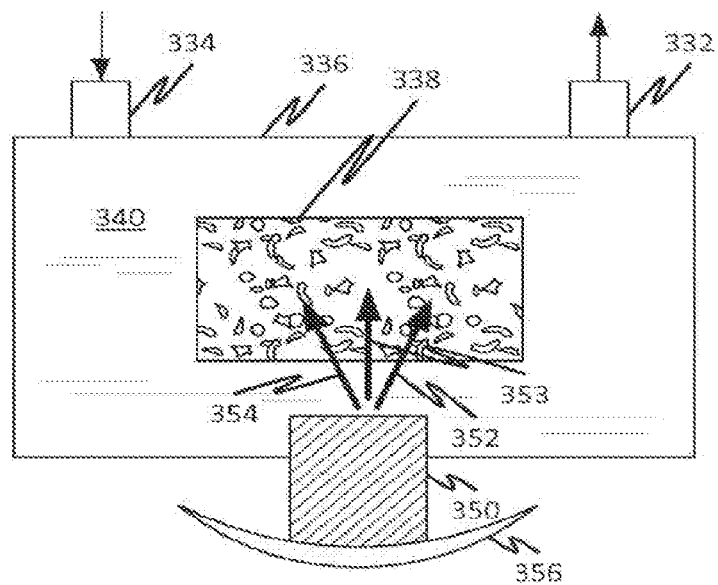
FIGS. 32 and 33 illustrate the use of ultrasound create pulsed, shifting acoustic streaming, to create channels by disruption of microbubbles and/or use of a mechanical focusing alone or in conjunction with electronic focusing.

FIG. 31 shows a tissue scaffold or tissue construct 338 supported by a permeable support 348 in a bath of coupling material 340 which may also provide nutrients and or signaling to cells in the construct 3. The bath, in a container 336, may be replenished by flow through inlet and outlet ports 334 and 3. A focused acoustic radiation force may provide acoustic streaming within the construct 338 or channels molded therein (not shown separately). This streaming may enhance the movement of fresh perfusate into the interior of the construct 3. FIG. 32 shows a similar arrangement, with the identical element labeled identically, wherein an ultrasound emitter, which may employ a reflector 356, scans the acoustic radiation force over a range of angles indicated figuratively by arrows 352, 353, and 3. A single or multiple lobes may be scanned electronically across a tissue construct 338 to induce a continuously varying strain in the construct. Multiple emitters or patterns may be combined to induce different strain spatial and temporal strain patterns in the tissue construct 3. The oscillatory force-inducing local oscillatory motion may be a single amplitude modulated ultrasound beam. The magnitude of the acoustic wave emitted by the source depends on the radiation force and the mechanical frequency response of the target construct. A system may be configured to include a transducer for inducing localized oscillatory motion of tissue through the application of the oscillatory radiation force. The mechanical stimulation can also be generated by varying the phase of two ultrasonic emitters to modulate the interference pattern. A variety of interference modes are possible to produce mechanical strain or forcing as would be apparent to those skilled in the art.

Figure 33:
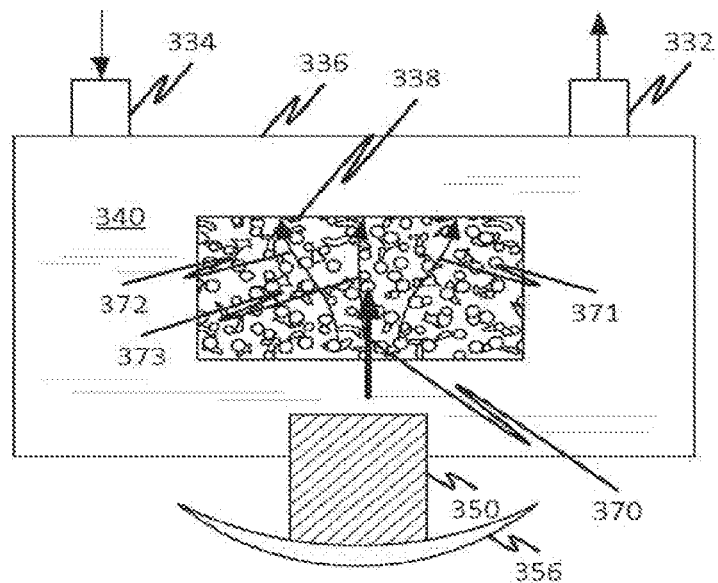

FIG. 33 a tissue scaffold or tissue construct 338, which may be supported by a support (not shown) in a bath of coupling material 340 which may also provide nutrients and or signaling to cells in the construct 3. The bath, in a container 336, may be replenished by flow through inlet and outlet ports 334 and 3. The tissue construct 338 incorporates microbubbles. An ultrasonic emitter generates a focused ultrasound beam 370 that may be controlled to create one or more flow channels such as 371, 372, and 373 in the construct 3. Then the same, or a different, emitter produces acoustic streaming. The ultrasound emitter may include a reflector 356 and transducer 3.

In further embodiments, hydrogels containing microbubbles and cells which have been homogeneously mixed in hydrogel scaffold are subjected to acoustic forces to cause dissolution of gas-filled microbubbles, creating fluid-filled pores that enhance nutrient diffusion by creating a microporosity in the hydrogel scaffold (which has a nanoporosity). Timing of microbubble dissolution can be controlled by microbubble design (size, lipid composition) that dictates microbubble stability in culture, or "on-demand" using applied hydrostatic pressure or ultrasound. Example: microbubbles (2-4 micron diameter); agarose hydrogel (~0.2 micron or 200 nm pores). The context and suitable mechanisms of the latter set of embodiments are set forth in PCT/US2010/047263.

In further embodiments, ultrasound is used to cause "on-demand" oscillation of gas-filled microbubbles encapsulated in hydrogel scaffold. This can cause local tissue deformations that a) enhance convection of nutrients from the surrounding, bathing culture media into the engineered tissue construct; b) help to distribute cell synthesized products within the scaffold; c) provide a mechanobiological signal to cells encapsulated in the gel.

Ultrasound may be applied to whole regions of the engineered construct, or on small selected subvolumes using High Intensity Focused Ultrasound (HIFU) or Harmonic Motion Imaging Focused Ultrasound (HMIFU) as described in United States Patent Application Publication No. US 2007/0276242 A1 (U.S. Ser. No. 11/697,579), incorporated herein by reference in its entirety. Here, ultrasound can be targeted at specific spatial regions and tissue depths only for localized effects. This technique may also be extended to rasterize the targeted subvolume or move the targeted subvolume in a time sequence.

In a further embodiment, a steady acoustic radiation force is applied to a tissue scaffold to induce movement of perfusate therein. This may be combined with the other techniques, systems, and methods described herein.

The foregoing descriptions apply, in some cases, to examples generated in a laboratory, but these examples can be extended to production techniques. For example, where quantities and techniques apply to the laboratory examples, they should not be understood as limiting.

Features of the disclosed embodiments may be combined, rearranged, omitted, etc., within the scope of the invention to produce additional embodiments. Furthermore, certain features may sometimes be used to advantage without a corresponding use of other features. It is, thus, apparent that there is provided, in accordance with the present disclosure, mechanisms for use in tissue engineering. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

What is claimed is:

1. A system for estimating properties of motion of a structure using ultrasound, comprising:
at least one ultrasound probe configured to scan a structure using ultrasound;
a controller configured to control the at least one ultrasound probe to transmit ultrasonic beams into the structure and receive echoes thereof;
the controller being further configured to transmit multiple beams repeatedly over an inspection interval such that the echoes may be used to form a representation of the structure over the entire spatial scope of detection of the ultrasound probe which can be updated no more frequently than a sample frequency
the controller being further configured to transmit beams in pairs at a frequency that is greater than the sample frequency;
the controller being further configured such that the echoes may be used to determine displacements of portions of the structure occurring within fractions of the spatial scope of detection and within fractions of the sample frequency.

2. The system of claim 1, wherein the controller is configured to accept data representing a magnitude $T_{me}$ of said fractions of the sample frequency.

3. The system of claim 2 wherein $T_{me}$ represents the time separation between image samples of said portions of the structure generated by said controller responsively to said echoes.

4. The system of claim 3 wherein $T_{me}$ is selected responsively to a predicted or measured maximum of a cross-correlation time scale between said image samples.

5. The system of claim 1, wherein each pair covers less than the spatial scope of detection.

6. The system of claim 1, wherein the controller being further configured to transmit beams in pairs comprises transmission of three or more beams.

* * * * *